(12) United States Patent
Mijts et al.

(10) Patent No.: US 10,640,754 B1
(45) Date of Patent: May 5, 2020

(54) ENGINEERED ENZYMES

(71) Applicant: Inscripta, Inc., Boulder, CO (US)

(72) Inventors: Benjamin Mijts, Boulder, CO (US); Juhan Kim, Boulder, CO (US); Aamir Mir, Boulder, CO (US); Kyle Seamon, Boulder, CO (US); Andrew Garst, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 16/798,315

(22) Filed: Feb. 22, 2020

Related U.S. Application Data

(63) Continuation of application No. 16/658,948, filed on Oct. 21, 2019, now Pat. No. 10,604,746.

(60) Provisional application No. 62/748,668, filed on Oct. 22, 2018.

(51) Int. Cl.
    *C12N 9/22* (2006.01)

(52) U.S. Cl.
    CPC .................................... *C12N 9/22* (2013.01)

(58) Field of Classification Search
    None
    See application file for complete search history.

(56) References Cited

U.S. PATENT DOCUMENTS

| | | | |
|---|---|---|---|
| 6,837,995 | B1 | 1/2005 | Vassarotti et al. |
| 7,166,443 | B2 | 1/2007 | Walker et al. |
| 8,332,160 | B1 | 12/2012 | Platt et al. |
| 8,697,359 | B1 | 4/2014 | Zhang et al. |
| 8,926,977 | B2 | 1/2015 | Miller et al. |
| 9,260,505 | B2 | 2/2016 | Weir et al. |
| 9,361,427 | B2 | 6/2016 | Hillson |
| 9,499,855 | B2 | 11/2016 | Hyde et al. |
| 9,776,138 | B2 | 10/2017 | Innings et al. |
| 9,790,490 | B2 | 10/2017 | Zhang et al. |
| 9,896,696 | B2 | 2/2018 | Begemann et al. |
| 9,982,279 | B1 | 5/2018 | Gill et al. |
| 9,988,624 | B2 | 6/2018 | Serber et al. |
| 10,017,760 | B2 | 7/2018 | Gill et al. |
| 10,266,851 | B2 | 4/2019 | Chen |
| 2002/0139741 | A1 | 10/2002 | Kopf |
| 2004/0110253 | A1 | 6/2004 | Kappler et al. |
| 2010/0076057 | A1 | 3/2010 | Sontheimer et al. |
| 2014/0068797 | A1 | 3/2014 | Doudna et al. |
| 2014/0199767 | A1 | 7/2014 | Barrangou et al. |
| 2014/0273226 | A1 | 9/2014 | Wu et al. |
| 2015/0098954 | A1 | 4/2015 | Hyde et al. |
| 2015/0159174 | A1 | 6/2015 | Frendewey et al. |
| 2015/0176013 | A1 | 6/2015 | Musunuru et al. |
| 2015/0191719 | A1 | 7/2015 | Hudson et al. |
| 2016/0024529 | A1 | 1/2016 | Carstens et al. |
| 2016/0053272 | A1 | 2/2016 | Wurzel et al. |
| 2016/0053304 | A1 | 2/2016 | Wurzel et al. |
| 2016/0076093 | A1 | 3/2016 | Shendure et al. |
| 2016/0102322 | A1 | 4/2016 | Ravinder et al. |
| 2016/0168592 | A1 | 6/2016 | Church et al. |
| 2016/0289673 | A1 | 10/2016 | Huang et al. |
| 2016/0298134 | A1 | 10/2016 | Chen et al. |
| 2017/0002339 | A1 | 1/2017 | Barrngou et al. |
| 2017/0051310 | A1 | 2/2017 | Doudna et al. |
| 2017/0073705 | A1 | 3/2017 | Chen et al. |
| 2017/0191123 | A1 | 7/2017 | Kim et al. |
| 2017/0240922 | A1 | 8/2017 | Gill et al. |
| 2018/0028567 | A1 | 2/2018 | Li et al. |
| 2018/0052176 | A1 | 2/2018 | Holt et al. |
| 2018/0073013 | A1 | 3/2018 | Lorenz et al. |
| 2018/0112235 | A1 | 4/2018 | Li et al. |
| 2018/0230460 | A1 | 8/2018 | Gill et al. |
| 2019/0017072 | A1 | 1/2019 | Ditommaso et al. |
| 2019/0169605 | A1 | 6/2019 | Masquelier et al. |

FOREIGN PATENT DOCUMENTS

| | | |
|---|---|---|
| EP | 2395087 | 12/2011 |
| WO | WO 2003/087341 | 10/2003 |
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO 2014/144495 | 9/2014 |
| WO | WO 2017/053902 | 3/2017 |
| WO | WO 2017/078631 | 5/2017 |
| WO | WO 2017/083722 | 5/2017 |
| WO | WO 2017/161371 | 9/2017 |
| WO | WO 2017/174329 | 10/2017 |
| WO | WO 2017/186718 | 11/2017 |
| WO | WO 2018/031950 | 2/2018 |
| WO | WO 2018/083339 | 5/2018 |
| WO | WO 2018/191715 | 10/2018 |

OTHER PUBLICATIONS

Bao, et al., "Genome-scale engineering of *Saccharomyces cerevisiae* with single-nucleotide precision", Nature Biotechnology, doi:10.1038/nbt.4132, pp. 1-6 (May 7, 2018).

Dicarlo, et al., "Genome engineering in *Saccharomyces cervisiae* using CRISPR-Case systems", Nucleic Acids Research, 41(7):4336-43 (2013).

Garst, et al., "Genome-wide mapping of mutations at single-nucleotide resolution for protein, metabolic and genome engineering", Nature Biotechnology, 35(1):48-59 (2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems", Nature Biotechnology, 31(3):233-41 (2013).

Jinek, et al., "A Programmable Dual-RNA-Guided DNA Endonuclease in Adaptive Bacterial Immunity", Science, 337:816-20 (2012).

Verwaal, et al., "CRISPR/Cpfl enables fast and simple genome editing of *Saccharamyces cerevisiae*", Yeast, 35:201-11 (2018).

Lian, et al., "Combinatorial metabolic engineering using an orthogonal tri-functional CRISPR system", Nature Communications, 8, 1688 (2017).

(Continued)

*Primary Examiner* — Tekchand Saidha

(74) *Attorney, Agent, or Firm* — Sarah Brashears; Dianna L. DeVore

(57) ABSTRACT

The present disclosure provides engineered RNA-guided enzymes for editing live cells.

14 Claims, 17 Drawing Sheets

Specification includes a Sequence Listing.

(56) References Cited

OTHER PUBLICATIONS

Roy, et cl., "Multiplexed precision genome editing with trackable genomic barcodes in yeast", Nature Biotechnolgy, doi:10.1038/nbt. 4137, pp. 1-16 (2018).
Dong, "Establishment of a highly efficient virus-inducible CRISPR/Cas9 system in insect cells,"Antiviral Res., 130:50-7(2016).
Epinat et al., "A novel engineered meganuclease induces homologous recombination in eukaryotic cells, e.g., yeast and mammalian cells", Nucleic Acids Research, 31(11): 2952-2962.
Farasat et al., "A Biophysical Model of CRISPR/Cas9 Activity for Rational Design of Genome Editing and Gene Regulation," PLoS Comput Biol., 29:12(1):e1004724 (2016).
Liu et al., "A chemical-inducible CRISPR-Cas9 system for rapid control of genome editing", Nature Chemical Biology, 12:980-987(2016).
Eklund, et al., "Altered target site specificity variants of the I-Ppol His-Cys bis homing endonuclease" Nucleic Acids Research, 35(17):5839-50 (2007).
Boles, et al., "Digital-to-biological converter for on-demand production of biologics", Nature Biotechnology, doi:10.1038/nbt.3859 (May 29, 2017).
Pines, et al., "Codon Compression Algorithms for Saturation Mutagenesis", ACS Synthetic Biology, 4:604-14 (2015).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Durai et al., "Zinc finger nucleases: custom-designed molecular scissors for genome engineering of plant and mammalian cells", Nucleic Acids Res., 33(18):5978-90 (2005).
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20 (1): 81-9 (2009).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Shivange, "Advances in generating functional diversity for directed protein evolution", Current Opinion in Chemical Biology, 12 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US2018/053671, dated Nov. 23, 2018, p. 1-12.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.

US 10,640,754 B1

ENGINEERED ENZYMES

RELATED APPLICATIONS

This application is a continuation of U.S. Ser. No. 16/658,948, filed 21 Oct. 2019, which claims priority to U.S. Provisional Application No. 62/748,668, filed 22 Oct. 2018.

FIELD OF THE INVENTION

This invention relates to engineered enzymes for editing live cells.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently, various nucleases have been identified that allow manipulation of gene sequence, and hence gene function. These nucleases include nucleic acid-guided nucleases. The range of target sequences that nucleic acid-guided nucleases can recognize, however, is constrained by the need for a specific protospacer adjacent motif (PAM) to be located near the desired target sequence. PAMs are short nucleotide sequences recognized by a gRNA/nuclease complex, where this complex directs editing of a target sequence in a live cell. The precise PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of nucleic acid-guided nucleases may allow for alteration of PAM preference, allow for editing optimization in different organisms and/or alter enzyme fidelity; all changes that may increase the versatility of a specific nucleic acid-guided nuclease for certain editing tasks.

There is thus a need in the art of nucleic acid-guided nuclease gene editing for improved nucleases. The engineered MAD70-series nucleases described herein satisfy this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides engineered MAD70-series nucleases with varied PAM preferences, varied editing efficiency in different organisms and/or altered RNA-guided enzyme fidelity (e.g., decreased off-target cutting).

Thus, in one embodiment there is provided an engineered MAD70-series nuclease with an altered RNA-guided enzyme fidelity relative to the MAD7 nuclease where the MAD7 nuclease has the amino acid sequence of SEQ ID No. 1. In some aspects of this embodiment, the engineered MAD70-series nuclease with the higher altered RNA-guided enzyme fidelity comprises any of SEQ ID No. 4-7.

In other embodiments there is provided an engineered MAD70-series nuclease having a PAM preference different than the MAD7 nuclease having the sequence of SEQ ID No. 1. In some aspects of this embodiment, the engineered MAD70-series nuclease having an altered PAM preference comprises any of SEQ ID Nos. 2, 3, 11, 12, 13, 14, 67 or 68. In some aspects of this embodiment, there is provided a cocktail of nuclease enzymes comprising one, two, three, four, five or all of SEQ ID Nos. 2, 3, 11, 12, 13, 14, 67 or 68, and in some aspects, there is provided a cocktail of nuclease enzymes comprising one, some or all of SEQ ID Nos. 2, 3, 11, 12, 13, 14, 67 or 68 and another nuclease with a PAM preference different from SEQ ID Nos. 2, 3, 11, 12, 13, 14, 67 or 68, and in some aspects, the other nuclease has a sequence of SEQ ID No. 4, 5, 6, 7, 69-78 or 79-86.

Additionally, there is provided is an engineered MAD70-series nuclease with lower cutting activity relative to the MAD7 nuclease having the sequence of SEQ ID No. 1. In some aspects of this embodiment, the engineered MAD70-series nuclease having lowered cutting activity comprises any of SEQ ID Nos. 8-10 or 15.

Also there is provided an engineered MAD70-series nuclease with enhanced editing efficiency in yeast comprising any of SEQ ID Nos. 69-78 and 79-86.

These aspects and other features and advantages of the invention are described below in more detail.

BRIEF DESCRIPTION OF THE FIGURES

FIG. 2A is the plot (sum of PAM depletion vs. pos9_score) for the MAD7 nuclease having the sequence SEQ ID NO. 1, and FIG. 2B is the plot for the screened 1104 single amino acid variants.

DETAILED DESCRIPTION

Figure 1A:
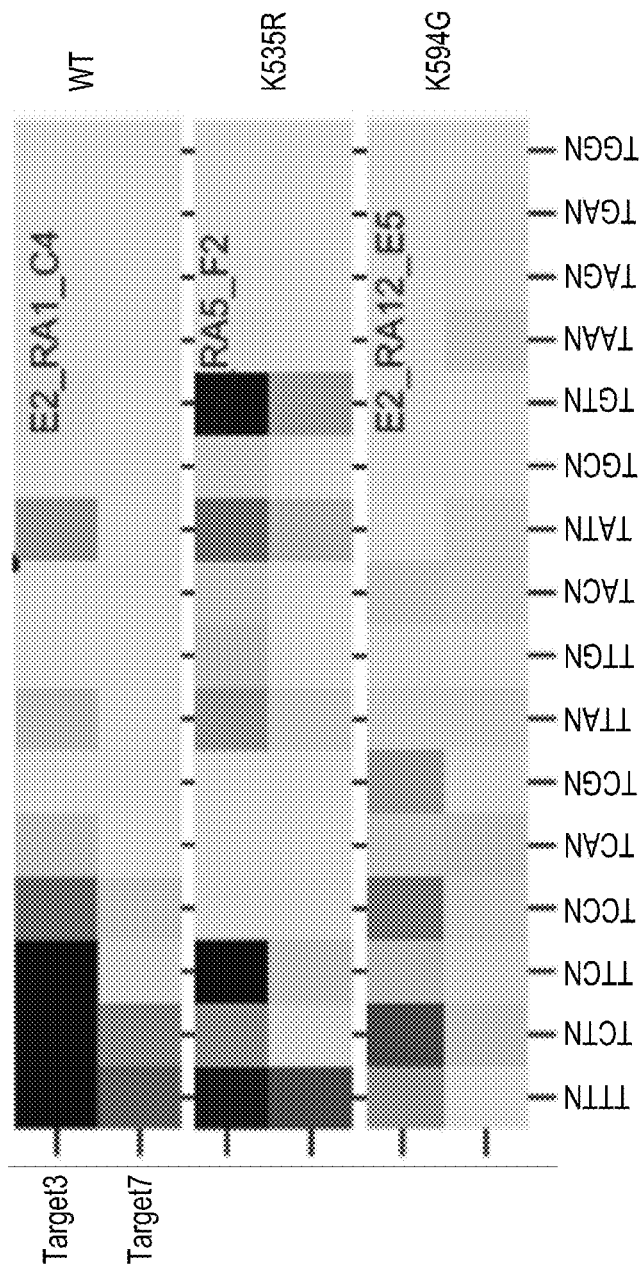
FIG. 1A is a heatmap for certain of the MAD70-series nucleases with different PAM recognition sites.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities. Moreover, all of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry, biological emulsion generation, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*" 1984, IRL Press, London; Nelson and Cox (2000), *Lehninger, Principles of Biochemistry* 3$^{rd}$ Ed., W. H. Freeman Pub., New York, N.Y.; Berg et al. (2002) *Biochemistry*, 5$^{th}$ Ed., W.H. Freeman Pub., New York, N.Y.; *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011); Essential Stem Cell Methods, (Lanza and Klimanskaya, eds., Academic Press 2011), all of which are herein incorporated in their entirety by reference for all purposes. Nuclease-specific techniques can be found in, e.g., *Genome Editing and Engineering From TALENs and CRISPRs to Molecular Surgery*, Appasani and Church, 2018; and *CRISPR: Methods and Protocols*, Lindgren and Charpentier, 2015; both of which are herein incorporated in their entirety by reference for all purposes. Basic methods for enzyme engineering may be found in, *Enzyme Engineering Methods and Protocols*, Samuelson, ed., 2013; *Protein Engineering*, Kaumaya, ed., (2012); and Kaur and Sharma, "Directed Evolution: An Approach to Engineer Enzymes", Crit. Rev. Biotechnology, 26:165-69 (2006).

Note that as used herein and in the appended claims, the singular forms "a," "an," and "the" include plural referents unless the context clearly dictates otherwise. Thus, for example, reference to "an oligonucleotide" refers to one or more oligonucleotides, and reference to "an automated system" includes reference to equivalent steps and methods for use with the system known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, well-known features and procedures well known to those skilled in the art have not been described in order to avoid obscuring the invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TTAGCTGG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to nucleic acid that is designed to introduce a DNA sequence modification (insertion, deletion, substitution) into a locus by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell-will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible and, in some embodiments—particularly many embodiments in which selection is employed—the transcription of at least one component of the nucleic acid-guided nuclease editing system is under the control of an inducible promoter.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, rhamnose, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2a; detectable by Mab-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" refer to any locus in vitro or in vivo, or in a nucleic acid (e.g., genome) of a cell or population of cells, in which a change of at least one nucleotide is desired using a nucleic acid-guided nuclease editing system. The target sequence can be a genomic locus or extrachromosomal locus.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. As used herein, the phrase "engine vector" comprises a coding sequence for a nuclease to be used in the nucleic acid-guided nuclease systems and methods of the present disclosure. The engine vector may also comprise, in a bacterial system, the λ Red recombineering system or an equivalent thereto. Engine vectors also typically comprise a selectable marker. As used herein the phrase "editing vector" comprises a donor nucleic acid, optionally including an alteration to the target sequence that prevents nuclease binding at a PAM or spacer in the target sequence after editing has taken place, and a coding sequence for a gRNA. The editing vector may also comprise a selectable marker and/or a barcode. In some embodiments, the engine vector and editing vector may be combined; that is, the contents of the engine vector may be found on the editing vector. Further, the engine and editing vectors comprise control sequences operably linked to, e.g., the nuclease coding sequence, recombineering system coding sequences (if present), donor nucleic acid, guide nucleic acid, and selectable marker(s).

Editing in Nucleic Acid-Guided Nuclease Genome Systems Generally

The present disclosure provides engineered gene editing MAD70-series nucleases with varied PAM preferences, optimized editing efficiency in different organisms, and/or an altered RNA-guided enzyme fidelity. The engineered MAD70-series nucleases may be used to edit all cell types including, archaeal, prokaryotic, and eukaryotic (e.g., yeast, fungal, plant and animal) cells although certain MAD70-series variants exhibit enhanced efficiency in, e.g., yeast or mammalian cells.

The engineered MAD70-series nuclease variants described herein improve RNA-guided enzyme editing systems in which nucleic acid-guided nucleases (e.g., RNA-guided nucleases) are used to edit specific target regions in an organism's genome. A nucleic acid-guided nuclease complexed with an appropriate synthetic guide nucleic acid in a cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby.

The engineered MAD70-series nucleases may be delivered to cells to be edited as a polypeptide; alternatively, a polynucleotide sequence encoding the engineered MAD70-series nuclease(s) is transformed or transfected into the cells to be edited. The polynucleotide sequence encoding the engineered MAD70-series nuclease may be codon optimized for expression in particular cells, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of the engineered MAD70-series nuclease to be employed depends on many factors, such as what type of edit is to be made in the target sequence and whether an appropriate PAM is located close to the desired target sequence. The engineered MAD70-series nuclease may be encoded by a DNA sequence on a vector (e.g., the engine vector) and be under the control of a constitutive or inducible promoter. In some embodiments, the sequence encoding the nuclease is under the control of an inducible promoter, and the inducible promoter may be separate from but the same as an inducible promoter controlling transcription of the guide nucleic acid; that is, a separate inducible promoter may drive the transcription of the nuclease and guide nucleic acid sequences but the two inducible promoters may be the same type of inducible promoter. Alternatively, the inducible promoter controlling expression of the nuclease may be different from the inducible promoter controlling transcription of the guide nucleic acid.

In general, a guide nucleic acid (e.g., gRNA) complexes with a compatible nucleic acid-guided nuclease and can then hybridize with a target sequence, thereby directing the nuclease to the target sequence. In certain aspects, the RNA-guided enzyme editing system may use two separate guide nucleic acid molecules that combine to function as a guide nucleic acid, e.g., a CRISPR RNA (crRNA) and trans-activating CRISPR RNA (tracrRNA). In other aspects—and used with the MAD70-series variant nucleases described herein—the guide nucleic acid may be a single guide nucleic acid that includes both the crRNA and tracrRNA sequences. A guide nucleic acid can be DNA or RNA; alternatively, a guide nucleic acid may comprise both DNA and RNA. In some embodiments, a guide nucleic acid may comprise modified or non-naturally occurring nucleotides. In cases where the guide nucleic acid comprises RNA, the gRNA may be encoded by a DNA sequence on a polynucleotide molecule such as a plasmid, linear construct, or the coding sequence may reside within an editing cassette and is under the control of a constitutive promoter, or, in some embodiments, an inducible promoter as described below.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and compositions, the guide nucleic acid typically is provided as a sequence to be expressed from a plasmid or vector and comprises both the guide sequence and the scaffold sequence as a single transcript under the control of a promoter, and in some embodiments, an inducible promoter. The guide nucleic acid can be engineered to target a desired target sequence by altering the guide sequence so that the guide sequence is complementary to a desired target sequence, thereby allowing hybridization between the guide sequence and the target sequence. In general, to generate an edit in the target sequence, the gRNA/nuclease complex binds to a target sequence as determined by the guide RNA, and the nuclease recognizes a protospacer adjacent motif (PAM) sequence adjacent to the target sequence. The target sequence can be any polynucleotide endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) or a non-coding sequence (e.g., a regulatory polynucleotide, an intron, a PAM, or "junk" DNA).

The guide nucleic acid may be part of an editing cassette that encodes the donor nucleic acid, such as described in U.S. U.S. Pat. No. 10,240,167, issued 26 Mar. 2019; U.S. Pat. No. 10,266,849, issued 23 Apr. 2019; U.S. Pat. No. 9,982,278, issued 22 Jun. 2018; U.S. Pat. No. 10,351,877, issued 15 Jul. 2019; and U.S. Pat. No. 10,362,422, issued 30 Jul. 2019; and U.S. Ser. No. 16/275,439, filed 14 Feb. 2019; Ser. No. 16/275,465, filed 14 Feb. 2019; Ser. No. 16/550,092, filed 23 Aug. 2019; and Ser. No. 16/552,517, filed 26 Aug. 2019. Alternatively, the guide nucleic acid may not be part of the editing cassette and instead may be encoded on the engine or editing vector backbone. For example, a sequence coding for a guide nucleic acid can be assembled or inserted into a vector backbone first, followed by insertion of the donor nucleic acid in, e.g., the editing cassette. In other cases, the donor nucleic acid in, e.g., an editing cassette can be inserted or assembled into a vector backbone first, followed by insertion of the sequence coding for the guide nucleic acid. In yet other cases, the sequence encoding the guide nucleic acid and the donor nucleic acid (inserted, for example, in an editing cassette) are simultaneously but separately inserted or assembled into a vector. In yet other embodiments, the sequence encoding the guide nucleic acid and the sequence encoding the donor nucleic acid are both included in the editing cassette.

The target sequence is associated with a PAM, which is a short nucleotide sequence recognized by the gRNA/nuclease complex. The precise PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve fidelity, or decrease fidelity. In certain embodiments, the genome editing of a target sequence both introduces a desired DNA change to a target sequence, e.g., the genomic DNA of a cell, and removes, mutates, or renders inactive a proto-spacer mutation (PAM) region in the target sequence. Rendering the PAM at the target sequence inactive precludes additional editing of the cell genome at that target sequence, e.g., upon subsequent exposure to a nucleic acid-guided nuclease complexed with a synthetic guide nucleic acid in later rounds of editing. Thus, cells having the desired target sequence edit and an altered PAM can be selected using a nucleic acid-guided nuclease complexed with a synthetic guide nucleic acid complementary to the target sequence. Cells that did not undergo the first editing event will be cut rendering a double-stranded DNA break, and thus will not continue to be viable. The cells containing the desired target sequence edit and PAM alteration will not be cut, as these edited cells no longer contain the necessary PAM site and will continue to grow and propagate.

The range of target sequences that nucleic acid-guided nucleases can recognize is constrained by the need for a specific PAM to be located near the desired target sequence. As a result, it often can be difficult to target edits with the precision that is necessary for genome editing. It has been found that nucleases can recognize some PAMs very well (e.g., canonical PAMs), and other PAMs less well or poorly (e.g., non-canonical PAMs). Because certain of the engineered MAD70-series nucleases disclosed herein recognize different PAMs, the engineered MAD70-series nucleases increase the number of target sequences that can be targeted for editing; that is, engineered MAD70-series nucleases decrease the regions of "PAM deserts" in the genome. Thus, the engineered MAD70-series nucleases expand the scope of target sequences that may be edited by increasing the number (variety) of PAM sequences recognized. Moreover, cocktails of engineered MAD70-series nucleases may be delivered to cells such that target sequences adjacent to several different PAMs may be edited in a single editing run.

Another component of the nucleic acid-guided nuclease system is the donor nucleic acid. In some embodiments, the donor nucleic acid is on the same polynucleotide (e.g., editing vector or editing cassette) as the guide nucleic acid and may be (but not necessarily) under the control of the same promoter as the guide nucleic acid (e.g., a single promoter driving the transcription of both the guide nucleic acid and the donor nucleic acid). The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 20, 25, 30, 35, 40, 50, 60, 70, 80, 90 or more nucleotides. In many embodiments, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

As mentioned previously, often the donor nucleic acid is provided as an editing cassette, which is inserted into a vector backbone where the vector backbone may comprise a promoter driving transcription of the gRNA and the coding sequence of the gRNA, or the vector backbone may comprise a promoter driving the transcription of the gRNA but not the gRNA itself. Moreover, there may be more than one, e.g., two, three, four, or more guide nucleic acid/donor nucleic acid cassettes inserted into an engine vector, where each guide nucleic acid is under the control of separate different promoters, separate like promoters, or where all guide nucleic acid/donor nucleic acid pairs are under the control of a single promoter. In some embodiments—such as embodiments where cell selection is employed—the promoter driving transcription of the gRNA and the donor nucleic acid (or driving more than one gRNA/donor nucleic acid pair) is an inducible promoter. Inducible editing is advantageous in that singulated cells can be grown for several to many cell doublings before editing is initiated, which increases the likelihood that cells with edits will survive, as the double-strand cuts caused by active editing are largely toxic to the cells. This toxicity results both in cell death in the edited colonies, as well as a lag in growth for the edited cells that do survive but must repair and recover following editing. However, once the edited cells have a chance to recover, the size of the colonies of the edited cells will eventually catch up to the size of the colonies of unedited cells. See, e.g., U.S. Ser. No. 16/399,988, filed 30 Apr. 2019; Ser. No. 16/454,865 filed 26 Jun. 2019; and Ser. No. 16/540,606, filed 14 Aug. 2019. Further, a guide nucleic acid may be efficacious directing the edit of more than one donor nucleic acid in an editing cassette; e.g., if the desired edits are close to one another in a target sequence.

In addition to the donor nucleic acid, an editing cassette may comprise one or more primer sites. The primer sites can be used to amplify the editing cassette by using oligonucleotide primers; for example, if the primer sites flank one or more of the other components of the editing cassette.

Also, as described above, the donor nucleic acid may comprise—in addition to the at least one mutation relative to a target sequence—one or more PAM sequence alterations that mutate, delete or render inactive the PAM site in the target sequence. The PAM sequence alteration in the target sequence renders the PAM site "immune" to the nucleic acid-guided nuclease and protects the target sequence from further editing in subsequent rounds of editing if the same nuclease is used.

In addition, the editing cassette may comprise a barcode. A barcode is a unique DNA sequence that corresponds to the donor DNA sequence such that the barcode can identify the edit made to the corresponding target sequence. The barcode typically comprises four or more nucleotides. In some embodiments, the editing cassettes comprise a collection of donor nucleic acids representing, e.g., gene-wide or genome-wide libraries of donor nucleic acids. The library of editing cassettes is cloned into vector backbones where, e.g., each different donor nucleic acid is associated with a different barcode.

Additionally, in some embodiments, an expression vector or cassette encoding components of the nucleic acid-guided nuclease system further encodes an engineered MAD70-series nuclease comprising one or more nuclear localization sequences (NLSs), such as about or more than about 1, 2, 3, 4, 5, 6, 7, 8, 9, 10, or more NLSs. In some embodiments, the engineered nuclease comprises NLSs at or near the amino-terminus, NLSs at or near the carboxy-terminus, or a combination.

The engine and editing vectors comprise control sequences operably linked to the component sequences to be transcribed. As stated above, the promoters driving transcription of one or more components of the engineered MAD70-series nuclease editing system may be inducible, and an inducible system is likely employed if selection is to be performed. A number of gene regulation control systems have been developed for the controlled expression of genes in plant, microbe, and animal cells, including mammalian cells, including the pL promoter (induced by heat inactivation of the CI857 repressor), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12):5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080, the ecdysone-inducible gene expression system (No et al., PNAS, 93(8): 3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others.

Typically, performing genome editing in live cells entails transforming cells with the components necessary to perform nucleic acid-guided nuclease editing. For example, the cells may be transformed simultaneously with separate engine and editing vectors; the cells may already be expressing the engineered MAD70-series nuclease (e.g., the cells may have already been transformed with an engine vector or the coding sequence for the engineered MAD70-series nuclease may be stably integrated into the cellular genome) such that only the editing vector needs to be transformed into the cells; or the cells may be transformed with a single vector comprising all components required to perform nucleic acid-guided nuclease genome editing.

A variety of delivery systems can be used to introduce (e.g., transform or transfect) nucleic acid-guided nuclease editing system components into a host cell. These delivery systems include the use of yeast systems, lipofection systems, microinjection systems, biolistic systems, virosomes, liposomes, immunoliposomes, polycations, lipid:nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of particular interest is the use of electroporation, particularly flow-through electroporation (either as a stand-alone instrument or as a module in an automated multi-module system) as described in, e.g., U.S. U.S. Pat. No. 10,435,717, issued 8 Oct. 2019; and U.S. Pat. No. 10,443,074, issued 15 Oct. 2019; U.S. Ser. No. 16/550,790, filed 26 Aug. 2019; Ser. No. 10/323,258, issued 18 Jun. 2019; and Ser. No. 10/415,058, issued 17 Sep. 2019.

After the cells are transformed with the components necessary to perform nucleic acid-guided nuclease editing, the cells are cultured under conditions that promote editing. For example, if constitutive promoters are used to drive transcription of the engineered MAD70-series nucleases and/or gRNA, the transformed cells need only be cultured in a typical culture medium under typical conditions (e.g., temperature, $CO_2$ atmosphere, etc.) Alternatively, if editing is inducible—by, e.g., activating inducible promoters that control transcription of one or more of the components needed for nucleic acid-guided nuclease editing, such as, e.g., transcription of the gRNA, donor DNA, nuclease, or, in the case of bacteria, a recombineering system—the cells are subjected to inducing conditions. The MAD70 nucleases described herein may be used in automated systems, such as those described in U.S. Pat. No. 10,253,316, issued 9 Apr. 2019; U.S. Pat. No. 10,329,559, issued 25 Jun. 2019; U.S. Pat. No. 10,323,242, issued 18 Jun. 2019; and U.S. Pat. No. 10,421,959, issued 24 Sep. 2019; and U.S. patent Ser. No. 16/412,195, filed 14 May 2019; Ser. No. 16/423,289, filed 28 May 2019; and Ser. No. 16/571,091, filed 14 Sep. 2019.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Exemplary Workflow Overview

Figure 3:
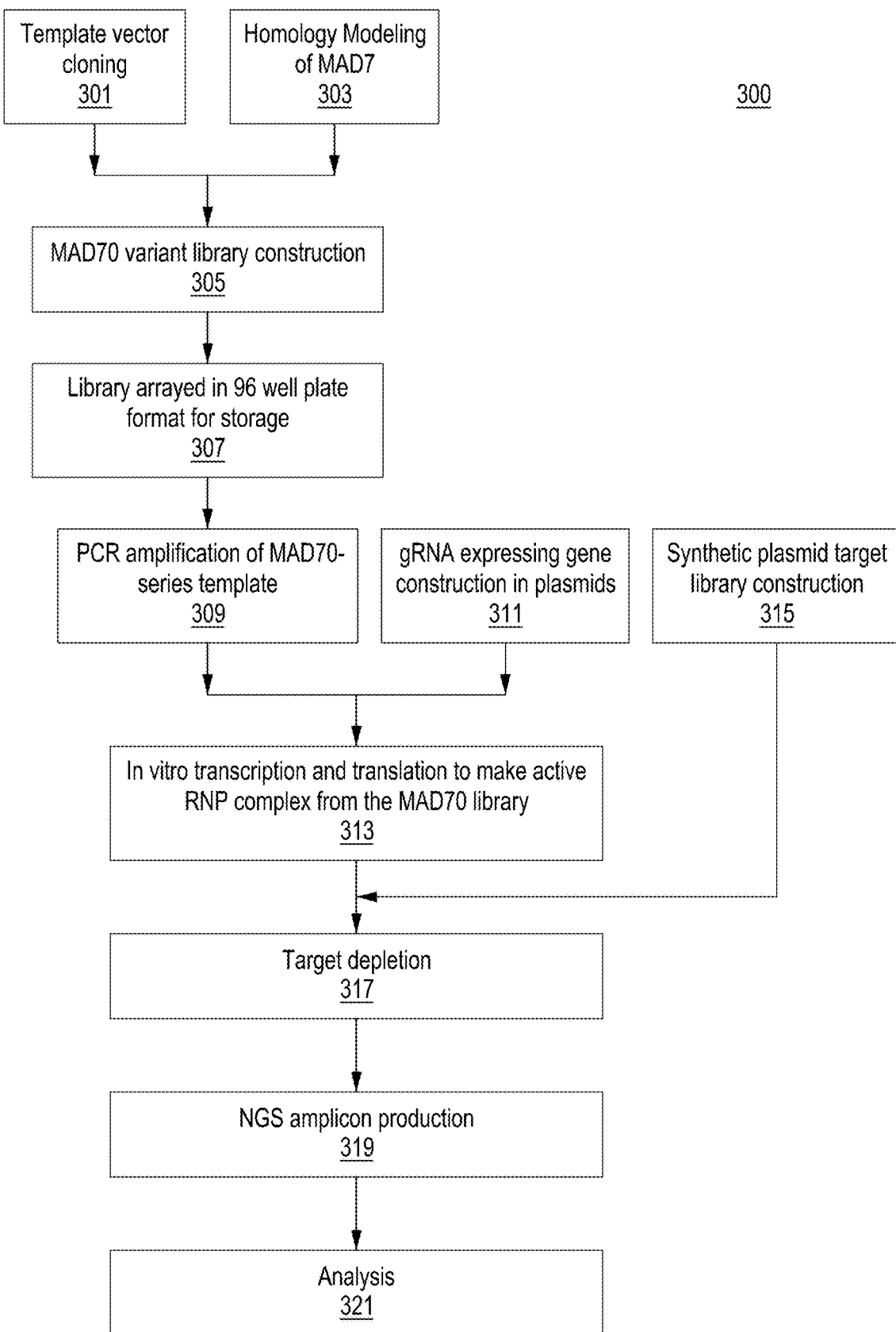
FIG. 3 is an exemplary workflow for creating and screening engineered MAD70-series enzymes.

FIG. 3 shows an exemplary workflow 300 for creating and screening engineered MAD70-series enzymes. In a first step 301, a wild type MAD7 DNA sequence was prepared and cloned to make a template vector for creation of MAD70-series variants. In another step 303, computer homology modeling of MAD7 (represented by an amino acid sequence having the sequence SEQ ID No. 1) was performed to identify putative regions of interest for rationally-designing MAD70 variants with varied PAM preferences, optimized activity in specific organisms, and altered fidelity as compared to MAD7. These regions include regions of the nuclease proximal to key regions where it is predicted that the nuclease interacts with the PAM, target, or gRNA e.g., see Example 2 below. Once putative key regions of interest were identified in silico, cassettes were constructed and cloned into the vector template, then transformed into cells 305, thereby generating a library of engineered MAD70-series variants. The cells transformed with the engineered MAD70-series variants were arrayed in 96-well plates 307 for storage. At step 309, an aliquot of the cells from each well was taken, and the MAD70-series sequences were amplified from each aliquot. At another step 311, a plasmid expressing a gRNA was constructed, and then combined with the amplified MAD70-series nucleases to perform in vitro transcription and translation to make active ribonuclease protein complexes 313. A synthetic target library was constructed 315, in which to test target depletion 317 for each of that MAD70-series variants. After target depletion, amplicons were produced for analysis using next-gen sequencing 319, and sequencing data analysis was performed 321 to determine target depletion.

Example 2: Homology Modeling and Positions for Mutation Testing

An in silico homology model of a MAD7 enzyme having the amino acid sequence as represented by SEQ ID No. 1 was made using PDB:5B43 structure as a template using SWISS-MODEL (https://swissmodel.expasy.org/). Mutation sets were generated based on residue proximity to putative key regions of where the nuclease is predicted to interact with the PAM site, target, or gRNA, as well as targeting charged amino acids. The following amino acid residues were targeted for mutation (the residues are in relation to the MAD7 amino acid sequence in SEQ ID No. 1): 19, 22, 55, 84, 95, 124, 125, 159, 160, 161, 162, 165, 169, 171, 187, 269, 278, 281, 283, 284, 346, 466, 505, 511, 517, 528, 529, 530, 531, 532, 533, 534, 535, 536, 539, 582, 584, 586, 587, 588, 589, 590, 591, 593, 594, 595, 596, 597, 598, 599, 600, 601, 620, 623, 650, 707, 712, 720, 739, 741, 742, 743, 749, 761, 768, 785, 786, 822, 830, 833, 842, 853, 878, 881, 912, 920, 924, 925, 932, 934, 937, 946, 969, 970, 974, 982, 990, 997, 1019, 1021, 1052, 1054, 1109, 1111, 1113, 1173.

Example 3: Vector Cloning, MAD70-Series Variant Library Construction and PCR

The MAD7 coding sequence was cloned into a pUC57 vector with T7-promoter sequence attached to the 5'-end of the coding sequence and a T7-terminator sequence attached to the 3'-end of the coding sequence. Next, using a pUC57-MAD7 wildtype vector as a template, a saturated mutation library for the 96 positions predicted by the modeling described in Example 2 was made substituting the original codon with NNK (IUPAC code for DNA: N=A, T, G, C; K=G, T) randomized codons. The engineered MAD70-series variants were delivered as a pool of mutant plasmids. 100 ng of a plasmid mixture was transformed into five E.cloni® SUPREME electrocompetent solo cells (Lucigen). After the cells were recovered in 5 mL of recovery medium at 37° C. for 1 hr in a shaking incubator, 1 mL of 50% glycerol was added and the cells were stored at −80° C. as 100 µL aliquots.

The stored cells were diluted in phosphate buffered saline and spread on LB agar plates with 100 µg/mL of carbenicillin. The cells were then grown overnight at 37° C. in an incubator. Colonies were picked and inoculated into 1 mL of LB medium (100 µg/mL of carbenicillin) in 96-well culture blocks. Cultures were grown overnight in a shaking incubator at 37° C. Next, 1 µL of the cells were diluted into 500 µL of PCR grade water, and 25 µl aliquots of diluted cultures were boiled for 5 min at 95° C. using a thermal cycler. The boiled cells were used to PCR amplify the different engineered MAD70-series variant coding sequences. The rest of the cultures were stored at −80° C. with added glycerol at 10% v/v concentration.

First, Q5 Hot Start 2× master mix reagent (NEB) was used to amplify the engineered MAD70-series variant sequences using the boiled cells as a source of MAD70-series variant templates. The forward primer 5'-TTGGGTAACGCCA-GGGTTTT (SEQ ID No. 16) and reverse primer 5'-TGT-GTGGAATTGTGAGCGGA (SEQ ID No. 17) amplified the sequences flanking the engineered MAD70-series variant in the pUC57 vector including the T7-promoter and T7-terminator components attached to the MAD7 variant sequence at the 5'- and 3'-end of the engineered MAD70-series variants, respectively. 1 µM primers were used in a 10 µL PCR reaction using 3.3 µL boiled cell samples as templates in 96 well PCR plates. The PCR conditions shown in Table 1 were used:

TABLE 1

| PCR conditions | | |
|---|---|---|
| STEP | TEMPERATURE | TIME |
| DENATURATION | 98° C. | 30 SEC |
| 30 CYCLES | 98° C. | 10 SEC |
|  | 66° C. | 30 SEC |
|  | 72° C. | 2.5 MIN |
| FINAL EXTENSION | 72° C. | 2 MIN |
| HOLD | 12° C. |  |

Figure 4:
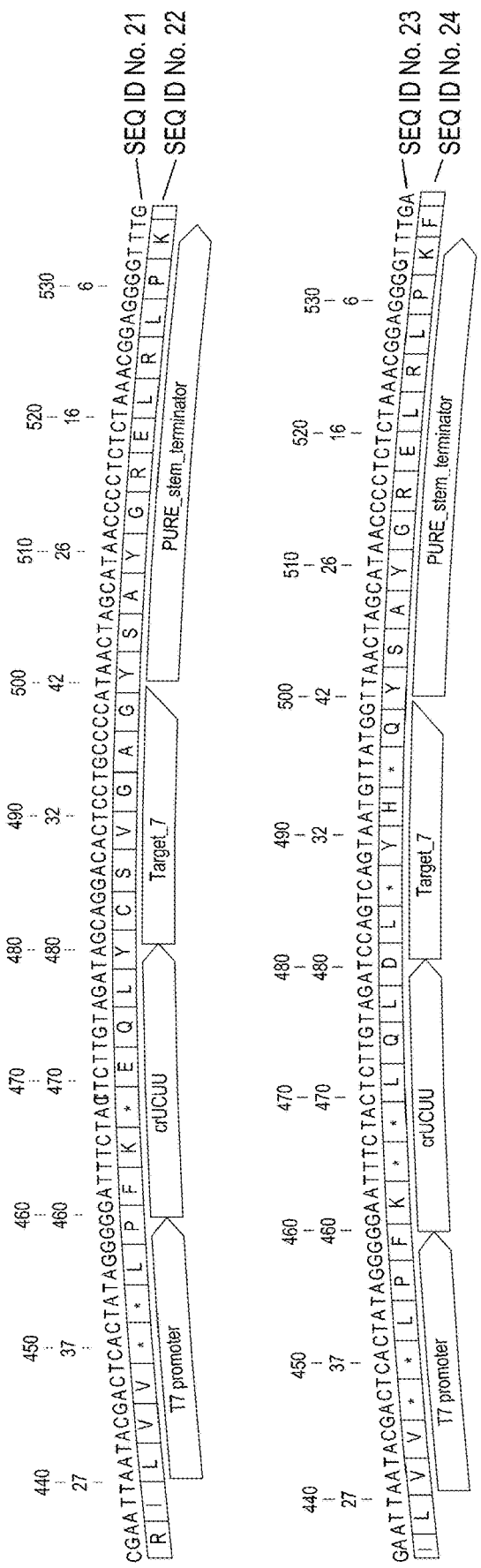
FIG. 4 shows the sequence of two different gRNA constructs used for depletion studies (SEQ ID No. 21-24).

Example 4: gRNA Expression Gene Construction in Plasmids and Synthetic Target Library Construction Two plasmids were made to produce two different guide RNAs for the in vitro depletion assay. A MAD7 gRNA scaffold sequence (5'-GGAATTTCTACTCTTGTAGAT (SEQ ID No. 18)) was placed under the control of the T7 promoter followed by a guide sequence for synthetic Target 3 or Target 7. The sequences of these constructs are shown in FIG. 4.

Two different synthetic target sequences were used to design a synthetic plasmid target library, where the target oligo pools were ordered from Twist Bioscience (Carlsbad, Calif.) using the following designs: Target sequence: Target3: 5'-CCAGTCAGTAATGTTACTGG (SEQ ID No. 19), and Target7: 5'-AGCAGGACACTCCTGCCCCA (SEQ ID No. 20).

TABLE 2

Target Library Design:

| TARGET LIBRARY | PAM 5' | 3' UMI | NUMBER OF PAMs FOR ANALYSIS | VARIANT/ DESIGN |
|---|---|---|---|---|
| PAM PANEL | TNNN | N | 64 | 1 |
| SPECIFICITY PANEL | TTTV | N | 3 | 12 |

The PAM panel library was designed by adding TNNN randomized sequences as the 5'-end PAM for each target, then by adding a single bp N at the end of the target to be used as the unique molecular identifier in the sequencing analysis. The specificity panel was designed by introducing 2 bp tandem mismatches in the following positions in each target: 1st, 3rd, 7th, 8th, 9th, 11th, 13th, 14th, 15th, 17th, 18th, and 19th bp. Each target with 2 bp mismatches was used to add 5'-end TTTV PAM (IUPAC nomenclature: V=A,G, or C) and 3'-end 1 bp N as the UMI (unique molecule identifier) for sequencing analysis. The target library was cloned into a pUC19 backbone and prepared using the Midi-plus™ plasmid preparation kit (Qiagen). The target library pool was prepared at 10 ng/µL final concentration.

Example 5: In Vitro Transcription and Translation for Production of MAD70-Series Nucleases and gRNAs in a Single Well A PURExpress® In Vitro Protein Synthesis Kit (NEB) was used to produce engineered MAD70-series variant proteins from the PCR-amplified MAD70-series variant library, and also to produce gRNAs for synthetic target Library of Target3 and Target7. In each well in a 96-well plate, the reagents in Table 3 were mixed to start the production of MAD7 variants and gRNA:

TABLE 3

Reagents

| | REAGENTS | VOLUME (µl) |
|---|---|---|
| 1 | SolA (NEB kit) | 3.3 |
| 2 | SolB (NEB kit) | 2.5 |
| 3 | gRNA mix (4 ng/µl stock) | 0.8 |
| 4 | Murine RNase inhibitor (NEB) | 0.2 |
| 5 | Water | 0.5 |
| 6 | PCR amplified T7 MAD70-series variants | 1.0 |

A master mix with all reagents was mixed on ice with the exception of the PCR-amplified T7-MAD70-series variants to cover enough 96-well plates for the assay. After 7.3 µL of the master mix was distributed in each well in 96 well plates, 1 µL of the PCR amplified MAD70-series variants under the control of T7 promoter was added. The 96-well plates were sealed and incubated for 4 hrs at 37° C. in a thermal cycler. The plates were kept at room temperature until the target pool was added to perform the target depletion reaction.

Example 6: Performing Target Depletion, PCR and NGS

After 4 hours incubation to allow production of the engineered MAD70-series variants and gRNAs, 4 µL of the target library pool (10 ng/µL) was added to the in vitro transcription/translation reaction mixture. After the target library was added, reaction mixtures were incubated overnight at 37° C. The target depletion reaction mixtures were diluted into PCR-grade water that contains RNAse A and then boiled for 5 min at 95° C. The mixtures were then amplified and sequenced. The PCR conditions in Table 4 below were used:

TABLE 4

PCR Conditions

| STEP | TEMPERATURE | TIME |
|---|---|---|
| DENATURATION | 98° C. | 30 SEC |
| 6 CYCLES | 98° C. | 10 SEC |
| | 61° C. | 30 SEC |
| | 72° C. | 10 SEC |
| 22 CYCLES | 98° C. | 10 SEC |
| | 72° C. | 10 SEC |
| FINAL EXTENSION | 72° C. | 2 MINUTES |
| HOLD | 12° C. | |

Example 7: Data Analysis

Table 5 is a table of amino acid substitutions made to the MAD7 nuclease amino acid sequence (SEQ ID No. 1) that result in MAD70-series variant nucleases with different PAM recognition sites as compared to the native MAD7 nuclease.

TABLE 5

MAD70-series Variants-Altered PAM Preference

| WT Residue | Mutation Detected | New PAMs, cut detected | SEQ ID No. |
|---|---|---|---|
| K535L | L | TGTN, TTCN | SEQ ID No. 2 |
| K535S | S | TGTN, TTCN | SEQ ID No. 11 |
| K535C | C | TGTN, TTCN | SEQ ID No. 12 |
| K535R | R | TGTN, TTCN | SEQ ID No. 13 |
| K535N | N | TGTN, TTCN | SEQ ID No. 14 |
| K535G | G | TCTN as primary | SEQ ID No. 3 |

FIG. 1A is a heatmap for the MAD70-series variant nucleases with different PAM recognition sites. The K535R mutation disrupts the ability of the enzyme to recognize TCTN PAMs and enhances the ability of the enzyme to recognize PAMs containing a purine at the second position (TATN/TGTN). The K594 mutation ablates the recognition of the preferred TTTN PAMs while enhancing TCGN recognition.

Table 6 is a table of amino acid substitutions made to the MAD7 nuclease amino acid sequence (SEQ ID No. 1) resulting in MAD70-series variant nucleases with varied targeting fidelity as compared to the MAD7 reference nuclease.

TABLE 6

MAD70-series Variants-Varied Target Fidelity

| WT Residue | Mutation Detected | Pos_9 score for HF-MAD7 (wt > 0.3) | SEQ ID No. |
|---|---|---|---|
| R920G | G | 0.0 | SEQ ID No. 4 |
| R924I | I | 0.04 | SEQ ID No. 5 |
| K511L | L | 0.03 | SEQ ID No. 6 |
| H283T | T | 0.01 | SEQ ID No. 7 |
| R187K | K | 0.0 | SEQ ID No. 8 |
| N589G | G | 0.0 | SEQ ID No. 9 |
| K281A | A | 0.04 | SEQ ID No. 10 |
| K281V | V | 0.01 | SEQ ID No. 15 |

Figures 1, 1B:
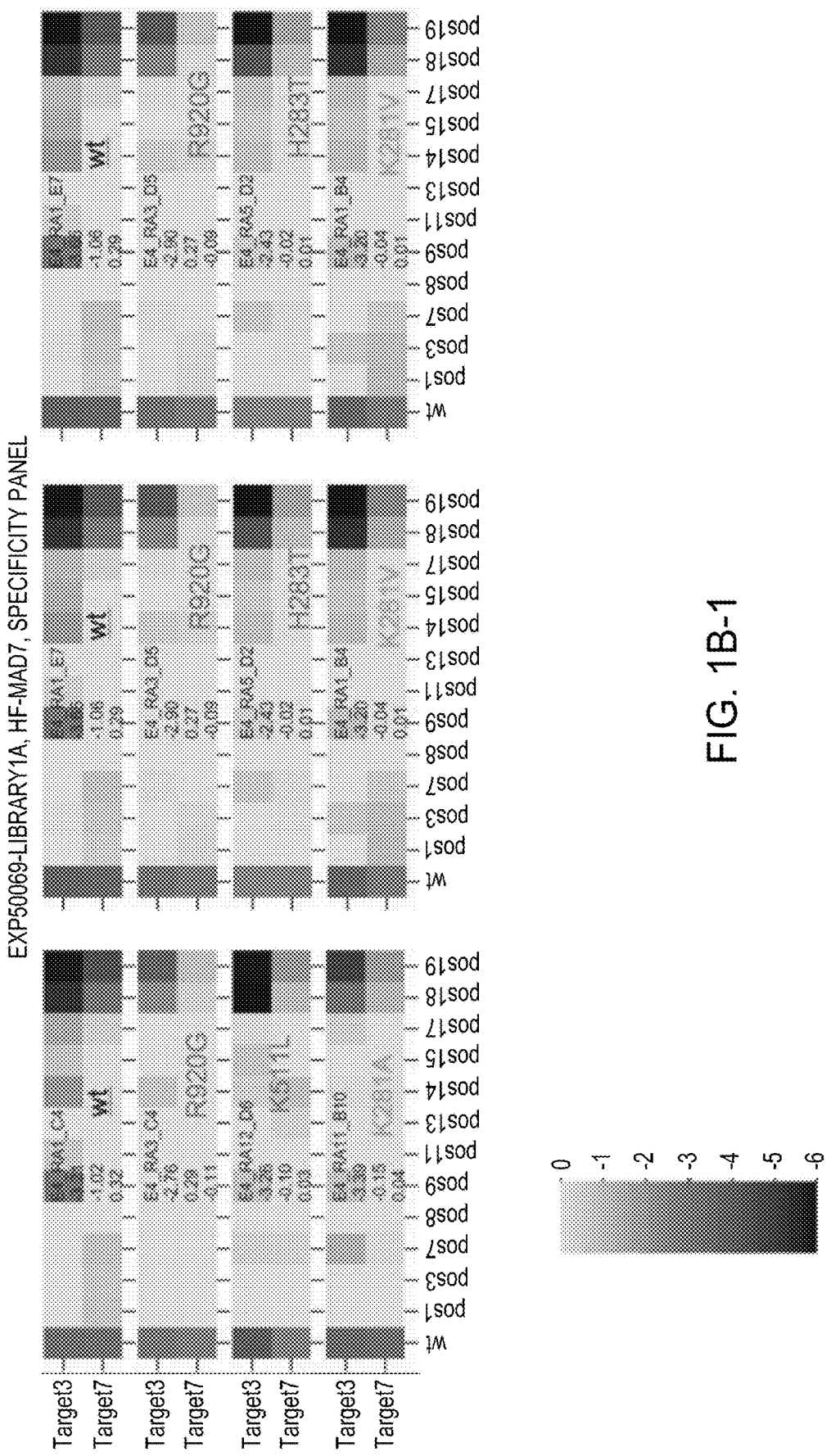
FIG. 1B is a heatmap for certain of the MAD70-series nucleases with varied fidelity as compared with the MAD7 (SEQ ID No.1).
Figures 1, 1B, 2:
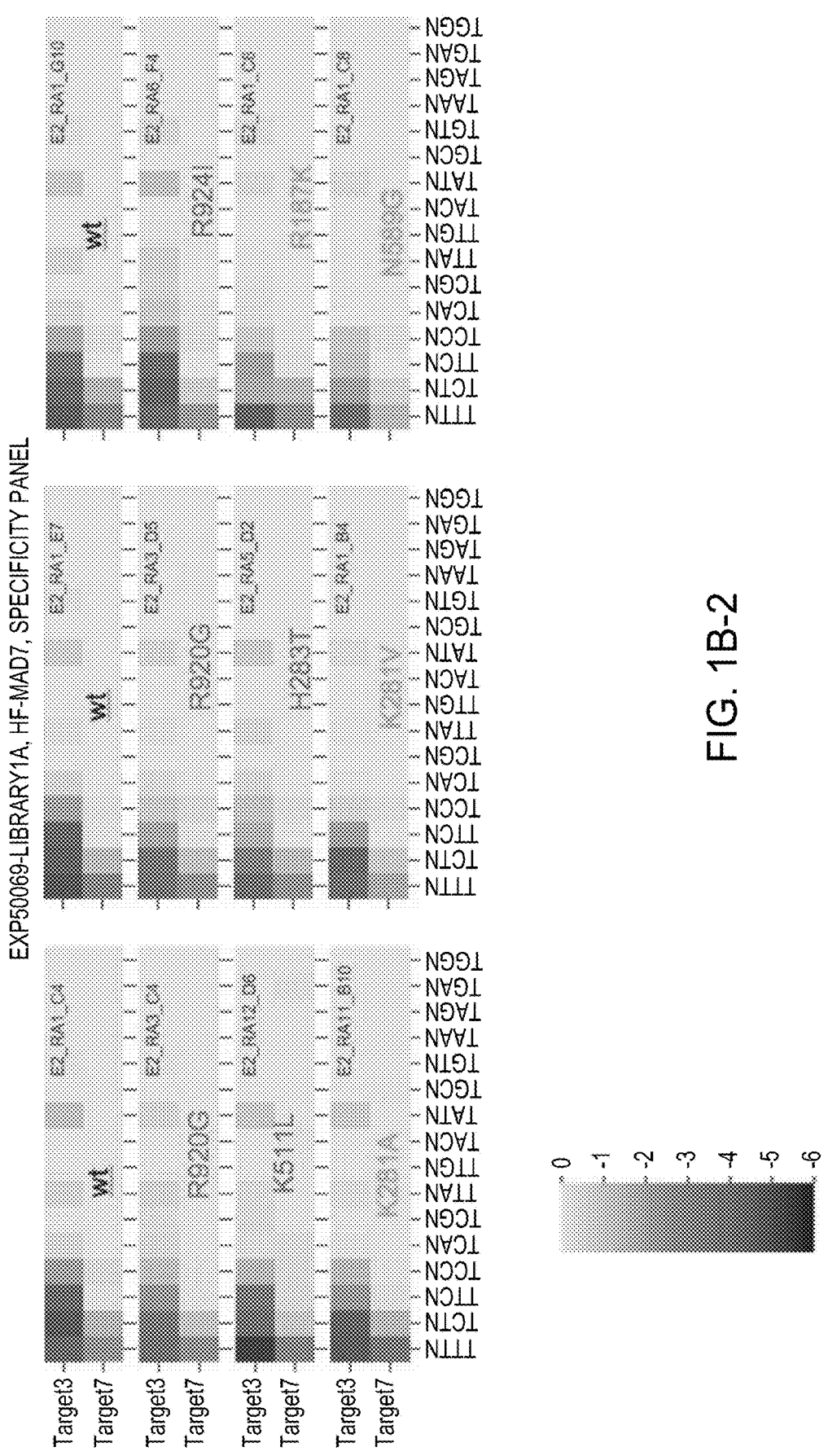

FIG. 1B is the heatmap for the MAD70-series variant nucleases with varied fidelity as compared with wild-type MAD7 (SEQ ID No. 1). The bottom figure shows the PAM depletion panel for the same enzyme from the above figure. R187K and N589G showed better pos9 specificity but note from the bottom figure these MAD70-series nucleases showed reduced activity across all PAMs. As can be seen many of these mutations eliminate activity of the enzyme for targets that contain programmed 2 bp mismatches at the +9, +14, +15, and +17 positions relative to the PAM sequence indicating an improved targeting fidelity.

Figure 2A:
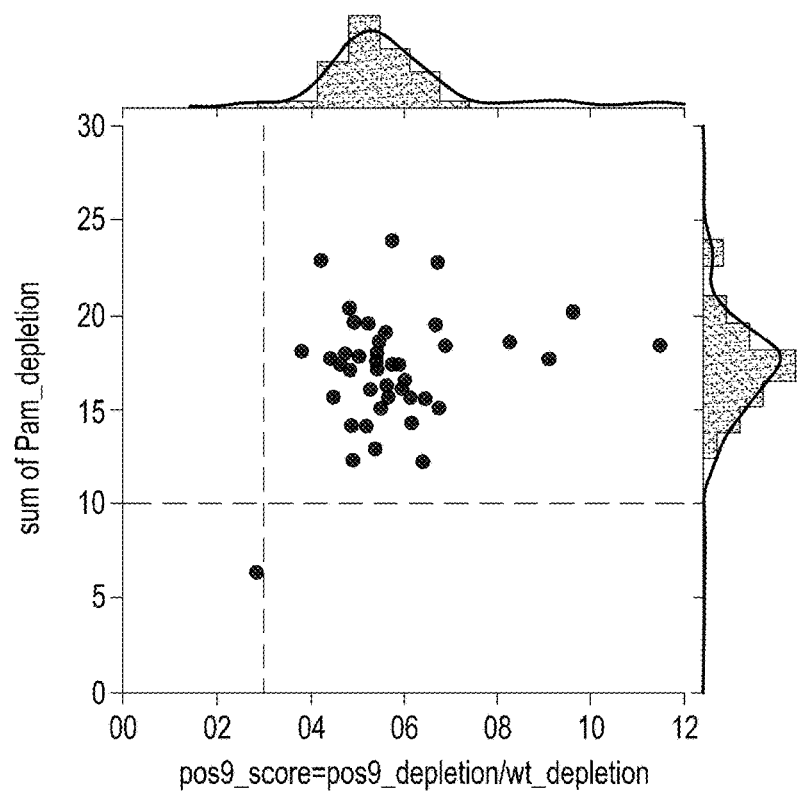
FIGS. 2A and 2B show the results of 108 engineered MAD70-series nucleases selected from screening 1104 single amino acid variants.

FIG. 2A is a PAM depletion vs specificity plot of the native MAD7 sequence (SEQ ID No. 1) sampled across multiple plates in a HT-screen. The PAM specificity is represented as the sum of the depletion scores observed for all PAMs tested ($D_{PAM}$) as calculated by Eqn 1:

$$PAM_{score} = \Sigma D_{PAM} \qquad \text{eqn.1:}$$

Figure 2B:
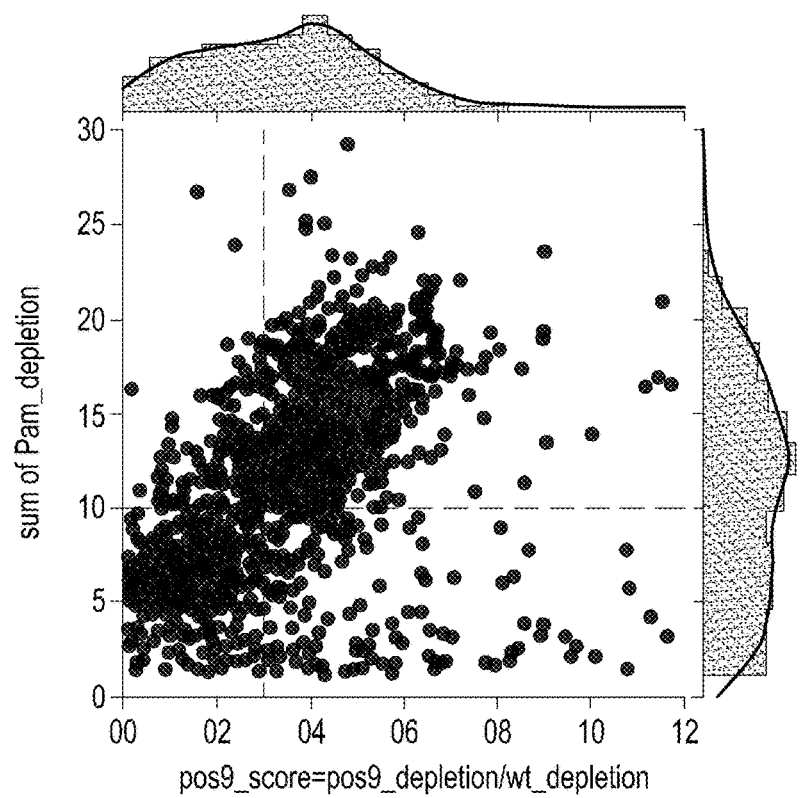

The relative nuclease specificity is calculated as the pos9_score as shown in eqn 2.

$$pos9_{score} = \frac{D_9}{D_{wt}} \qquad \text{eqn. 2}$$

Where $D_9$ is the sum of the depletion scores for DNA target sequences containing a 2 bp mismatch at the PAM +9 position and $D_{wt}$ is the sum of the depletion scores for DNA targets with perfect complementarity to the gRNAs used in this assay. This scoring methodology was chosen empirically based on the sensitivity of the targeting specificity to mutations in this register of the RNA-DNA interaction. Each point corresponds to an independent measurement from control digestion experiments run with the MAD7 nuclease (SEQ ID NO. 1). FIG. 2B is the plot for the screened 1108 single amino acid variants tested. Points in the lower two quadrants represent loss of function mutations which occurred in 433/1020 (43%) of the screened space. Data points in the upper left portion of the graph (>10 sum of Pam_depletion, <0.3 pos_9_depletion/wt_depletion) represent variants that with high activity as judged by their summed PAM activity score and high altered RNA-guided enzyme fidelity relative to the wild-type MAD7 enzyme sequence (FIG. 2A).

Example 8: Combinatorial Mutation Library Construction, Screening and Data Analysis Based on the results observed in Example 7, an additional mutant library was designed and screened for changes in PAM preference. The library was composed of mutations at both positions K535 and K594 (the residues are in relation to the MAD7 amino acid sequence in SEQ ID No. 1) substituting the original codon with NNK (IUPAC code for DNA: N=A, T, G, C; K=G, T) randomized codons. The library was constructed using a Q5 Site Directed Mutagenesis Kit (NEB) using manufacturers protocols with mutagenic forward 5'-TTCTNNKAACGCTATCATACTGATGC (SEQ ID No. 25) and reverse 5'TACTCMNNGGACTTT-GACCAACCGTC (SEQ ID No. 26) primers. The PCR reaction mix was transformed into 5-alpha chemically competent cells (NEB) and plated on LB agar plates with 100 µg/mL of carbenicillin. Colonies were picked and inoculated into 1 mL of LB medium (100 µg/mL of carbenicillin) in 96-well culture blocks and grown overnight in a shaking incubator at 37° C. Sample processing and screening was performed as described in examples 3, 4, 5 and 6.

Figure 5:
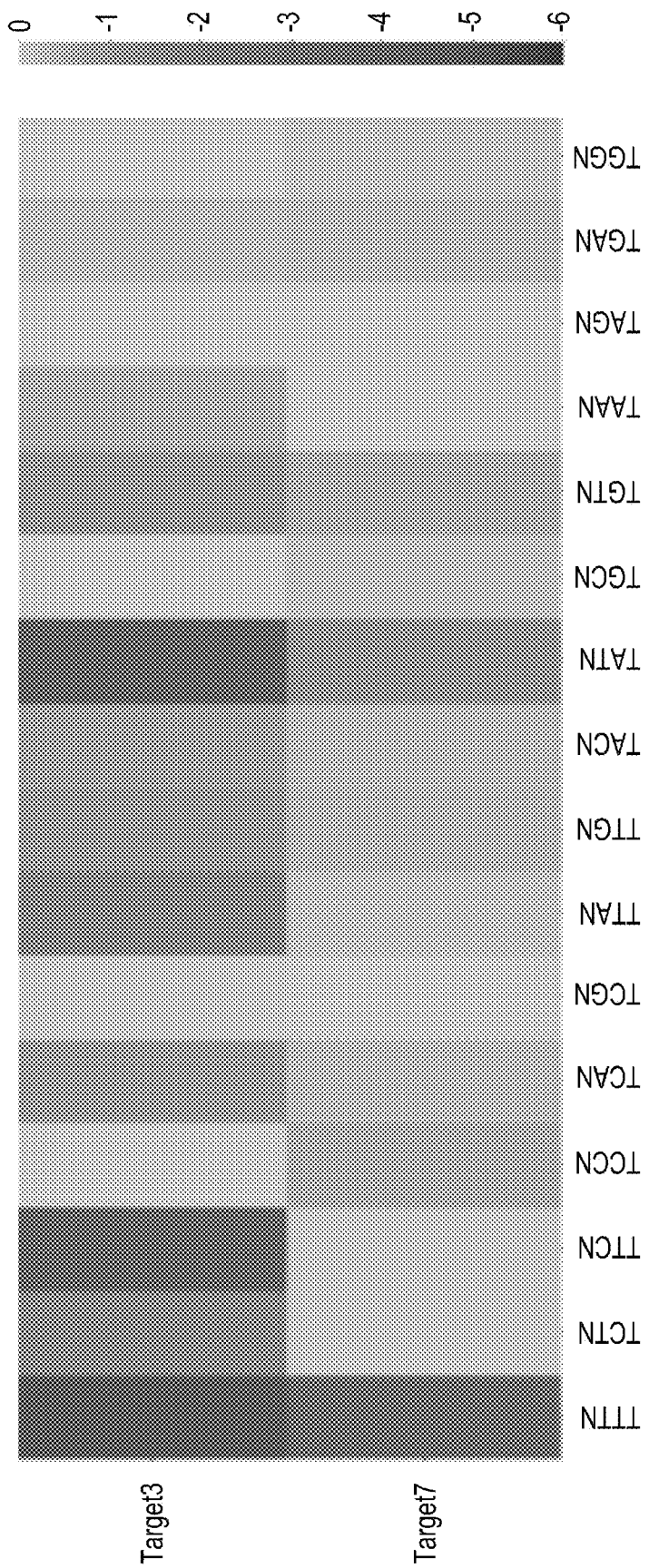
FIG. 5 is a heatmap for PAM preferences for MAD70-series variants from a combinatorial library screen.

FIG. 5 is a heatmap for a MAD70-series nuclease with novel PAM recognition sites identified from this library screening (SEQ ID No. 67). This mutant contains the combination of mutations K535R and N539S (SEQ ID No. 67) and results in more robust activity on PAMs with an A nucleotide at the second position of the NNNN PAM space, in particular TAAN, compared to the K535R mutation alone.

Example 9: Revised Target Library

A revised PAM panel library was designed by adding NNNN randomized sequences as the 5'-end PAM for each target, in order to evaluate activity on all 256 PAM sequences in the NNNN PAM space. Oligo pools were ordered from Twist Bioscience (Carlsbad, Calif.) using the following designs: Target3: 5'-CCAGTCAGTAATGT-TACTGG (SEQ ID No. 27), and Target7: 5'-AGCAGGA-CACTCCTGCCCCA (SEQ ID No. 28). The target library was cloned into a pUC19 backbone and prepared using the Midi-plus™ plasmid preparation kit (Qiagen). The target library pool was prepared at 10 ng/µL final concentration.

TABLE 7

Revised Library

| Target Library | PAM 5' | 3' UMI | Number of PAMs for analysis | Variant/Design |
|---|---|---|---|---|
| PAM panel (2 targets) | NNNN | none | 256 | 1 |

Example 10: Mutagenic Library Construction, Screening and Data Analysis Using K535R/N539S Backbone In order to further alter the PAM preference, a library of single amino acid mutations was generated using the K535R/N539S mutant (SEQ ID No. 67) described in Example 8. Mutation sets were generated based on residue proximity to putative key regions of where the nuclease is predicted to interact with the PAM site, target, or gRNA, as well as targeting charged amino acids. The following amino acid residues were targeted for mutation (the residues are in relation to the MAD7 amino acid sequence in SEQ ID No. 1): 529, 530, 531, 532, 534, 536, 537, 538, 540, 541, 582, 583, 584, 585, 586, 587, 588, 589, 590, 591, 592, 593, 594, 595, 599, 601, 650, 739, 740, 741, 742, 743. At each position, the original codon was substituted with NNK (IUPAC code for DNA: N=A, T, G, C; K=G, T) randomized codons. This library was screened for altered PAM preference as described in examples 3, 4, 5 and 6, using the target oligonucleotide library described in Example 9.

Figure 6A:
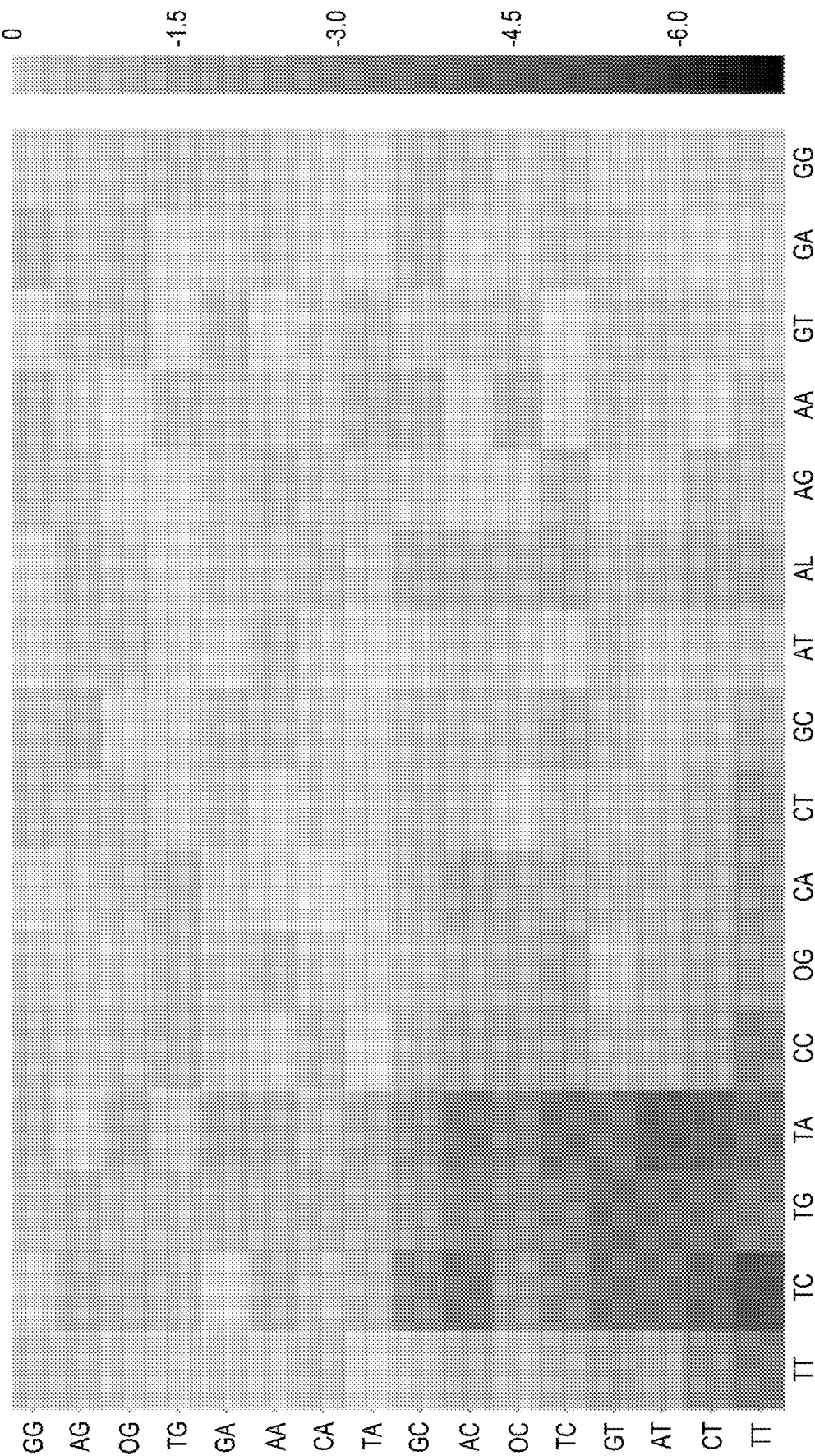
FIG. 6A is a complete NNNN PAM preference for wild-type MAD 7 (SEQ ID No. 1).
Figure 6B:
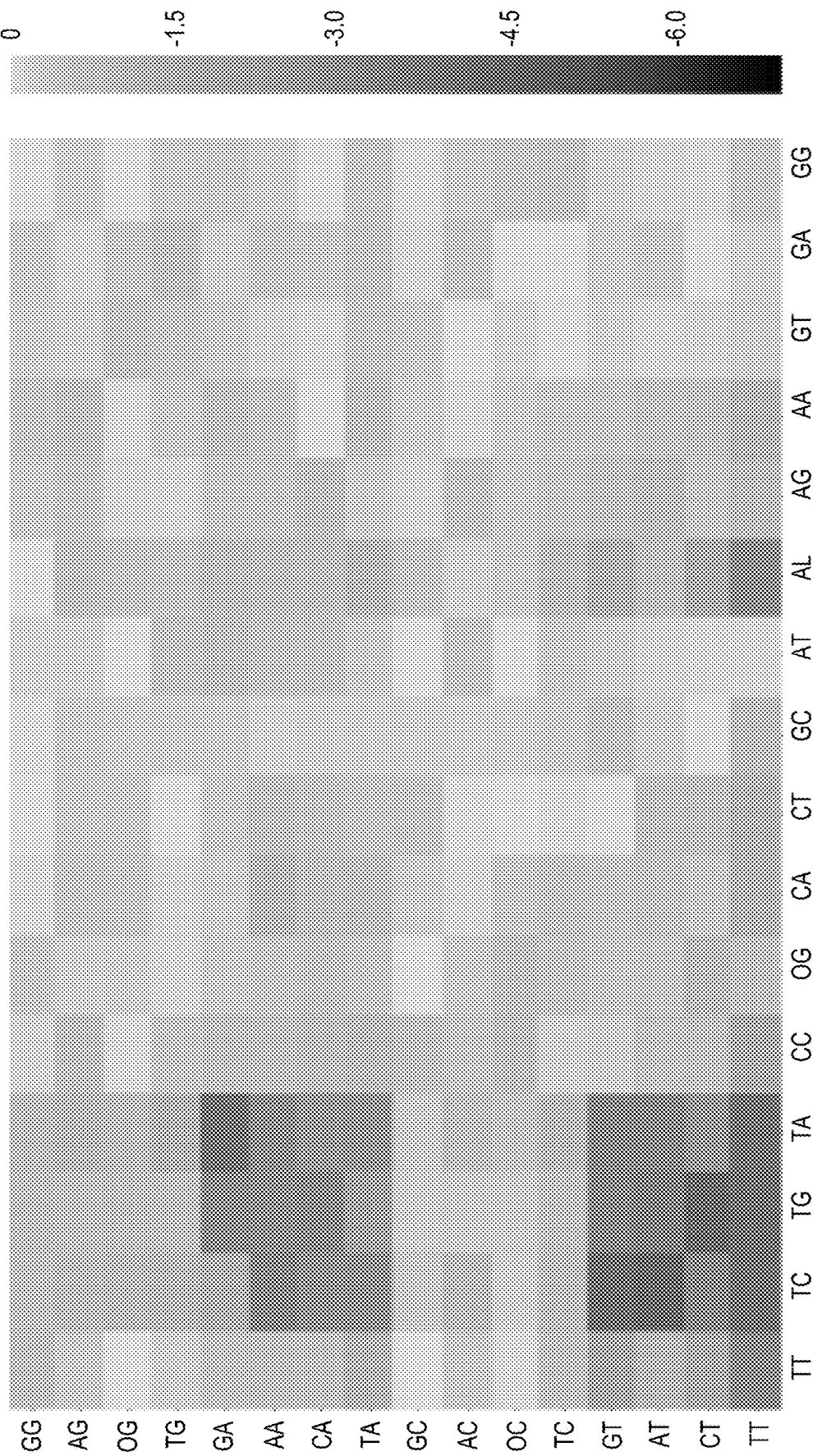
FIG. 6B is a complete NNNN PAM preference for the K535R/N539S mutant (SEQ ID No. 67).
Figure 6C:
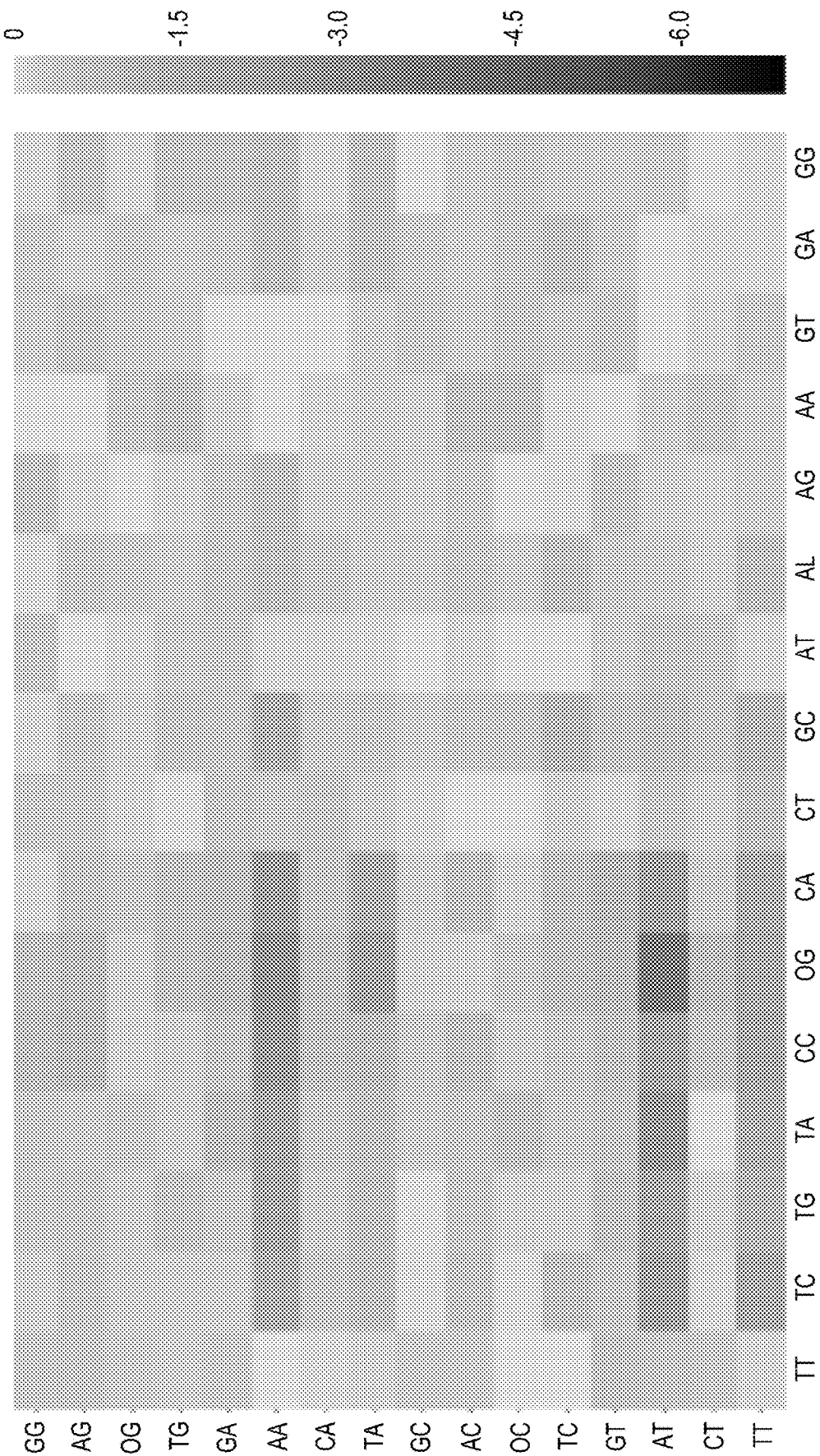
FIG. 6C is a complete NNNN PAM preference for the K535R/N539S/K594L/E730Q mutant (SEQ ID No. 68).

FIG. 6 represents activity heatmaps for wild-type MAD7 (SEQ ID No. 1) (FIG. 6A), the K535R/N539S mutant (SEQ ID No. 67) (FIG. 6B) used as the parent for this library, along with an additional MAD70-series nuclease with novel PAM recognition sites identified from this library (SEQ ID No. 68) (FIG. 6C). Data analysis was performed as described in Example 7, with heatmaps now representing activity on all 64 combinations of nucleotides in the NNNN PAM space. The new MAD70-eries nuclease mutant (SEQ ID No. 68) contains the combination of mutations K535R/N539S/K594L/E730Q in relation to the wild-type MAD7 amino acid sequence in SEQ ID No. 1. It has novel activity on PAMs with a C nucleotide at the third position of the NNNN PAM space.

Example 11: Activity of MAD70-series PAM mutants in *Escherichia coli* cells

In order to confirm activity of the MAD70-series mutants for genome editing systems in cells, activity was confirmed using a phenotypic editing assay in *E. coli*. MAD70-series mutants were cloned into a EE0026 vector backbone. MAD70-series variants were amplified using reverse (5' GATGATTTCTCTAGAGGTACTTAGAGATAGCGCTT-ATTCTGGATAAAGTC) (SEQ ID No. 29) and forward (5' CGATTCCGGAAAGGAGATATCTCATGAACAACG-GCACAAATAATTTTCAG AA) (SEQ ID No. 30) primers and cloned into the linearized EE0026 Engine vector using the NEBuilder HF DNA assembly kit.

Editing cassettes were designed to introduce stop codons to disrupt the synthesis of full-length LacZ in *E. coli* as a result of editing. Each cassette was composed of a 20 base pair spacer to precisely target a region of lacZ gene in the *E. coli* genome adjacent to the indicated PAM sequence in the genome, and a 200 bp repair template for homologous recombination. DNA sequences and corresponding PAM targets for each cassette are provided in Table 8. Each cassette is cloned into the common cassette vector backbone p346BB (SEQ ID No. 87) using the NEBuilder HF DNA assembly kit. *E. coli* K-12 str MG1655 grown to mid-log phase in LB was made electrocompetent by washing three times with ice cold 10% glycerol. Engine vectors were transformed by electroporation, recovered in SOC for 1 hr at 30° C., then grown overnight on LB agar with Chloramphenicol (25 ug/mL) medium at 30° C. Overnight grown cells with MAD70-series variant engine vectors were grown to mid log phase in LB Chloramphenicol (25 ug/mL) and made competent with LB broth containing 10% (wt/vol) polyethylene glycol, 5% (vol/vol) dimethyl sulfoxide, and 50 mM Mg2+ at pH 6.5.

TABLE 8

Sequences of Editing cassettes and corresponding PAM targets

| Cassette name | Insert sequence | Target gene | PAM | SEQ ID No. |
|---|---|---|---|---|
| lacZ_127_TTTC_stop | GTGTGTGATACGAAACGAAGCATTGGAGGCATTG GAATTTCTACTCTTGTAGATACCCTGCCATAAAGA AACTGTCCATGTTGCCACTCGCTTTAATGATGATT TCAGCCGCGCTGTACTGGAGGCTGAAGTTCAGAT GTGCGGCGAGTTGCGTGACTACCTACGGGTAACA TAATGATTATGGTAATGAGAGACCCAGGTCGCCA GCGGCACCGCGCCTTTCGGCGGTGAAATTATCGA TGAGCGTGGTGGTTATGCCGATCGCGTCACACTA ATCCCAGAAAAGACCCGTCCG | lacZ | TTTC | 31 |
| lacZ_245_TTTC_stop | GTGTGTGATACGAAACGAAGCATTGGAGGCATTG GAATTTCTACTCTTGTAGATCATGTTGCCACTCGC TTTAATCACCCTGCCATAAAGAAACTGTTACCCGT AGGTAGTCACGCAACTCGCCGCACATCTGAACTT CAGCCTCCAGTACAGCGCGGCTGAAATCATCATTT CATTAAGTGGCTCATTAGAGATAGCTGATTTGTGT AGTCGGTTTATGCAGCAACGAGACGTCACGGAAA ATGCCGCTCATCCGCCACATATCCTGATCTTCATC CCAGAAAAGACCCGTCCG | lacZ | TTTC | 32 |
| lacZ_256_TTTG_stop | GTGTGTGATACGAAACGAAGCATTGGAGGCATTG GAATTTCTACTCTTGTAGATTGTAGTCGGTTTATG CAGCAACCGCCTCGCGGTGATGGTGCTGCGCTGG AGTGACGGCAGTTATCTGGAAGATCAGGATATGT GGCGGATGAGCGGCATTTTCCGTGACGTCTCGTTG TAATGAAAACCGTAATGACAGATTAGCGATTTCC ATGTTGCCACTCGCTTTAATGATGATTTCAGCCGC GCTGTACTGGAGGCTGAAGTTCAGATGTGCGGCA TCCCAGAAAAGACCCGTCCG | lacZ | TTTG | 33 |
| lacZ_419_TTTG_stop | GTGTGTGATACGAAACGAAGCATTGGAGGCATTG GAATTTCTACTCTTGTAGATCCGTCTGAATTTGAC CTGAGCTCATCCGCCACATATCCTGATCTTCCAGA TAACTGCCGTCACTCCAGCGCAGCACCATCACCG CGAGGCGGTTTTCTCCGGCGCGTAAAAATGCGCTT CATTAAAATTCTCATTACAGACCACTGTCCTGGCC GTAACCGACCCAGCGCCCGTTGCACCACAGATGA AACGCCGAGTTAACGCCATCAAAAATAATTCGAT CCCAGAAAAGACCCGTCCG | lacZ | TTTG | 34 |

TABLE 8-continued

Sequences of Editing cassettes and corresponding PAM targets

| Cassette name | Insert sequence | Target gene | PAM | SEQ ID No. |
|---|---|---|---|---|
| lacZ_314_TATG_stop | GTGTGTGATACGAAACGAAGCATTGGAGGCATTGGAATTTCTACTCTTGTAGATTGGCGGATGAGCGGCATTTTTCCAGTACAGCGCGGCTGAAATCATCATTAAAGCGAGTGGCAACATGGAAATCGCTGATTTGTGTAGTCGGTTTATGCAGCAACGAGACGTCACGGAATCATTAGCTCATTCATTACACATTCTGATCTTCCAGATAACTGCCGTCACTCCAGCGCAGCACCATCACCGCGAGGCGGTTTTCTCCGGCGCGTAAAAATGCATCCCAGAAAAGACCCGTCCG | lacZ | TATG | 35 |
| lacZ_920_TATG_stop | GTGTGTGATACGAAACGAAGCATTGGAGGCATTGGAATTTCTACTCTTGTAGATACCATGATTACGGATTCACTCTATTACGCCAGCTGGCGAAAGGGGGATGTGCTGCAAGGCGATTAAGTTGGGTAACGCCAGGGTTTTCCCAGTCACGACGTTGTAAAACGACGGCCAGTCATTACGTAATTCATTACACTCATGTTTCCTGTGTGAAATTGTTATCCGCTCACAATTCCACACAACATACGAGCCGGAAGCATAAAGTGTAAAGCCTGGGATCCCAGAAAAGACCCGTCCG | lacZ | TATG | 36 |
| lacZ_1712_AACG_stop | GTGTGTGATACGAAACGAAGCATTGGAGGCATTGGAATTTCTACTCTTGTAGATCCATCAAAAATAATTCGCGTATTACGGTCAATCCGCCGTTTGTTCCCACGGAGAATCCGACGGGTTGTTACTCGCTCACATTTAATGTTGATGAAAGCTGGCTACAGGAAGGCCAGACGTAATGAATTTTTTAATGAGTCAATTCGGCGTTTCATCTGTGGTGCAACGGGCGCTGGGTCGGTTACGGCCAGGACAGTCGTTTGCCGTCTGAATTTGACCTATCCCAGAAAAGACCCGTCCG | lacZ | AACG | 37 |
| lacZ_466_AACG_stop | GTGTGTGATACGAAACGAAGCATTGGAGGCATTGGAATTTCTACTCTTGTAGATGGGATACTGACGAAACGCCTAATGGCTTTCGCTACCTGGAGAGACGCGCCCGCTGATCCTTTGCGAATACGCCCACGCGATGGGTAACAGTCTTGGCGGTTTCGCTAAATACTGGCAGTAATGACGTCAGTAATGACGACTTCAGGGCGGCTTCGTCTGGGACTGGGTGGATCAGTCGCTGATTAAATATGATGAAAACGGCAACCCGTGGTCGGCTTACATCCCAGAAAAGACCCGTCCG | lacZ | AACG | 38 |

Figure 7:
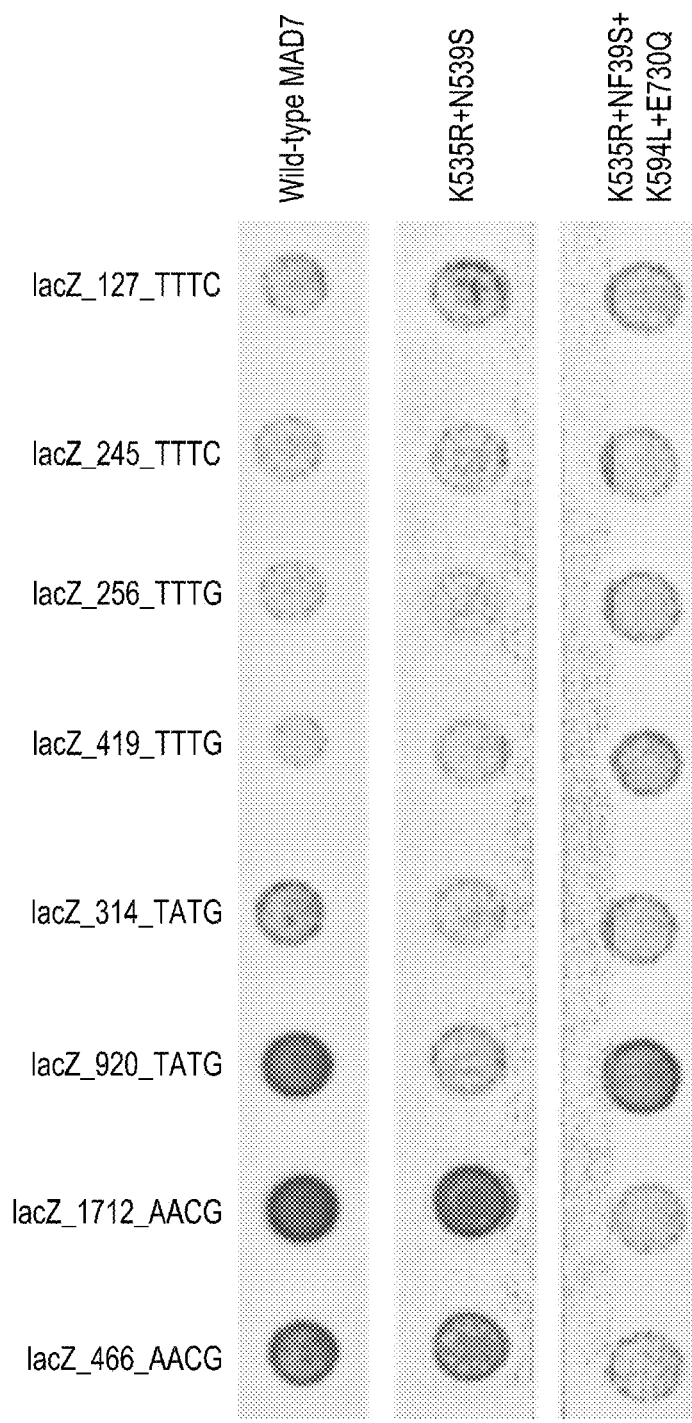
FIG. 7 shows colonies containing editing cassettes and wild-type MAD7, MAD70-series variants K535R/N539S (SEQ ID No. 67) and K535R/N539S/K594L/E730Q (SEQ ID No. 68) mutants in relation to the wild-type MAD7 amino acid sequence.

10 ng of editing cassette plasmid was added to 20 uL of chemically competent E. coli strain with an engine vector on ice. After 30 min, 250 uL of SOC was added and the cultures were incubated in a shaking incubator for 1 hr at 30° C. 30 uL of the resulting cultures were inoculated to 350 uL of LB Carbenicillin (100 ug/mL)/Chloramphenicol (25 ug/mL) and grown overnight in a shaking incubator at 30° C. 4 uL of the overnight cultures were inoculated to fresh 320 uL LB/Carbenicillin (100 ug/mL)/Chloramphenicol (25 ug/mL)/Arabinose (1% w/v) medium and incubated for 3 hrs in a shaking incubator at 30° C. Cultures were moved to a 42° C. shaking incubator to induce the production of RNP complex. After 5 hrs of induction at 42° C., cultures were moved back to the 30° C. shaking incubator and grown overnight. Overnight grown edited strains were spotted on a MacConkey Agar Plates (Teknova) and grown overnight at 37° C. without any antibiotics. Cultures with native LacZ can ferment the lactose in the medium, produces acid that lowers the pH that makes the red color in the colony. Cultures with edited disrupted LacZ can't ferment the lactose and the colonies grow colorless. A summary of editing phenotypes observed for MAD70-series PAM mutants is shown in FIG. 7. Darker spots indicate intact lacZ and lighter spots are cells with lacZ that are edited and thus are non-functional, indicating gene editing activity on the PAMs listed at top.

Figure 8:
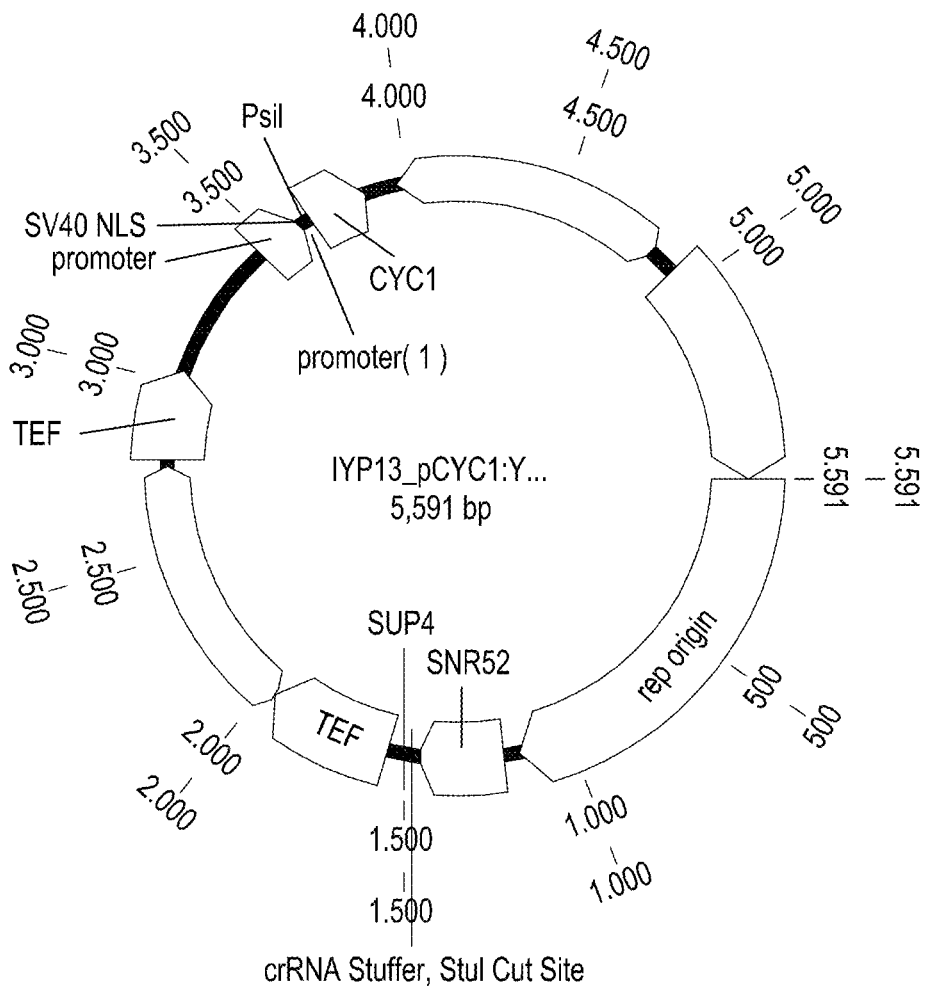
FIG. 8 is a map of the plasmid used for the screening of nuclease proteins for genome editing activity in *S. cerevisiae*.
Figure 9:
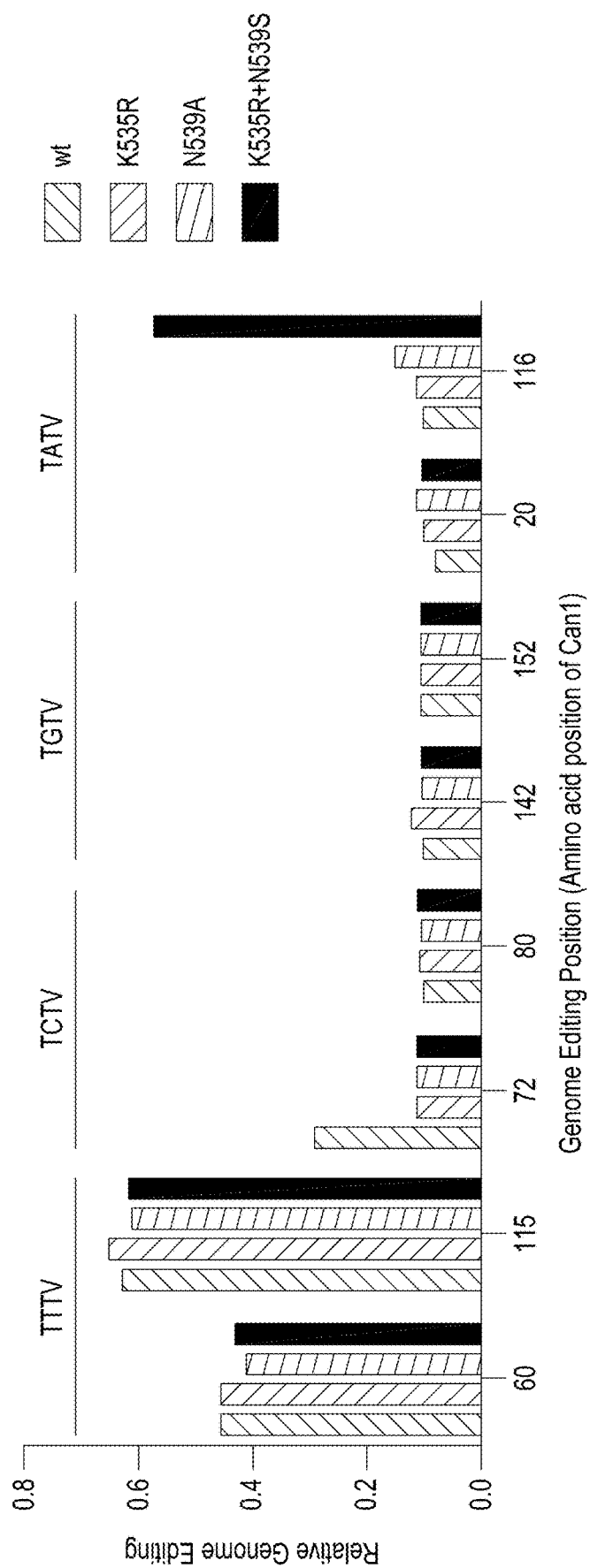
FIG. 9 shows the relative rates of genome editing at different positions of the Can1 protein locus with the indicated PAM by wild-type MAD7, and the K535R (SEQ ID No. 13), N539A and K535R/N539S (SEQ ID No. 67) MAD70-series mutants.

Example 12: Phenotypic Assay to Measure Genome Editing for MAD7-Derived Mutants in Saccharomyces cerevisiae Cells To assess the genome editing activity of RNA-guided nucleases in S. cerevisiae, a two micron plasmid was constructed for the sequential introduction of DNA containing an editing cassette with SNR52 promoter-driven crRNA and a CYC1 promoter-driven nuclease protein (see FIG. 8). The editing cassette comprises the crRNA to guide the nuclease to cut at a specific DNA sequence, a short linker, and a repair template containing the mutation of interest flanked by regions of homology to the genome. The screening plasmid (FIG. 8) was linearized by the StuI restriction endonuclease, and the editing cassette was introduced downstream of the SNR52p promoter by isothermal assembly. The editing cassettes inserted into the StuI-linearized plasmid for the introduction of a premature stop codon into the can1 gene, organized by the PAM of the corresponding spacer, are shown in Table 9. The nuclease proteins were amplified by polymerase chain reaction with oligonucleotide primers to introduce an SV40 nuclear localization sequence at the N-terminus consisting of the DNA sequence "ATGGCAC-CCAAGAAGAAGAGGAAGGTGTTA" (SEQ ID No. 39) corresponding to a protein sequence of "MAPKKKRKVL (SEQ ID No. 40)." The resulting amplified DNA fragment (400 ng, purified) was then co-transformed along with a PsiI-linearized screening plasmid (250 ng) that already contained an editing cassette to assemble the complete editing plasmid by in vivo gap repair. Cells containing a repaired plasmid were selected for in yeast peptone-dextrose (YPD) containing 200 mg/L Geneticin for 3 days at 30 degrees C. in a humidified shaking incubator. The resulting saturated culture was diluted 1:80 into synthetic complete yeast media lacking arginine and containing 50 mg/L of canavanine and grown overnight at 30 degrees C. in a humidified shaking incubator. Because knockout of the Can1 protein allows yeast to grow in the presence of the otherwise toxic analog canavanine, the relative OD600 of the overnight cultures is proportional to the rate of genome mutation induced by the transformed nuclease protein. The MAD70-series variants described in Examples 7 and 8 with altered PAM preference were evaluated in the assay system using the editing cassettes shown in Table 9, targeting various PAMs. The results of this analysis are shown in FIG. 9, where the mutant containing mutations K535R, K539S in reference to the wild-type MAD7 sequence shows substantially higher editing activity on TATV PAMs.

TABLE 9

Editing cassettes targeting yeast can1 gene to introduce loss of function mutations

| Cassette name | PAM | Editing Cassette Sequence | SEQ ID No. |
|---|---|---|---|
| Can1_S30stop | TTTA | GGCCCCAAATTCTAATTTCTACTGTTGTAGATAC GACGTTGAAGCTTCACAATTTTTACGCCGACAT AGAGGAGAAGCATATGTACAATGAGCCGGTCAC AACCCTCGAGACACGACGTTGAAGCTTAACAAA CACACCACAGACGTGGGTCAATACCATTGAAAG ATGAGAAAAGTAACAATATACGCGCTCCTGCCC | 41 |
| Can1_K42stop | TTTA | GGCCCCAAATTCTAATTTCTACTGTTGTAGATCT TTTCTCATCTTTCAATGGTTTTTGTATCCTCGCCA TTTACTCTCGTCGGGAAAGAGCGCAATGGATAC AATTCCCCACTTTTCTCATCTTACAATGGTATTG ACCCACGTCTGTGGTGTGTTTGTGAAGCTTCAAC GTCGTCAATATACGCGCTCCTGCCC | 42 |
| Can1_N60stop | TTTC | GGCCCCAAATTCTAATTTCTACTGTTGTAGATCC GACGAGAGTAAATGGCGATTTTTTCAATACCAT TGAAAGATGAGAAAAGTAAAGAATTGTATCCAT TGCGCTCGTTCCCGACGAGAGTATAAGGCGAGG ATACGTTCTCTATGGAGGATGGCATAGGTGATG AAGATGAAGGAGAAGCAATATACGCGCTCCTGC CC | 43 |
| Can1_T115stop | TTTA | GGCCCCAAATTCTAATTTCTACTGTTGTAGATTC CACACCTCTGACCAACGCTTTTTATTGGTATGAT TGCCCTTGGTGGTACTATTGGTACAGGTCTTTTC ATTGGATTATCCACACCTCTGTAAAACGCCGGC CCAGTGGGCGCTCTTATATCATATTTATTTATGG GTTCTTTGGCATCAATATACGCGCTCCTGCCC | 44 |
| Can1_Q158stop | TTTC | GGCCCCAAATTCTAATTTCTACTGTTGTAGATAC AGTTTTCTCACAAAGATTTTTTTCTGTCACGCA GTCCTTGGGTGAAATGGCTACATTCATCCCTGTT ACATCCTCGTTCACAGTTTTCTCATAAAGATTCC TTTCTCCAGCATTTGGTGCGGCCAATGGTTACAT GTATTGGTTTTCAATATACGCGCTCCTGCCC | 45 |
| Can1_I214stop | TTTG | GGCCCCAAATTCTAATTTCTACTGTTGTAGATGG TAATTATCACAATAATGATTTTTCATTCAATTTT GGACGTACAAAGTTCCACTGGCGGCATGGATTA GTATTTGGAAGGTAATTATCACATAAATGAACT TGTTCCCTGTCAAATATTACGGTGAATTCGAGTT CTGGGTCGCCAATATACGCGCTCCTGCCC | 46 |
| Can1_G72stop | TCTA | GGCCCCAAATTCTAATTTCTACTGTTGTAGATTG GAGGATGGCATAGGTGATTTTTTAATTGTATCCA TTGCGCTCTTTCCCGACGAGAGTAAATGGCGAG GATACGTTCTCCATGGAGGATGGCATATAAGAT GAAGATGAAGGAGAAGTACAGAACGCTGAAGT GAAGAGAGAGCTTAACAATATACGCGCTCCTGC CC | 47 |
| Can1_Q80stop | TCTC | GGCCCCAAATTCTAATTTCTACTGTTGTAGATTT CACTTCAGCGTTCTGTACTTTTTCCAATAGTACC ACCAAGGGCAATCATACCAATATGTCTTTGCTT AAGCTCCCCCTTCACTTCAGCGTTTTATACTTCT CCTTCATCTTCATCACCTATGCCATCCTCCATAG AGAACGTATCAATATACGCGCTCCTGCCC | 48 |
| Can1_E142stop | TGTC | GGCCCCAAATTCTAATTTCTACTGTTGTAGATAC GCAGTCCTTGGGTGAAATTTTTTCCAGTGGGCGC TCTTATATCATATTTATTTATGGGTTCTTTGGCAT | 49 |

TABLE 9-continued

Editing cassettes targeting yeast can1 gene to introduce loss of function mutations

| Cassette name | PAM | Editing Cassette Sequence | SEQ ID No. |
|---|---|---|---|
| | | ATTCGGTCACGCAGTCCTTGGGTTAAATGGCTA CATTCATCCCTGTTACATCCTCTTTCACAGTTTTC TCACAAAGATCAATATACGCGCTCCTGCCC | |
| Can1_S152stop | TGTG | GGCCCCAAATTCTAATTTCTACTGTTGTAGATAG AAAACTGTGAAAGAGGATTTTTTAACCAATACA TGTAACCATTGGCCGCACCAAATGCTGGAGAAA GGAATCTCCCTGAGAAAACTGTGAATTAGGATG TAACAGGGATGAATGTAGCCATTTCACCCAAGG ACTGCGTGACAGCAATATACGCGCTCCTGCCC | 50 |
| Can1_V20stop | TATG | GGCCCCAAATTCTAATTTCTACTGTTGTAGATTA CAATGAGCCGGTCACAACTTTTTGGCATAGCAA TGACAAATTCAAAAGAAGACGCCGACATAGAG GAGAAGCACGGGTACAATGAGCCGTAAACAAC CCTCTTTCACGACGTTGAAGCTTCACAAACACA CCACAGACGTGGGTCAACAATATACGCGCTCCT GCCC | 51 |
| Can1_N116stop | TATC | GGCCCCAAATTCTAATTTCTACTGTTGTAGATCA CACCTCTGACCAACGCCGTTTTTGTATGATTGCC CTTGGTGGTACTATTGGTACAGGTCTTTTCATTG GTTTAAGTACACCTCTGACCTAAGCCGGCCCAG TGGGCGCTCTTATATCATATTTATTTATGGGTTC TTTGGCATATTCCAATATACGCGCTCCTGCCC | 52 |

Figure 10:
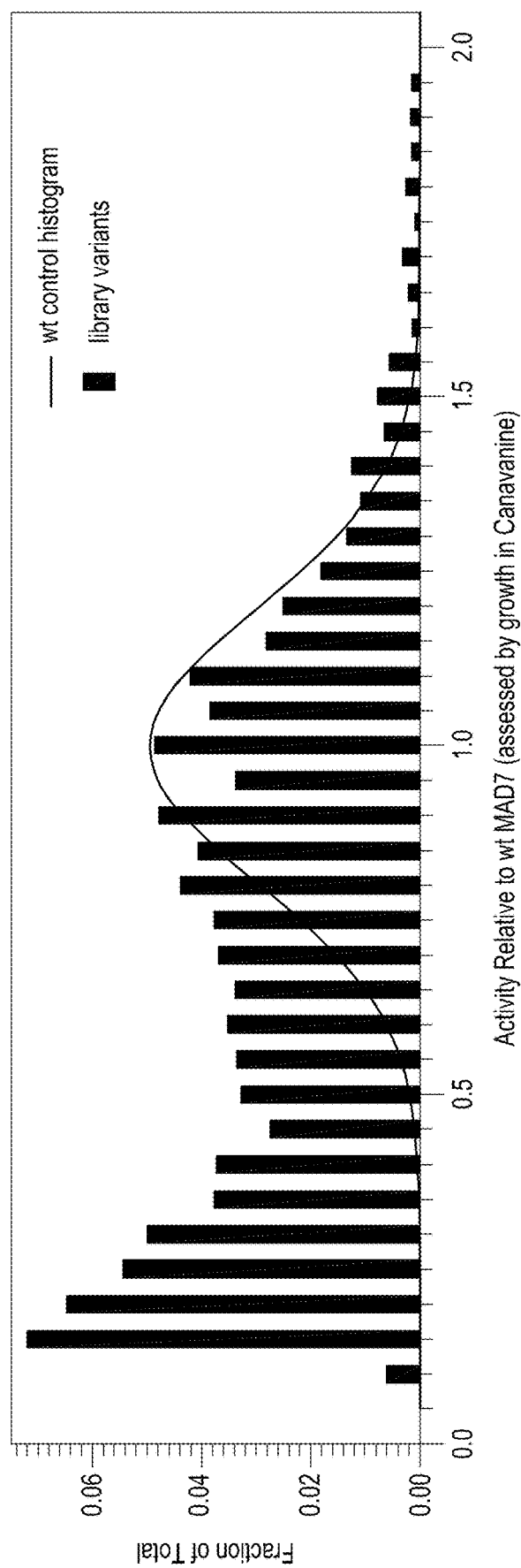
FIG. 10 shows the results of screening 2304 MAD70-series variants for genome editing activity in *S. cerevisiae*.
Figure 11:
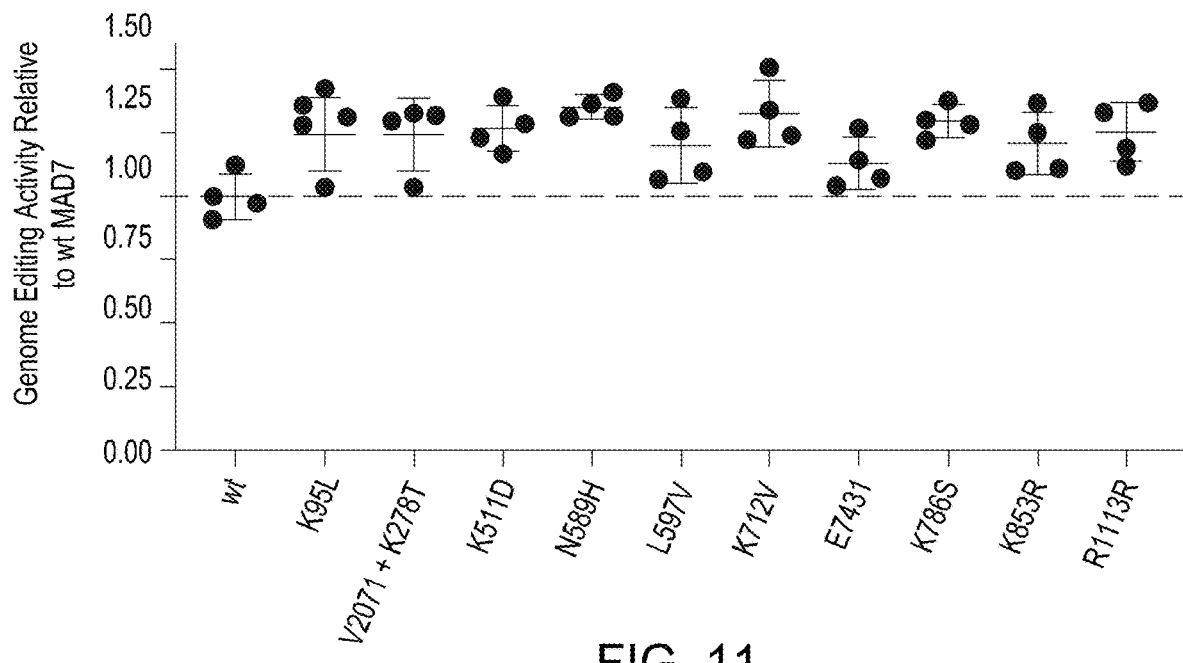
FIG. 11 shows quadruplicate re-testing of MAD70-series variants that demonstrated enhanced genome editing activity in *S. cerevisiae*.

Example 13: Testing of MAD7 Variant Proteins for Enhanced Genome Editing in S. cerevisiae To screen libraries of MAD7 enzyme variants with one or more mutations for increased genome editing activity in S. cerevisiae, six different editing cassettes (all targeting the TTTV PAM class) (first six entries in Table 9 (SEQ ID Nos. 41-46)) were inserted into the StuI-linearized two micron screening plasmid (again see FIG. 8) as described in Example 12. MAD7 protein variant coding sequences as described in Example 2 were amplified by polymerase chain reaction with oligonucleotide primers to introduce an SV40 nuclear localization sequence at the N-terminus consisting of the DNA sequence "ATGGCACCCAAGAAGAAGAG-GAAGGTGTTA" (SEQ ID No. 39) corresponding to a protein sequence of "MAPKKKRKVL (SEQ ID No. 40)." The resulting amplified DNA fragment (5 uL of crude PCR mixture) was then co-transformed along with a PsiI-linearized screening plasmid (150 ng total, a pool of all 6 editing cassettes) that already contains an editing cassette to assemble the complete editing plasmid by in vivo gap repair. Cells containing a repaired plasmid were selected for in yeast peptone-dextrose (YPD) containing 200 mg/L Geneticin for 3 days at 30° C. in a humidified shaking incubator. The resulting saturated culture was diluted into synthetic complete yeast media lacking arginine and containing 50 mg/L of canavanine and grown overnight at 30° C. in a humidified shaking incubator. Because knockout of the Can1 protein allows yeast to grow in the presence of the otherwise toxic analog canavanine, the relative OD600 of the overnight cultures is proportional to the rate of genome mutation induced by the transformed nuclease protein. The relative genome editing activity levels of each variant are plotted in FIG. 10. Rescreening of the variants in quadruplicate in the original assay confirmed the enhanced genome editing activity of several MAD70-series variants, as shown in FIG. 11. Sequences are provided in SEQ ID Nos. 69 (K95L), 70 (V201I/K278T), 71 (K511D), 72 (N589H), 73 (L597V), 74 (K712V), 75 (E743I), 76 (K786S), 77 (K853R), and 78 (R1113F).

Figure 12:
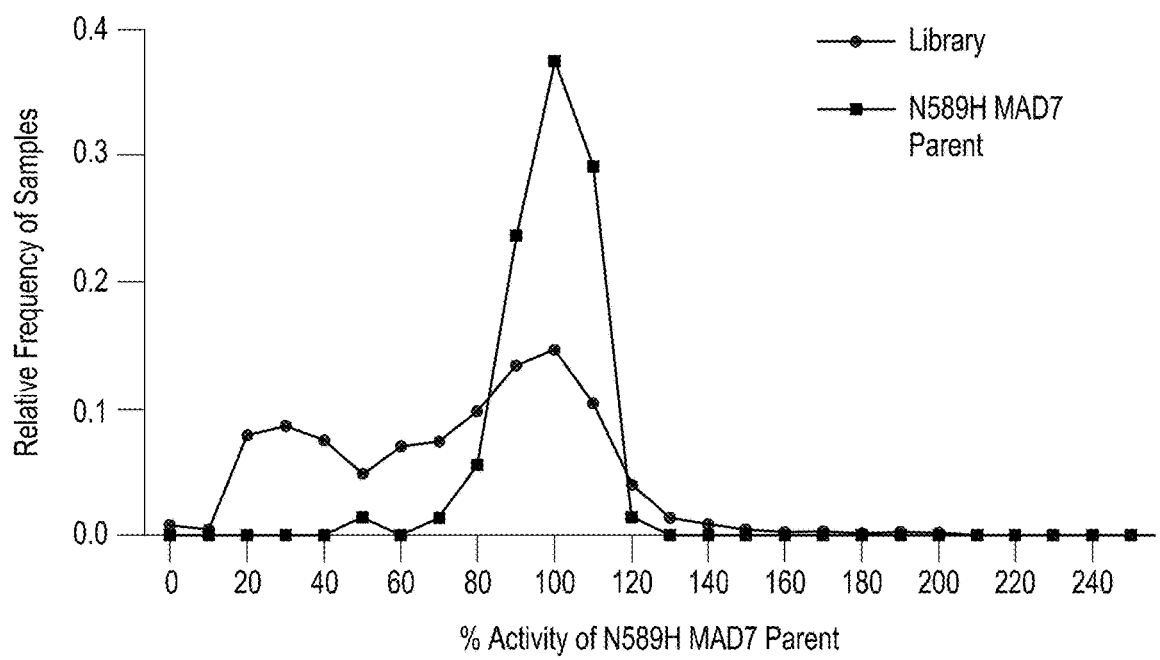
FIG. 12 shows the results of screening 2304 MAD70-series combinatorial protein variants for genome editing activity in *S. cerevisiae*.
Figure 13:
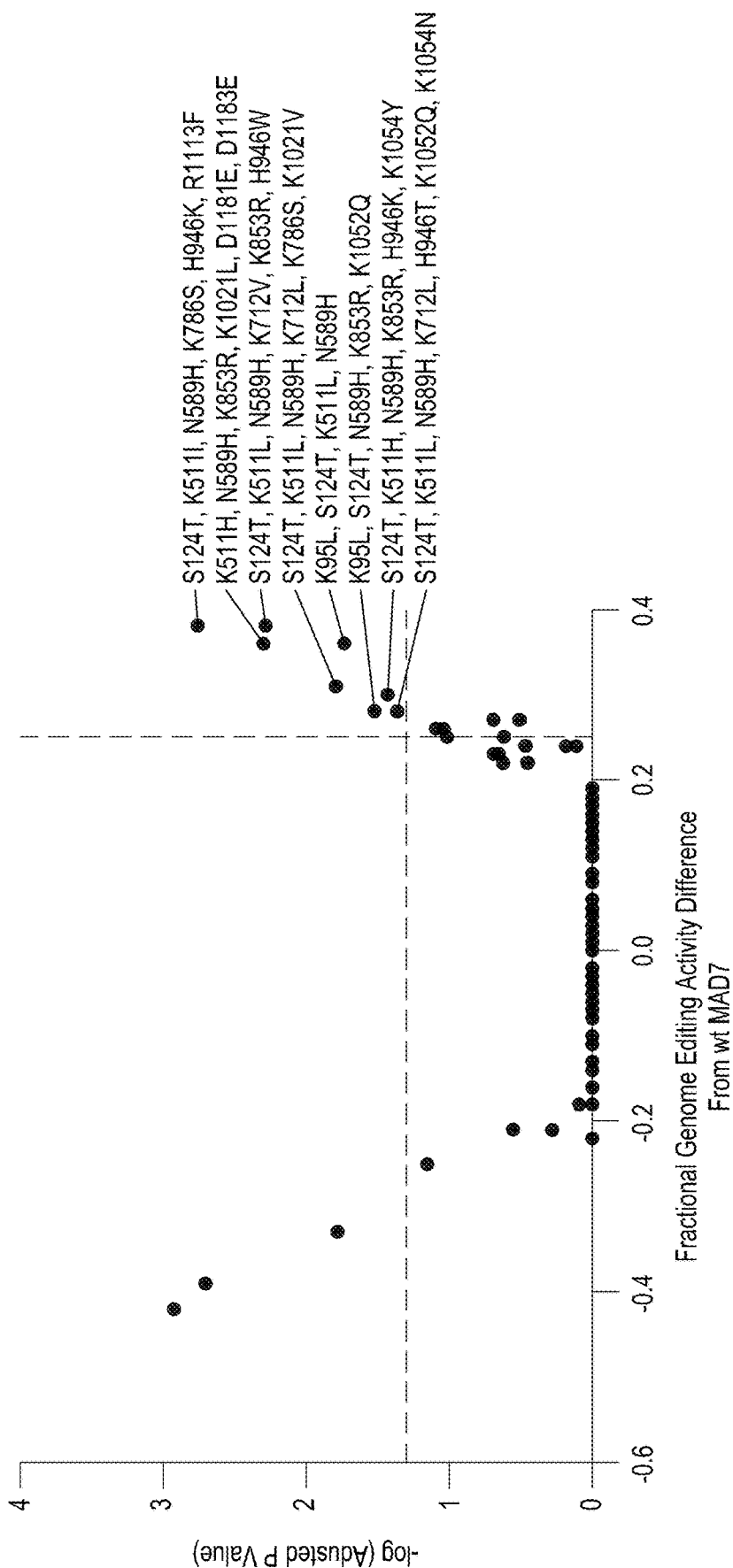
FIG. 13 shows the results of secondary screening of the MAD70-series combinatorial variant hits showing fractional difference in genome editing activity in *S. cerevisiae* and the multiple-comparison-adjusted P value for each variant as compared to the wild-type MAD 7 (SEQ ID No. 1) controls.

Example 14: Generation of Combinatorial MAD7 Variant Libraries and Screening for Enhanced Editing in S. cerevisiae Based on the identified single mutations that enhance the genome editing activity of MAD7 in S. cerevisiae, combinatorial libraries were prepared. The N589H MAD70-series variant sequence (SEQ ID No. 72) was used as a backbone and 4 to 5 additional mutations were introduced using oligonucleotide primers and the Quick-Change Lightning Multi-Site Mutagenesis kit (Agilent) according to manufacturer instructions. These variants were screened for genome editing activity in S. cerevisiae as described in Example 12 as depicted in FIG. 12. The variants that showed enhanced activity in the primary screen were rescreened in quadruplicate and the results of the secondary screening are depicted in FIG. 13. Sequences are provided in SEQ ID Nos. 79 (S124T/K511I/N589H/K712V/K853R/H946W), 80 (S124T/K511I/N589H/K786S/H946K/R113F), 81 (K511H/N589H/K853R/K102IL/D118E/DE11833), 82 (K95L/S124T/K511I/N589H), 83 (S124T/K511I/N589H/K7211/K786S/K1021V), 84 (S124T/K511H/N589H/K853R/H946K/K1054Y), 85 (K95T/S124T/N589H/K853R/K1052Q), and 86 (S124T/K511T/N589H/K712L/H946T/K1052Q/K1054N).

Example 15: Activity of MAD70-Series PAM Mutants in Mammalian Cells

Figure 14:
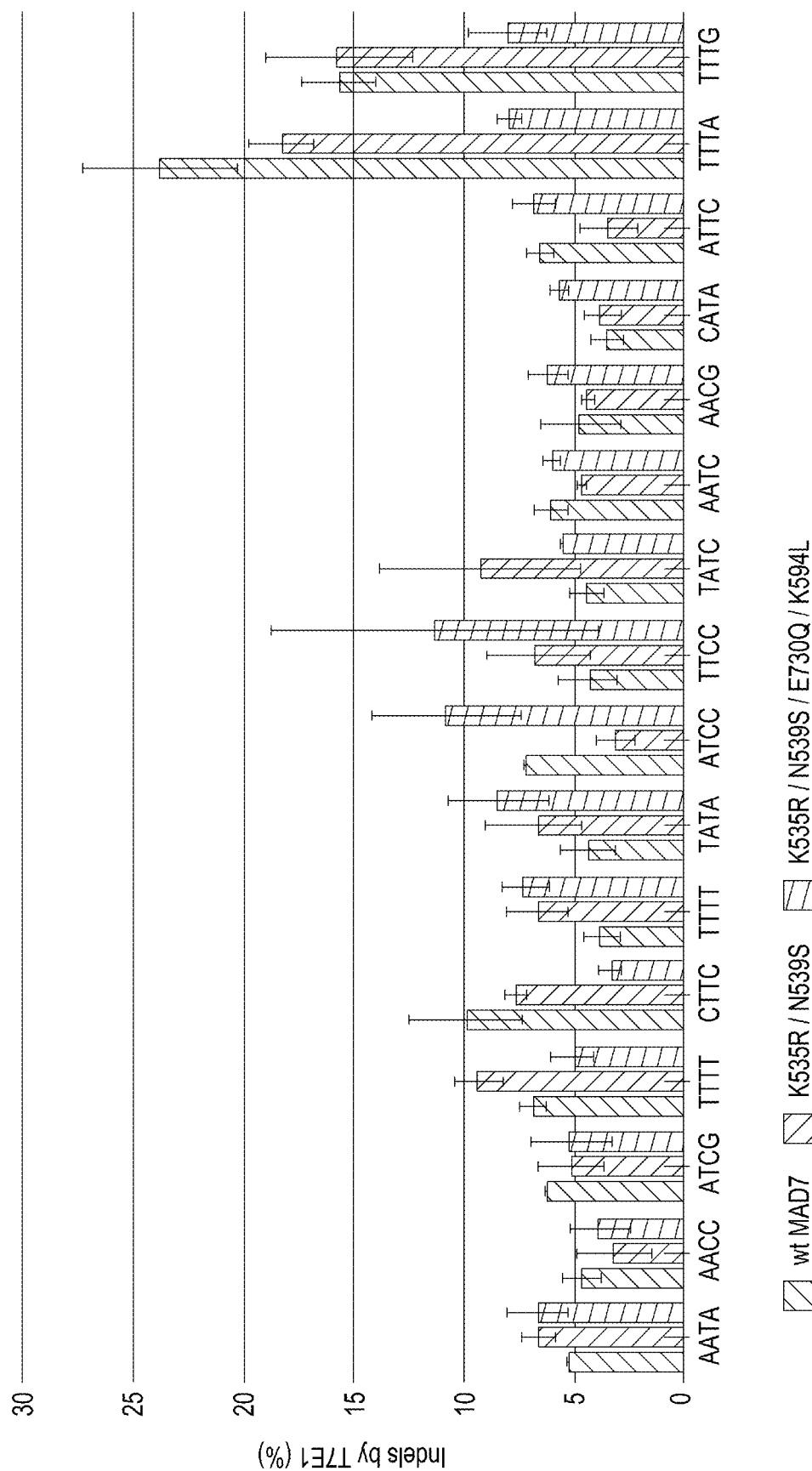
FIG. 14 shows the results of genome editing in mammalian HEK293T cells with wild-type MAD7 (SEQ ID No. 1) and MAD70-series variants with AsCas12a as a control.

Wild-type MAD7 and MAD70-series variants with altered PAM preference were cloned downstream of a CAG promoter for strong expression in mammalian cells. The vector sequence used for expression is provided in SEQ ID No. 89. Guide RNAs (gRNAs) targeting various PAMs were cloned downstream of a U6 promoter in the backbone vector sequence provided in SEQ ID No. 90. Transfections in HEK293T cells were performed using 100 ng of total DNA (gRNA/MAD70-series variant plasmid) and Lipofectamine 3000 transfection reagent. The transfection mix was added to cells that had been cultured in 96 well plates 24 hrs prior to transfection. To measure indels, T7E1 assay was performed. Cells were lysed by the addition of a buffer containing proteinase K and incubation at 56° C. for 30 minutes. Proteinase K was inactivated by heating the reaction to 95° C. for 10 minutes. Following lysis, 10 uL PCR reactions were performed using genomic template from lysed cells and 2× Q5 PCR mastermix (NEB) to amplify amplicons containing the target sites that were edited. Following PCR, the PCR fragments were heated to 95° C. C for 5 minutes and slowly cooled to room temperature. Then, T7 endonuclease I (NEB) was added to the PCR reaction and incubated for 1 hour at 37° C. The reaction was then resolved on 2.5% agarose gel and imaged using GelDoc (BioRad). The band intensities on the gel were quantified to calculate indels introduced by MAD7. The results are shown in FIG. 14. The MAD70-series mutant containing mutations K535R/N539S (SEQ ID No. 67) in reference to the wild-type MAD7 sequence shows substantially higher editing activity on TATC PAM while the K535R/N539S/K594L/E730Q (SEQ ID No. 68) mutant in relation to wild-type MAD7 shows higher editing on ATCC and TTCC PAMs.

TABLE 10

Sequences of spacers and the PAM sequences that were targeted in the PPIB locus

| Target # | PAM | Spacer Sequence | SEQ ID No. |
|---|---|---|---|
| 1 | CTTC | cctccctagcaacgcccctt | 53 |
| 2 | CATA | ggatttttaccgtcaccaaaa | 54 |
| 3 | AATA | tggctctattctctctcccat | 55 |

TABLE 10-continued

Sequences of spacers and the PAM sequences that were targeted in the PPIB locus

| Target # | PAM | Spacer Sequence | SEQ ID No. |
|---|---|---|---|
| 4 | ATCG | gctgaactctgcaggtcagtt | 56 |
| 5 | ATCC | tcaggttagcttcttgtacct | 57 |
| 6 | AATC | agattcagaaccacttctcta | 58 |
| 7 | TATC | ctgtagtccaaggagggtata | 59 |
| 8 | TATA | gataagcatgttttccaagaa | 60 |
| 9 | AACG | ccccttttaaagaagctaagtt | 61 |
| 10 | AACC | acttctctaaaaatatggctc | 62 |
| 11 | TTTT | tcagattcagaaccacttctc | 63 |
| 12 | TTTT | tatggctctattctctctccc | 64 |
| 13 | ATTC | tctctcccatcctcaggttag | 65 |
| 14 | TTCC | tcaggtgtattttgacctacg | 66 |

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. An engineered nucleic acid-guided nuclease with an altered fidelity relative to the nucleic acid-guided nuclease having the sequence of SEQ ID No. 1, wherein the engineered nucleic acid-guided nuclease has a sequence comprising any of SEQ ID Nos. 4-7.

2. The engineered nucleic acid-guided nuclease of claim 1 comprising SEQ ID No. 4.

3. The engineered nucleic acid-guided nuclease of claim 1 comprising SEQ ID No. 5.

4. The engineered nucleic acid-guided nuclease of claim 1 comprising SEQ ID No. 6.

5. The engineered nucleic acid-guided nuclease of claim 1 comprising SEQ ID No. 7.

6. An enzyme cocktail comprising an engineered nucleic acid-guided nuclease of claim 1.

7. An enzyme cocktail comprising an engineered nucleic acid-guided nuclease of claim 1 and SEQ ID No. 2.

8. An enzyme cocktail comprising an engineered nucleic acid-guided nuclease of claim 1 and SEQ ID No. 3.

9. An enzyme cocktail comprising an engineered nucleic acid-guided nuclease of claim 1 and SEQ ID No. 11.

10. An enzyme cocktail comprising an engineered nucleic acid-guided nuclease of claim 1 and SEQ ID No. 12.

11. An enzyme cocktail comprising an engineered nucleic acid-guided nuclease of claim 1 and SEQ ID No. 13.

12. An enzyme cocktail comprising an engineered nucleic acid-guided nuclease of claim 1 and SEQ ID No. 14.

13. An enzyme cocktail comprising an engineered nucleic acid-guided nuclease of claim 1 and SEQ ID No. 67.

14. An enzyme cocktail comprising an engineered nucleic acid-guided nuclease of claim 1 and SEQ ID No. 68.

* * * * *

SEQUENCE LISTING

<160> NUMBER OF SEQ ID NOS: 90

<210> SEQ ID NO 1
<211> LENGTH: 1263
<212> TYPE: PRT
<213> ORGANISM: Eubacterium rectale

<400> SEQUENCE: 1

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
                20                  25                  30

Gln Phe Ile Val Lys Asn Gly Ile Ile Lys Glu Asp Glu Leu Arg Gly
            35                  40                  45

Glu Asn Arg Gln Ile Leu Lys Asp Ile Met Asp Asp Tyr Tyr Arg Gly
        50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
                100                 105                 110

Phe Ala Asn Asp Asp Arg Phe Lys Asn Met Phe Ser Ala Lys Leu Ile
            115                 120                 125

Ser Asp Ile Leu Pro Glu Phe Val Ile His Asn Asn Asn Tyr Ser Ala

```
                130                 135                 140
    Ser Glu Lys Glu Glu Lys Thr Gln Val Ile Lys Leu Phe Ser Arg Phe
    145                 150                 155                 160

Ala Thr Ser Phe Lys Asp Tyr Phe Lys Asn Arg Ala Asn Cys Phe Ser
                    165                 170                 175

Ala Asp Asp Ile Ser Ser Ser Cys His Arg Ile Val Asn Asp Asn
                180                 185                 190

Ala Glu Ile Phe Phe Ser Asn Ala Leu Val Tyr Arg Arg Ile Val Lys
                195                 200                 205

Ser Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
    225                 230                 235                 240

Gly Glu Phe Ile Thr Gln Glu Gly Ile Ser Phe Tyr Asn Asp Ile Cys
                    245                 250                 255

Gly Lys Val Asn Ser Phe Met Asn Leu Tyr Cys Gln Lys Asn Lys Glu
                260                 265                 270

Asn Lys Asn Leu Tyr Lys Leu Gln Lys Leu His Lys Gln Ile Leu Cys
                275                 280                 285

Ile Ala Asp Thr Ser Tyr Glu Val Pro Tyr Lys Phe Glu Ser Asp Glu
    290                 295                 300

Glu Val Tyr Gln Ser Val Asn Gly Phe Leu Asp Asn Ile Ser Ser Lys
    305                 310                 315                 320

His Ile Val Glu Arg Leu Arg Lys Ile Gly Asp Asn Tyr Asn Gly Tyr
                    325                 330                 335

Asn Leu Asp Lys Ile Tyr Ile Val Ser Lys Phe Tyr Glu Ser Val Ser
                340                 345                 350

Gln Lys Thr Tyr Arg Asp Trp Glu Thr Ile Asn Thr Ala Leu Glu Ile
                355                 360                 365

His Tyr Asn Asn Ile Leu Pro Gly Asn Gly Lys Ser Lys Ala Asp Lys
    370                 375                 380

Val Lys Lys Ala Val Lys Asn Asp Leu Gln Lys Ser Ile Thr Glu Ile
    385                 390                 395                 400

Asn Glu Leu Val Ser Asn Tyr Lys Leu Cys Ser Asp Asp Asn Ile Lys
                    405                 410                 415

Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
                435                 440                 445

Leu Lys Ala Ser Glu Leu Lys Asn Val Leu Asp Val Ile Met Asn Ala
    450                 455                 460

Phe His Trp Cys Ser Val Phe Met Thr Glu Glu Leu Val Asp Lys Asp
    465                 470                 475                 480

Asn Asn Phe Tyr Ala Glu Leu Glu Glu Ile Tyr Asp Glu Ile Tyr Pro
                    485                 490                 495

Val Ile Ser Leu Tyr Asn Leu Val Arg Asn Tyr Val Thr Gln Lys Pro
                500                 505                 510

Tyr Ser Thr Lys Lys Ile Lys Leu Asn Phe Gly Ile Pro Thr Leu Ala
                515                 520                 525

Asp Gly Trp Ser Lys Ser Lys Glu Tyr Ser Asn Asn Ala Ile Ile Leu
    530                 535                 540

Met Arg Asp Asn Leu Tyr Tyr Leu Gly Ile Phe Asn Ala Lys Asn Lys
    545                 550                 555                 560
```

-continued

```
Pro Asp Lys Lys Ile Ile Gly Asn Thr Ser Glu Asn Lys Gly Asp
            565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
            595                 600                 605

Ser Ala Tyr Ile Leu Glu Gly Tyr Lys Gln Asn Lys His Ile Lys Ser
            610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
                660                 665                 670

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
            690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
            755                 760                 765

Thr Tyr Glu Ala Glu Gly Lys Asp Gln Phe Gly Asn Ile Gln Ile Val
            770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
                820                 825                 830

Arg Tyr Thr Tyr Asp Lys Tyr Phe Leu His Met Pro Ile Thr Ile Asn
            835                 840                 845

Phe Lys Ala Asn Lys Thr Gly Phe Ile Asn Asp Arg Ile Leu Gln Tyr
            850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
                900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975
```

-continued

```
Arg Gln Val Tyr Gln Lys Phe Glu Thr Met Leu Ile Asn Lys Leu Asn
                980                 985                 990

Tyr Leu Val Phe Lys Asp Ile Ser Ile Thr Glu Asn Gly Gly Leu Leu
            995                 1000                1005

Lys Gly Tyr Gln Leu Thr Tyr Ile Pro Asp Lys Leu Lys Asn Val
        1010                1015                1020

Gly His Gln Cys Gly Cys Ile Phe Tyr Val Pro Ala Ala Tyr Thr
        1025                1030                1035

Ser Lys Ile Asp Pro Thr Thr Gly Phe Val Asn Ile Phe Lys Phe
        1040                1045                1050

Lys Asp Leu Thr Val Asp Ala Lys Arg Glu Phe Ile Lys Lys Phe
        1055                1060                1065

Asp Ser Ile Arg Tyr Asp Ser Glu Lys Asn Leu Phe Cys Phe Thr
        1070                1075                1080

Phe Asp Tyr Asn Asn Phe Ile Thr Gln Asn Thr Val Met Ser Lys
        1085                1090                1095

Ser Ser Trp Ser Val Tyr Thr Tyr Gly Val Arg Ile Lys Arg Arg
        1100                1105                1110

Phe Val Asn Gly Arg Phe Ser Asn Glu Ser Asp Thr Ile Asp Ile
        1115                1120                1125

Thr Lys Asp Met Glu Lys Thr Leu Glu Met Thr Asp Ile Asn Trp
        1130                1135                1140

Arg Asp Gly His Asp Leu Arg Gln Asp Ile Ile Asp Tyr Glu Ile
        1145                1150                1155

Val Gln His Ile Phe Glu Ile Phe Arg Leu Thr Val Gln Met Arg
        1160                1165                1170

Asn Ser Leu Ser Glu Leu Glu Asp Arg Asp Tyr Asp Arg Leu Ile
        1175                1180                1185

Ser Pro Val Leu Asn Glu Asn Asn Ile Phe Tyr Asp Ser Ala Lys
        1190                1195                1200

Ala Gly Asp Ala Leu Pro Lys Asp Ala Asp Ala Asn Gly Ala Tyr
        1205                1210                1215

Cys Ile Ala Leu Lys Gly Leu Tyr Glu Ile Lys Gln Ile Thr Glu
        1220                1225                1230

Asn Trp Lys Glu Asp Gly Lys Phe Ser Arg Asp Lys Leu Lys Ile
        1235                1240                1245

Ser Asn Lys Asp Trp Phe Asp Phe Ile Gln Asn Lys Arg Tyr Leu
        1250                1255                1260
```

<210> SEQ ID NO 2
<211> LENGTH: 1263
<212> TYPE: PRT
<213> ORGANISM: Artificial Sequence
<220> FEATURE:
<223> OTHER INFORMATION: MAD70 VARIANT K535L

<400> SEQUENCE: 2

```
Met Asn Asn Gly Thr Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
                20                  25                  30

Gln Phe Ile Val Lys Asn Gly Ile Ile Lys Glu Asp Glu Leu Arg Gly
            35                  40                  45

Glu Asn Arg Gln Ile Leu Lys Asp Ile Met Asp Tyr Tyr Arg Gly
        50                  55                  60
```

```
Phe Ile Ser Glu Thr Leu Ser Ser Ile Asp Asp Ile Asp Trp Thr Ser
 65                  70                  75                  80

Leu Phe Glu Lys Met Glu Ile Gln Leu Lys Asn Gly Asp Asn Lys Asp
                 85                  90                  95

Thr Leu Ile Lys Glu Gln Thr Glu Tyr Arg Lys Ala Ile His Lys Lys
                100                 105                 110

Phe Ala Asn Asp Asp Arg Phe Lys Asn Met Phe Ser Ala Lys Leu Ile
                115                 120                 125

Ser Asp Ile Leu Pro Glu Phe Val Ile His Asn Asn Tyr Ser Ala
130                 135                 140

Ser Glu Lys Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
                180                 185                 190

Ala Glu Ile Phe Phe Ser Asn Ala Leu Val Tyr Arg Arg Ile Val Lys
                195                 200                 205

Ser Leu Ser Asn Asp Asp Ile Asn Lys Ile Ser Gly Asp Met Lys Asp
210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
                260                 265                 270

Asn Lys Asn Leu Tyr Lys Leu Gln Lys Leu His Lys Gln Ile Leu Cys
                275                 280                 285

Ile Ala Asp Thr Ser Tyr Glu Val Pro Tyr Lys Phe Glu Ser Asp Glu
                290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
                340                 345                 350

Gln Lys Thr Tyr Arg Asp Trp Glu Thr Ile Asn Thr Ala Leu Glu Ile
                355                 360                 365

His Tyr Asn Asn Ile Leu Pro Gly Asn Gly Lys Ser Lys Ala Asp Lys
                370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
                435                 440                 445

Leu Lys Ala Ser Glu Leu Lys Asn Val Leu Asp Val Ile Met Asn Ala
                450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
```

-continued

```
                485                 490                 495
Val Ile Ser Leu Tyr Asn Leu Val Arg Asn Tyr Val Thr Gln Lys Pro
                500                 505                 510

Tyr Ser Thr Lys Lys Ile Lys Leu Asn Phe Gly Ile Pro Thr Leu Ala
                515                 520                 525

Asp Gly Trp Ser Lys Ser Leu Glu Tyr Ser Asn Asn Ala Ile Ile Leu
            530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                    565                 570                 575

Tyr Lys Lys Met Ile Tyr Asn Leu Leu Pro Gly Pro Asn Lys Met Ile
                580                 585                 590

Pro Lys Val Phe Leu Ser Ser Lys Thr Gly Val Glu Thr Tyr Lys Pro
                595                 600                 605

Ser Ala Tyr Ile Leu Glu Gly Tyr Lys Gln Asn Lys His Ile Lys Ser
            610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                    645                 650                 655

Phe Ser Asp Thr Ser Thr Tyr Glu Asp Ile Ser Gly Phe Tyr Arg Glu
                660                 665                 670

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
            690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                    725                 730                 735

Val Leu Lys Leu Asn Gly Glu Ala Glu Ile Phe Phe Arg Lys Ser Ser
                740                 745                 750

Ile Lys Asn Pro Ile Ile His Lys Lys Gly Ser Ile Leu Val Asn Arg
            755                 760                 765

Thr Tyr Glu Ala Glu Glu Lys Asp Gln Phe Gly Asn Ile Gln Ile Val
            770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                    805                 810                 815

Asn Val Val Gly His His Glu Ala Ala Thr Asn Ile Val Lys Asp Tyr
                820                 825                 830

Arg Tyr Thr Tyr Asp Lys Tyr Phe Leu His Met Pro Ile Thr Ile Asn
            835                 840                 845

Phe Lys Ala Asn Lys Thr Gly Phe Ile Asn Asp Arg Ile Leu Gln Tyr
            850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                    885                 890                 895

Glu Gln Lys Ser Phe Asn Ile Val Asn Gly Tyr Asp Tyr Gln Ile Lys
                900                 905                 910
```

```
Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
        930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
            995                 1000                1005

Lys Gly Tyr Gln Leu Thr Tyr Ile Pro Asp Lys Leu Lys Asn Val
        1010                1015                1020

Gly His Gln Cys Gly Cys Ile Phe Tyr Val Pro Ala Ala Tyr Thr
        1025                1030                1035

Ser Lys Ile Asp Pro Thr Thr Gly Phe Val Asn Ile Phe Lys Phe
        1040                1045                1050

Lys Asp Leu Thr Val Asp Ala Lys Arg Glu Phe Ile Lys Lys Phe
        1055                1060                1065

Asp Ser Ile Arg Tyr Asp Ser Glu Lys Asn Leu Phe Cys Phe Thr
        1070                1075                1080

Phe Asp Tyr Asn Asn Phe Ile Thr Gln Asn Thr Val Met Ser Lys
        1085                1090                1095

Ser Ser Trp Ser Val Tyr Thr Tyr Gly Val Arg Ile Lys Arg Arg
        1100                1105                1110

Phe Val Asn Gly Arg Phe Ser Asn Glu Ser Asp Thr Ile Asp Ile
        1115                1120                1125

Thr Lys Asp Met Glu Lys Thr Leu Glu Met Thr Asp Ile Asn Trp
        1130                1135                1140

Arg Asp Gly His Asp Leu Arg Gln Asp Ile Ile Asp Tyr Glu Ile
        1145                1150                1155

Val Gln His Ile Phe Glu Ile Phe Arg Leu Thr Val Gln Met Arg
        1160                1165                1170

Asn Ser Leu Ser Glu Leu Glu Asp Arg Asp Tyr Asp Arg Leu Ile
        1175                1180                1185

Ser Pro Val Leu Asn Glu Asn Asn Ile Phe Tyr Asp Ser Ala Lys
        1190                1195                1200

Ala Gly Asp Ala Leu Pro Lys Asp Ala Asp Ala Asn Gly Ala Tyr
        1205                1210                1215

Cys Ile Ala Leu Lys Gly Leu Tyr Glu Ile Lys Gln Ile Thr Glu
        1220                1225                1230

Asn Trp Lys Glu Asp Gly Lys Phe Ser Arg Asp Lys Leu Lys Ile
        1235                1240                1245

Ser Asn Lys Asp Trp Phe Asp Phe Ile Gln Asn Lys Arg Tyr Leu
        1250                1255                1260

<210> SEQ ID NO 3
<211> LENGTH: 1263
<212> TYPE: PRT
<213> ORGANISM: Artificial Sequence
<220> FEATURE:
<223> OTHER INFORMATION: MAD70 VARIANT K594G

<400> SEQUENCE: 3
```

```
Met Asn Asn Gly Thr Asn Asn Phe Gln Asn Phe Ile Gly Ile Ser Ser
1               5                   10                  15
Leu Gln Lys Thr Leu Arg Asn Ala Leu Ile Pro Thr Glu Thr Thr Gln
                20                  25                  30
Gln Phe Ile Val Lys Asn Gly Ile Ile Lys Glu Asp Glu Leu Arg Gly
            35                  40                  45
Glu Asn Arg Gln Ile Leu Lys Asp Ile Met Asp Tyr Tyr Arg Gly
50                  55                  60
Phe Ile Ser Glu Thr Leu Ser Ser Ile Asp Asp Ile Asp Trp Thr Ser
65                  70                  75                  80
Leu Phe Glu Lys Met Glu Ile Gln Leu Lys Asn Gly Asp Asn Lys Asp
                85                  90                  95
Thr Leu Ile Lys Glu Gln Thr Glu Tyr Arg Lys Ala Ile His Lys Lys
            100                 105                 110
Phe Ala Asn Asp Asp Arg Phe Lys Asn Met Phe Ser Ala Lys Leu Ile
            115                 120                 125
Ser Asp Ile Leu Pro Glu Phe Val Ile His Asn Asn Asn Tyr Ser Ala
    130                 135                 140
Ser Glu Lys Glu Lys Thr Gln Val Ile Lys Leu Phe Ser Arg Phe
145                 150                 155                 160
Ala Thr Ser Phe Lys Asp Tyr Phe Lys Asn Arg Ala Asn Cys Phe Ser
                165                 170                 175
Ala Asp Asp Ile Ser Ser Ser Cys His Arg Ile Val Asn Asp Asn
            180                 185                 190
Ala Glu Ile Phe Phe Ser Asn Ala Leu Val Tyr Arg Arg Ile Val Lys
            195                 200                 205
Ser Leu Ser Asn Asp Asp Ile Asn Lys Ile Ser Gly Asp Met Lys Asp
    210                 215                 220
Ser Leu Lys Glu Met Ser Leu Glu Glu Ile Tyr Ser Tyr Glu Lys Tyr
225                 230                 235                 240
Gly Glu Phe Ile Thr Gln Glu Gly Ile Ser Phe Tyr Asn Asp Ile Cys
                245                 250                 255
Gly Lys Val Asn Ser Phe Met Asn Leu Tyr Cys Gln Lys Asn Lys Glu
            260                 265                 270
Asn Lys Asn Leu Tyr Lys Leu Gln Lys Leu His Lys Gln Ile Leu Cys
        275                 280                 285
Ile Ala Asp Thr Ser Tyr Glu Val Pro Tyr Lys Phe Glu Ser Asp Glu
    290                 295                 300
Glu Val Tyr Gln Ser Val Asn Gly Phe Leu Asp Asn Ile Ser Ser Lys
305                 310                 315                 320
His Ile Val Glu Arg Leu Arg Lys Ile Gly Asp Asn Tyr Asn Gly Tyr
                325                 330                 335
Asn Leu Asp Lys Ile Tyr Ile Val Ser Lys Phe Tyr Glu Ser Val Ser
            340                 345                 350
Gln Lys Thr Tyr Arg Asp Trp Glu Thr Ile Asn Thr Ala Leu Glu Ile
            355                 360                 365
His Tyr Asn Asn Ile Leu Pro Gly Asn Gly Lys Ser Lys Ala Asp Lys
    370                 375                 380
Val Lys Lys Ala Val Lys Asn Asp Leu Gln Lys Ser Ile Thr Glu Ile
385                 390                 395                 400
Asn Glu Leu Val Ser Asn Tyr Lys Leu Cys Ser Asp Asp Asn Ile Lys
                405                 410                 415
```

-continued

Ala Glu Thr Tyr Ile His Glu Ile Ser His Ile Leu Asn Asn Phe Glu
            420             425             430

Ala Gln Glu Leu Lys Tyr Asn Pro Glu Ile His Leu Val Glu Ser Glu
            435             440             445

Leu Lys Ala Ser Glu Leu Lys Asn Val Leu Asp Val Ile Met Asn Ala
            450             455             460

Phe His Trp Cys Ser Val Phe Met Thr Glu Glu Leu Val Asp Lys Asp
465             470             475             480

Asn Asn Phe Tyr Ala Glu Leu Glu Glu Ile Tyr Asp Glu Ile Tyr Pro
                485             490             495

Val Ile Ser Leu Tyr Asn Leu Val Arg Asn Tyr Val Thr Gln Lys Pro
            500             505             510

Tyr Ser Thr Lys Lys Ile Lys Leu Asn Phe Gly Ile Pro Thr Leu Ala
            515             520             525

Asp Gly Trp Ser Lys Ser Lys Glu Tyr Ser Asn Asn Ala Ile Ile Leu
            530             535             540

Met Arg Asp Asn Leu Tyr Tyr Leu Gly Ile Phe Asn Ala Lys Asn Lys
545             550             555             560

Pro Asp Lys Lys Ile Ile Glu Gly Asn Thr Ser Glu Asn Lys Gly Asp
                565             570             575

Tyr Lys Lys Met Ile Tyr Asn Leu Leu Pro Gly Pro Asn Lys Met Ile
            580             585             590

Pro Gly Val Phe Leu Ser Ser Lys Thr Gly Val Glu Thr Tyr Lys Pro
            595             600             605

Ser Ala Tyr Ile Leu Glu Gly Tyr Lys Gln Asn Lys His Ile Lys Ser
            610             615             620

Ser Lys Asp Phe Asp Ile Thr Phe Cys His Asp Leu Ile Asp Tyr Phe
625             630             635             640

Lys Asn Cys Ile Ala Ile His Pro Glu Trp Lys Asn Phe Gly Phe Asp
                645             650             655

Phe Ser Asp Thr Ser Thr Tyr Glu Asp Ile Ser Gly Phe Tyr Arg Glu
            660             665             670

Val Glu Leu Gln Gly Tyr Lys Ile Asp Trp Thr Tyr Ile Ser Glu Lys
            675             680             685

Asp Ile Asp Leu Leu Gln Glu Lys Gly Gln Leu Tyr Leu Phe Gln Ile
690             695             700

Tyr Asn Lys Asp Phe Ser Lys Lys Ser Thr Gly Asn Asp Asn Leu His
705             710             715             720

Thr Met Tyr Leu Lys Asn Leu Phe Ser Glu Glu Asn Leu Lys Asp Ile
            725             730             735

Val Leu Lys Leu Asn Gly Glu Ala Glu Ile Phe Phe Arg Lys Ser Ser
            740             745             750

Ile Lys Asn Pro Ile Ile His Lys Lys Gly Ser Ile Leu Val Asn Arg
            755             760             765

Thr Tyr Glu Ala Glu Glu Lys Asp Gln Phe Gly Asn Ile Gln Ile Val
            770             775             780

Arg Lys Asn Ile Pro Glu Asn Ile Tyr Gln Glu Leu Tyr Lys Tyr Phe
785             790             795             800

Asn Asp Lys Ser Asp Lys Glu Leu Ser Asp Glu Ala Ala Lys Leu Lys
                805             810             815

Asn Val Val Gly His His Glu Ala Ala Thr Asn Ile Val Lys Asp Tyr
            820             825             830

Arg Tyr Thr Tyr Asp Lys Tyr Phe Leu His Met Pro Ile Thr Ile Asn

```
              835                 840                 845
Phe Lys Ala Asn Lys Thr Gly Phe Ile Asn Asp Arg Ile Leu Gln Tyr
            850                 855                 860
Ile Ala Lys Glu Lys Asp Leu His Val Ile Gly Ile Asp Arg Gly Glu
865                 870                 875                 880
Arg Asn Leu Ile Tyr Val Ser Val Ile Asp Thr Cys Gly Asn Ile Val
                    885                 890                 895
Glu Gln Lys Ser Phe Asn Ile Val Asn Gly Tyr Asp Tyr Gln Ile Lys
                900                 905                 910
Leu Lys Gln Gln Glu Gly Ala Arg Gln Ile Ala Arg Lys Glu Trp Lys
                915                 920                 925
Glu Ile Gly Lys Ile Lys Glu Ile Lys Glu Gly Tyr Leu Ser Leu Val
            930                 935                 940
Ile His Glu Ile Ser Lys Met Val Ile Lys Tyr Asn Ala Ile Ile Ala
945                 950                 955                 960
Met Glu Asp Leu Ser Tyr Gly Phe Lys Lys Gly Arg Phe Lys Val Glu
                    965                 970                 975
Arg Gln Val Tyr Gln Lys Phe Glu Thr Met Leu Ile Asn Lys Leu Asn
                980                 985                 990
Tyr Leu Val Phe Lys Asp Ile Ser Ile Thr Glu Asn Gly Gly Leu Leu
                995                 1000                1005
Lys Gly Tyr Gln Leu Thr Tyr Ile Pro Asp Lys Leu Lys Asn Val
1010                1015                1020
Gly His Gln Cys Gly Cys Ile Phe Tyr Val Pro Ala Ala Tyr Thr
1025                1030                1035
Ser Lys Ile Asp Pro Thr Thr Gly Phe Val Asn Ile Phe Lys Phe
1040                1045                1050
Lys Asp Leu Thr Val Asp Ala Lys Arg Glu Phe Ile Lys Lys Phe
1055                1060                1065
Asp Ser Ile Arg Tyr Asp Ser Glu Lys Asn Leu Phe Cys Phe Thr
1070                1075                1080
Phe Asp Tyr Asn Asn Phe Ile Thr Gln Asn Thr Val Met Ser Lys
1085                1090                1095
Ser Ser Trp Ser Val Tyr Thr Tyr Gly Val Arg Ile Lys Arg Arg
1100                1105                1110
Phe Val Asn Gly Arg Phe Ser Asn Glu Ser Asp Thr Ile Asp Ile
1115                1120                1125
Thr Lys Asp Met Glu Lys Thr Leu Glu Met Thr Asp Ile Asn Trp
1130                1135                1140
Arg Asp Gly His Asp Leu Arg Gln Asp Ile Ile Asp Tyr Glu Ile
1145                1150                1155
Val Gln His Ile Phe Glu Ile Phe Arg Leu Thr Val Gln Met Arg
1160                1165                1170
Asn Ser Leu Ser Glu Leu Glu Asp Arg Asp Tyr Asp Arg Leu Ile
1175                1180                1185
Ser Pro Val Leu Asn Glu Asn Asn Ile Phe Tyr Asp Ser Ala Lys
1190                1195                1200
Ala Gly Asp Ala Leu Pro Lys Asp Ala Asp Ala Asn Gly Ala Tyr
1205                1210                1215
Cys Ile Ala Leu Lys Gly Leu Tyr Glu Ile Lys Gln Ile Thr Glu
1220                1225                1230
Asn Trp Lys Glu Asp Gly Lys Phe Ser Arg Asp Lys Leu Lys Ile
1235                1240                1245
```

```
Ser Asn Lys Asp Trp Phe Asp Phe Ile Gln Asn Lys Arg Tyr Leu
    1250                1255                1260

<210> SEQ ID NO 4
<211> LENGTH: 1263
<212> TYPE: PRT
<213> ORGANISM: Artificial Sequence
<220> FEATURE:
<223> OTHER INFORMATION: MAD70 VARIANT R920G

<400> SEQUENCE: 4

Met Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Gly Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Lys Leu His Lys Gln Ile Leu Cys
        275                 280                 285

Ile Ala Asp Thr Ser Tyr Glu Val Pro Tyr Lys Phe Glu Ser Asp Glu
    290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350
```

Gln Lys Thr Tyr Arg Asp Trp Glu Thr Ile Asn Thr Ala Leu Glu Ile
            355                 360                 365

His Tyr Asn Asn Ile Leu Pro Gly Asn Gly Lys Ser Lys Ala Asp Lys
    370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
            435                 440                 445

Leu Lys Ala Ser Glu Leu Lys Asn Val Leu Asp Val Ile Met Asn Ala
450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
                500                 505                 510

Tyr Ser Thr Lys Lys Ile Lys Leu Asn Phe Gly Ile Pro Thr Leu Ala
            515                 520                 525

Asp Gly Trp Ser Lys Ser Lys Glu Tyr Ser Asn Asn Ala Ile Ile Leu
            530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
            595                 600                 605

Ser Ala Tyr Ile Leu Glu Gly Tyr Lys Gln Asn Lys His Ile Lys Ser
    610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
                660                 665                 670

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
            755                 760                 765

```
Thr Tyr Glu Ala Glu Lys Asp Gln Phe Gly Asn Ile Gln Ile Val
770             775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
                835                 840                 845

Phe Lys Ala Asn Lys Thr Gly Phe Ile Asn Asp Arg Ile Leu Gln Tyr
850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
                900                 905                 910

Leu Lys Gln Gln Glu Gly Ala Gly Gln Ile Ala Arg Lys Glu Trp Lys
                915                 920                 925

Glu Ile Gly Lys Ile Lys Glu Ile Lys Glu Gly Tyr Leu Ser Leu Val
930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
                980                 985                 990

Tyr Leu Val Phe Lys Asp Ile Ser Ile Thr Glu Asn Gly Gly Leu Leu
            995                 1000                1005

Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
```

```
              1175                1180                1185

Ser Pro Val Leu Asn Glu Asn  Asn Ile Phe Tyr Asp  Ser Ala Lys
        1190                1195                1200

Ala Gly Asp Ala Leu Pro Lys  Asp Ala Asp Ala Asn  Gly Ala Tyr
        1205                1210                1215

Cys Ile Ala Leu Lys Gly Leu  Tyr Glu Ile Lys Gln  Ile Thr Glu
        1220                1225                1230

Asn Trp Lys Glu Asp Gly Lys  Phe Ser Arg Asp Lys  Leu Lys Ile
        1235                1240                1245

Ser Asn Lys Asp Trp Phe Asp  Phe Ile Gln Asn Lys  Arg Tyr Leu
        1250                1255                1260

<210> SEQ ID NO 5
<211> LENGTH: 1263
<212> TYPE: PRT
<213> ORGANISM: Artificial Sequence
<220> FEATURE:
<223> OTHER INFORMATION: MAD70 VARIANT R924I

<400> SEQUENCE: 5

Met Asn Asn Gly Thr Asn Asn  Phe Gln Asn Phe Ile  Gly Ile Ser Ser
1               5                       10                  15

Leu Gln Lys Thr Leu Arg Asn  Ala Leu Ile Pro Thr  Glu Thr Thr Gln
                20                      25                  30

Gln Phe Ile Val Lys Asn Gly  Ile Ile Lys Glu Asp  Glu Leu Arg Gly
            35                      40                  45

Glu Asn Arg Gln Ile Leu Lys  Asp Ile Met Asp Asp  Tyr Tyr Arg Gly
    50                      55                  60

Phe Ile Ser Glu Thr Leu Ser  Ser Ile Asp Asp Ile  Asp Trp Thr Ser
65                      70                  75                  80

Leu Phe Glu Lys Met Glu Ile  Gln Leu Lys Asn Gly  Asp Asn Lys Asp
                85                      90                  95

Thr Leu Ile Lys Glu Gln Thr  Glu Tyr Arg Lys Ala  Ile His Lys Lys
                100                     105                 110

Phe Ala Asn Asp Asp Arg Phe  Lys Asn Met Phe Ser  Ala Lys Leu Ile
            115                     120                 125

Ser Asp Ile Leu Pro Glu Phe  Val Ile His Asn Asn  Tyr Ser Ala
    130                     135                 140

Ser Glu Lys Glu Glu Lys Thr  Gln Val Ile Lys Leu  Phe Ser Arg Phe
145                     150                 155                 160

Ala Thr Ser Phe Lys Asp Tyr  Phe Lys Asn Arg Ala  Asn Cys Phe Ser
                165                     170                 175

Ala Asp Asp Ile Ser Ser Ser  Cys His Arg Ile Val  Asn Asp Asn
            180                     185                 190

Ala Glu Ile Phe Phe Ser Asn  Ala Leu Val Tyr Arg  Arg Ile Val Lys
        195                     200                 205

Ser Leu Ser Asn Asp Asp Ile  Asn Lys Ile Ser Gly  Asp Met Lys Asp
    210                     215                 220

Ser Leu Lys Glu Met Ser Leu  Glu Glu Ile Tyr Ser  Tyr Glu Lys Tyr
225                     230                 235                 240

Gly Glu Phe Ile Thr Gln Glu  Gly Ile Ser Phe Tyr  Asn Asp Ile Cys
                245                     250                 255

Gly Lys Val Asn Ser Phe Met  Asn Leu Tyr Cys Gln  Lys Asn Lys Glu
            260                     265                 270

Asn Lys Asn Leu Tyr Lys Leu  Gln Lys Leu His Lys  Gln Ile Leu Cys
```

```
            275                 280                 285
Ile Ala Asp Thr Ser Tyr Glu Val Pro Tyr Lys Phe Glu Ser Asp Glu
290                 295                 300
Glu Val Tyr Gln Ser Val Asn Gly Phe Leu Asp Asn Ile Ser Ser Lys
305                 310                 315                 320
His Ile Val Glu Arg Leu Arg Lys Ile Gly Asp Asn Tyr Asn Gly Tyr
                325                 330                 335
Asn Leu Asp Lys Ile Tyr Ile Val Ser Lys Phe Tyr Glu Ser Val Ser
                340                 345                 350
Gln Lys Thr Tyr Arg Asp Trp Glu Thr Ile Asn Thr Ala Leu Glu Ile
                355                 360                 365
His Tyr Asn Asn Ile Leu Pro Gly Asn Gly Lys Ser Lys Ala Asp Lys
        370                 375                 380
Val Lys Lys Ala Val Lys Asn Asp Leu Gln Lys Ser Ile Thr Glu Ile
385                 390                 395                 400
Asn Glu Leu Val Ser Asn Tyr Lys Leu Cys Ser Asp Asp Asn Ile Lys
                405                 410                 415
Ala Glu Thr Tyr Ile His Glu Ile Ser His Ile Leu Asn Asn Phe Glu
                420                 425                 430
Ala Gln Glu Leu Lys Tyr Asn Pro Glu Ile His Leu Val Glu Ser Glu
        435                 440                 445
Leu Lys Ala Ser Glu Leu Lys Asn Val Leu Asp Val Ile Met Asn Ala
        450                 455                 460
Phe His Trp Cys Ser Val Phe Met Thr Glu Glu Leu Val Asp Lys Asp
465                 470                 475                 480
Asn Asn Phe Tyr Ala Glu Leu Glu Glu Ile Tyr Asp Glu Ile Tyr Pro
                485                 490                 495
Val Ile Ser Leu Tyr Asn Leu Val Arg Asn Tyr Val Thr Gln Lys Pro
                500                 505                 510
Tyr Ser Thr Lys Lys Ile Lys Leu Asn Phe Gly Ile Pro Thr Leu Ala
                515                 520                 525
Asp Gly Trp Ser Lys Ser Lys Glu Tyr Ser Asn Asn Ala Ile Ile Leu
        530                 535                 540
Met Arg Asp Asn Leu Tyr Tyr Leu Gly Ile Phe Asn Ala Lys Asn Lys
545                 550                 555                 560
Pro Asp Lys Lys Ile Ile Glu Gly Asn Thr Ser Glu Asn Lys Gly Asp
                565                 570                 575
Tyr Lys Lys Met Ile Tyr Asn Leu Leu Pro Gly Pro Asn Lys Met Ile
                580                 585                 590
Pro Lys Val Phe Leu Ser Ser Lys Thr Gly Val Glu Thr Tyr Lys Pro
                595                 600                 605
Ser Ala Tyr Ile Leu Glu Gly Tyr Lys Gln Asn Lys His Ile Lys Ser
        610                 615                 620
Ser Lys Asp Phe Asp Ile Thr Phe Cys His Asp Leu Ile Asp Tyr Phe
625                 630                 635                 640
Lys Asn Cys Ile Ala Ile His Pro Glu Trp Lys Asn Phe Gly Phe Asp
                645                 650                 655
Phe Ser Asp Thr Ser Thr Tyr Glu Asp Ile Ser Gly Phe Tyr Arg Glu
                660                 665                 670
Val Glu Leu Gln Gly Tyr Lys Ile Asp Trp Thr Tyr Ile Ser Glu Lys
        675                 680                 685
Asp Ile Asp Leu Leu Gln Glu Lys Gly Gln Leu Tyr Leu Phe Gln Ile
        690                 695                 700
```

-continued

Tyr Asn Lys Asp Phe Ser Lys Ser Thr Gly Asn Asp Asn Leu His
705                 710                 715                 720

Thr Met Tyr Leu Lys Asn Leu Phe Ser Glu Glu Asn Leu Lys Asp Ile
            725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
        755                 760                 765

Thr Tyr Glu Ala Glu Glu Lys Asp Gln Phe Gly Asn Ile Gln Ile Val
    770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
            805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
        835                 840                 845

Phe Lys Ala Asn Lys Thr Gly Phe Ile Asn Asp Arg Ile Leu Gln Tyr
    850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
            885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Ile Lys Glu Trp Lys
        915                 920                 925

Glu Ile Gly Lys Ile Lys Glu Ile Lys Glu Gly Tyr Leu Ser Leu Val
    930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
            965                 970                 975

Arg Gln Val Tyr Gln Lys Phe Glu Thr Met Leu Ile Asn Lys Leu Asn
        980                 985                 990

Tyr Leu Val Phe Lys Asp Ile Ser Ile Thr Glu Asn Gly Gly Leu Leu
    995                 1000                1005

Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

```
Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 6
<211> LENGTH: 1263
<212> TYPE: PRT
<213> ORGANISM: Artificial Sequence
<220> FEATURE:
<223> OTHER INFORMATION: MAD70 VARIANT K511L

<400> SEQUENCE: 6

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205
```

```
Ser Leu Ser Asn Asp Asp Ile Asn Lys Ile Ser Gly Asp Met Lys Asp
    210                 215                 220
Ser Leu Lys Glu Met Ser Leu Glu Glu Ile Tyr Ser Tyr Glu Lys Tyr
225                 230                 235                 240
Gly Glu Phe Ile Thr Gln Glu Gly Ile Ser Phe Tyr Asn Asp Ile Cys
                245                 250                 255
Gly Lys Val Asn Ser Phe Met Asn Leu Tyr Cys Gln Lys Asn Lys Glu
            260                 265                 270
Asn Lys Asn Leu Tyr Lys Leu Gln Leu His Lys Gln Ile Leu Cys
        275                 280                 285
Ile Ala Asp Thr Ser Tyr Glu Val Pro Tyr Lys Phe Glu Ser Asp Glu
    290                 295                 300
Glu Val Tyr Gln Ser Val Asn Gly Phe Leu Asp Asn Ile Ser Ser Lys
305                 310                 315                 320
His Ile Val Glu Arg Leu Arg Lys Ile Gly Asp Asn Tyr Asn Gly Tyr
                325                 330                 335
Asn Leu Asp Lys Ile Tyr Ile Val Ser Lys Phe Tyr Glu Ser Val Ser
            340                 345                 350
Gln Lys Thr Tyr Arg Asp Trp Glu Thr Ile Asn Thr Ala Leu Glu Ile
        355                 360                 365
His Tyr Asn Asn Ile Leu Pro Gly Asn Gly Lys Ser Lys Ala Asp Lys
    370                 375                 380
Val Lys Lys Ala Val Lys Asn Asp Leu Gln Lys Ser Ile Thr Glu Ile
385                 390                 395                 400
Asn Glu Leu Val Ser Asn Tyr Lys Leu Cys Ser Asp Asp Asn Ile Lys
                405                 410                 415
Ala Glu Thr Tyr Ile His Glu Ile Ser His Ile Leu Asn Asn Phe Glu
            420                 425                 430
Ala Gln Glu Leu Lys Tyr Asn Pro Glu Ile His Leu Val Glu Ser Glu
        435                 440                 445
Leu Lys Ala Ser Glu Leu Lys Asn Val Leu Asp Val Ile Met Asn Ala
    450                 455                 460
Phe His Trp Cys Ser Val Phe Met Thr Glu Glu Leu Val Asp Lys Asp
465                 470                 475                 480
Asn Asn Phe Tyr Ala Glu Leu Glu Glu Ile Tyr Asp Glu Ile Tyr Pro
                485                 490                 495
Val Ile Ser Leu Tyr Asn Leu Val Arg Asn Tyr Val Thr Gln Leu Pro
            500                 505                 510
Tyr Ser Thr Lys Lys Ile Lys Leu Asn Phe Gly Ile Pro Thr Leu Ala
        515                 520                 525
Asp Gly Trp Ser Lys Ser Lys Glu Tyr Ser Asn Asn Ala Ile Ile Leu
    530                 535                 540
Met Arg Asp Asn Leu Tyr Tyr Leu Gly Ile Phe Asn Ala Lys Asn Lys
545                 550                 555                 560
Pro Asp Lys Lys Ile Ile Glu Gly Asn Thr Ser Glu Asn Lys Gly Asp
                565                 570                 575
Tyr Lys Lys Met Ile Tyr Asn Leu Leu Pro Gly Pro Asn Lys Met Ile
            580                 585                 590
Pro Lys Val Phe Leu Ser Ser Lys Thr Gly Val Glu Thr Tyr Lys Pro
        595                 600                 605
Ser Ala Tyr Ile Leu Glu Gly Tyr Lys Gln Asn Lys His Ile Lys Ser
    610                 615                 620
Ser Lys Asp Phe Asp Ile Thr Phe Cys His Asp Leu Ile Asp Tyr Phe
```

-continued

```
            625                 630                 635                 640
Lys Asn Cys Ile Ala Ile His Pro Glu Trp Lys Asn Phe Gly Phe Asp
                    645                 650                 655
Phe Ser Asp Thr Ser Thr Tyr Glu Asp Ile Ser Gly Phe Tyr Arg Glu
                    660                 665                 670
Val Glu Leu Gln Gly Tyr Lys Ile Asp Trp Thr Tyr Ile Ser Glu Lys
                    675                 680                 685
Asp Ile Asp Leu Leu Gln Glu Lys Gly Gln Leu Tyr Leu Phe Gln Ile
                    690                 695                 700
Tyr Asn Lys Asp Phe Ser Lys Lys Ser Thr Gly Asn Asp Asn Leu His
705                 710                 715                 720
Thr Met Tyr Leu Lys Asn Leu Phe Ser Glu Glu Asn Leu Lys Asp Ile
                    725                 730                 735
Val Leu Lys Leu Asn Gly Glu Ala Glu Ile Phe Phe Arg Lys Ser Ser
                    740                 745                 750
Ile Lys Asn Pro Ile Ile His Lys Lys Gly Ser Ile Leu Val Asn Arg
                    755                 760                 765
Thr Tyr Glu Ala Glu Lys Asp Gln Phe Gly Asn Ile Gln Ile Val
                    770                 775                 780
Arg Lys Asn Ile Pro Glu Asn Ile Tyr Gln Glu Leu Tyr Lys Tyr Phe
785                 790                 795                 800
Asn Asp Lys Ser Asp Lys Glu Leu Ser Asp Glu Ala Ala Lys Leu Lys
                    805                 810                 815
Asn Val Val Gly His His Glu Ala Ala Thr Asn Ile Val Lys Asp Tyr
                    820                 825                 830
Arg Tyr Thr Tyr Asp Lys Tyr Phe Leu His Met Pro Ile Thr Ile Asn
                    835                 840                 845
Phe Lys Ala Asn Lys Thr Gly Phe Ile Asn Asp Arg Ile Leu Gln Tyr
                    850                 855                 860
Ile Ala Lys Glu Lys Asp Leu His Val Ile Gly Ile Asp Arg Gly Glu
865                 870                 875                 880
Arg Asn Leu Ile Tyr Val Ser Val Ile Asp Thr Cys Gly Asn Ile Val
                    885                 890                 895
Glu Gln Lys Ser Phe Asn Ile Val Asn Gly Tyr Asp Tyr Gln Ile Lys
                    900                 905                 910
Leu Lys Gln Gln Glu Gly Ala Arg Gln Ile Ala Arg Lys Glu Trp Lys
                    915                 920                 925
Glu Ile Gly Lys Ile Lys Glu Ile Lys Glu Gly Tyr Leu Ser Leu Val
                    930                 935                 940
Ile His Glu Ile Ser Lys Met Val Ile Lys Tyr Asn Ala Ile Ile Ala
945                 950                 955                 960
Met Glu Asp Leu Ser Tyr Gly Phe Lys Lys Gly Arg Phe Lys Val Glu
                    965                 970                 975
Arg Gln Val Tyr Gln Lys Phe Glu Thr Met Leu Ile Asn Lys Leu Asn
                    980                 985                 990
Tyr Leu Val Phe Lys Asp Ile Ser Ile Thr Glu Asn Gly Gly Leu Leu
                    995                 1000                1005
Lys Gly Tyr Gln Leu Thr Tyr Ile Pro Asp Lys Leu Lys Asn Val
            1010                1015                1020
Gly His Gln Cys Gly Cys Ile Phe Tyr Val Pro Ala Ala Tyr Thr
            1025                1030                1035
Ser Lys Ile Asp Pro Thr Thr Gly Phe Val Asn Ile Phe Lys Phe
            1040                1045                1050
```

Lys Asp Leu Thr Val Asp Ala Lys Arg Glu Phe Ile Lys Lys Phe
             1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 7
<211> LENGTH: 1263
<212> TYPE: PRT
<213> ORGANISM: Artificial Sequence
<220> FEATURE:
<223> OTHER INFORMATION: MAD70 VARIANT H283T

<400> SEQUENCE: 7

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Tyr Ser Ala
        130                 135                 140

```
Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
            165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
            195                 200                 205

Ser Leu Ser Asn Asp Asp Ile Asn Lys Ile Ser Gly Asp Met Lys Asp
210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Lys Leu Thr Lys Gln Ile Leu Cys
        275                 280                 285

Ile Ala Asp Thr Ser Tyr Glu Val Pro Tyr Lys Phe Glu Ser Asp Glu
290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
            355                 360                 365

His Tyr Asn Asn Ile Leu Pro Gly Asn Gly Lys Ser Lys Ala Asp Lys
370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
            435                 440                 445

Leu Lys Ala Ser Glu Leu Lys Asn Val Leu Asp Val Ile Met Asn Ala
450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
            485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
            515                 520                 525

Asp Gly Trp Ser Lys Ser Lys Glu Tyr Ser Asn Asn Ala Ile Ile Leu
        530                 535                 540

Met Arg Asp Asn Leu Tyr Tyr Leu Gly Ile Phe Asn Ala Lys Asn Lys
545                 550                 555                 560
```

-continued

Pro Asp Lys Lys Ile Ile Glu Gly Asn Thr Ser Glu Asn Lys Gly Asp
            565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
            595                 600                 605

Ser Ala Tyr Ile Leu Glu Gly Tyr Lys Gln Asn Lys His Ile Lys Ser
            610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
            690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Asn Leu Lys Asp Ile
                725                 730                 735

Val Leu Lys Leu Asn Gly Glu Ala Glu Ile Phe Phe Arg Lys Ser Ser
                740                 745                 750

Ile Lys Asn Pro Ile Ile His Lys Lys Gly Ser Ile Leu Val Asn Arg
            755                 760                 765

Thr Tyr Glu Ala Glu Lys Asp Gln Phe Gly Asn Ile Gln Ile Val
            770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
            835                 840                 845

Phe Lys Ala Asn Lys Thr Gly Phe Ile Asn Asp Arg Ile Leu Gln Tyr
            850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn

```
            980             985             990
Tyr Leu Val Phe Lys Asp Ile Ser Ile Thr Glu Asn Gly Gly Leu Leu
                995             1000                1005

Lys Gly Tyr Gln Leu Thr Tyr Ile Pro Asp Lys Leu Lys Asn Val
        1010            1015                1020

Gly His Gln Cys Gly Cys Ile Phe Tyr Val Pro Ala Ala Tyr Thr
        1025            1030                1035

Ser Lys Ile Asp Pro Thr Thr Gly Phe Val Asn Ile Phe Lys Phe
        1040            1045                1050

Lys Asp Leu Thr Val Asp Ala Lys Arg Glu Phe Ile Lys Lys Phe
        1055            1060                1065

Asp Ser Ile Arg Tyr Asp Ser Glu Lys Asn Leu Phe Cys Phe Thr
        1070            1075                1080

Phe Asp Tyr Asn Asn Phe Ile Thr Gln Asn Thr Val Met Ser Lys
        1085            1090                1095

Ser Ser Trp Ser Val Tyr Thr Tyr Gly Val Arg Ile Lys Arg Arg
        1100            1105                1110

Phe Val Asn Gly Arg Phe Ser Asn Glu Ser Asp Thr Ile Asp Ile
        1115            1120                1125

Thr Lys Asp Met Glu Lys Thr Leu Glu Met Thr Asp Ile Asn Trp
        1130            1135                1140

Arg Asp Gly His Asp Leu Arg Gln Asp Ile Ile Asp Tyr Glu Ile
        1145            1150                1155

Val Gln His Ile Phe Glu Ile Phe Arg Leu Thr Val Gln Met Arg
        1160            1165                1170

Asn Ser Leu Ser Glu Leu Glu Asp Arg Asp Tyr Asp Arg Leu Ile
        1175            1180                1185

Ser Pro Val Leu Asn Glu Asn Asn Ile Phe Tyr Asp Ser Ala Lys
        1190            1195                1200

Ala Gly Asp Ala Leu Pro Lys Asp Ala Asp Ala Asn Gly Ala Tyr
        1205            1210                1215

Cys Ile Ala Leu Lys Gly Leu Tyr Glu Ile Lys Gln Ile Thr Glu
        1220            1225                1230

Asn Trp Lys Glu Asp Gly Lys Phe Ser Arg Asp Lys Leu Lys Ile
        1235            1240                1245

Ser Asn Lys Asp Trp Phe Asp Phe Ile Gln Asn Lys Arg Tyr Leu
        1250            1255                1260

<210> SEQ ID NO 8
<211> LENGTH: 1263
<212> TYPE: PRT
<213> ORGANISM: Artificial Sequence
<220> FEATURE:
<223> OTHER INFORMATION: MAD70 VARIANT R187K

<400> SEQUENCE: 8

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Lys Glu Asp Glu Leu Arg Gly
            35                  40                  45

Glu Asn Arg Gln Ile Leu Lys Asp Ile Met Asp Asp Tyr Tyr Arg Gly
        50                  55                  60

Phe Ile Ser Glu Thr Leu Ser Ser Ile Asp Asp Ile Asp Trp Thr Ser
```

```
            65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
                100                 105                 110

Phe Ala Asn Asp Asp Arg Phe Lys Asn Met Phe Ser Ala Lys Leu Ile
                115                 120                 125

Ser Asp Ile Leu Pro Glu Phe Val Ile His Asn Asn Tyr Ser Ala
130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Lys Ile Val Asn Asp Asn
                180                 185                 190

Ala Glu Ile Phe Phe Ser Asn Ala Leu Val Tyr Arg Arg Ile Val Lys
                195                 200                 205

Ser Leu Ser Asn Asp Asp Ile Asn Lys Ile Ser Gly Asp Met Lys Asp
                210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
                260                 265                 270

Asn Lys Asn Leu Tyr Lys Leu Gln Lys Leu His Lys Gln Ile Leu Cys
                275                 280                 285

Ile Ala Asp Thr Ser Tyr Glu Val Pro Tyr Lys Phe Glu Ser Asp Glu
                290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
                340                 345                 350

Gln Lys Thr Tyr Arg Asp Trp Glu Thr Ile Asn Thr Ala Leu Glu Ile
                355                 360                 365

His Tyr Asn Asn Ile Leu Pro Gly Asn Gly Lys Ser Lys Ala Asp Lys
                370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
                435                 440                 445

Leu Lys Ala Ser Glu Leu Lys Asn Val Leu Asp Val Ile Met Asn Ala
                450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495
```

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
            515                 520                 525

Asp Gly Trp Ser Lys Ser Lys Glu Tyr Ser Asn Asn Ala Ile Ile Leu
            530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
            565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
            595                 600                 605

Ser Ala Tyr Ile Leu Glu Gly Tyr Lys Gln Asn Lys His Ile Lys Ser
            610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
            645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
            690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
            725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
            755                 760                 765

Thr Tyr Glu Ala Glu Glu Lys Asp Gln Phe Gly Asn Ile Gln Ile Val
            770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
            805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
            835                 840                 845

Phe Lys Ala Asn Lys Thr Gly Phe Ile Asn Asp Arg Ile Leu Gln Tyr
            850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
            885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
          915                 920                 925

Glu Ile Gly Lys Ile Lys Glu Ile Lys Glu Gly Tyr Leu Ser Leu Val
          930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Gly Arg Phe Lys Val Glu
              965                 970                 975

Arg Gln Val Tyr Gln Lys Phe Glu Thr Met Leu Ile Asn Lys Leu Asn
          980                 985                 990

Tyr Leu Val Phe Lys Asp Ile Ser Ile Thr Glu Asn Gly Gly Leu Leu
          995                 1000                1005

Lys Gly Tyr Gln Leu Thr Tyr Ile Pro Asp Lys Leu Lys Asn Val
     1010                1015                1020

Gly His Gln Cys Gly Cys Ile Phe Tyr Val Pro Ala Ala Tyr Thr
     1025                1030                1035

Ser Lys Ile Asp Pro Thr Thr Gly Phe Val Asn Ile Phe Lys Phe
     1040                1045                1050

Lys Asp Leu Thr Val Asp Ala Lys Arg Glu Phe Ile Lys Lys Phe
     1055                1060                1065

Asp Ser Ile Arg Tyr Asp Ser Glu Lys Asn Leu Phe Cys Phe Thr
     1070                1075                1080

Phe Asp Tyr Asn Asn Phe Ile Thr Gln Asn Thr Val Met Ser Lys
     1085                1090                1095

Ser Ser Trp Ser Val Tyr Thr Tyr Gly Val Arg Ile Lys Arg Arg
     1100                1105                1110

Phe Val Asn Gly Arg Phe Ser Asn Glu Ser Asp Thr Ile Asp Ile
     1115                1120                1125

Thr Lys Asp Met Glu Lys Thr Leu Glu Met Thr Asp Ile Asn Trp
     1130                1135                1140

Arg Asp Gly His Asp Leu Arg Gln Asp Ile Ile Asp Tyr Glu Ile
     1145                1150                1155

Val Gln His Ile Phe Glu Ile Phe Arg Leu Thr Val Gln Met Arg
     1160                1165                1170

Asn Ser Leu Ser Glu Leu Glu Asp Arg Asp Tyr Asp Arg Leu Ile
     1175                1180                1185

Ser Pro Val Leu Asn Glu Asn Asn Ile Phe Tyr Asp Ser Ala Lys
     1190                1195                1200

Ala Gly Asp Ala Leu Pro Lys Asp Ala Asp Ala Asn Gly Ala Tyr
     1205                1210                1215

Cys Ile Ala Leu Lys Gly Leu Tyr Glu Ile Lys Gln Ile Thr Glu
     1220                1225                1230

Asn Trp Lys Glu Asp Gly Lys Phe Ser Arg Asp Lys Leu Lys Ile
     1235                1240                1245

Ser Asn Lys Asp Trp Phe Asp Phe Ile Gln Asn Lys Arg Tyr Leu
     1250                1255                1260

<210> SEQ ID NO 9
<211> LENGTH: 1263
<212> TYPE: PRT
<213> ORGANISM: Artificial Sequence
<220> FEATURE:
<223> OTHER INFORMATION: MAD70 VARIANT N589G

<400> SEQUENCE: 9

Met Asn Asn Gly Thr Asn Asn Phe Gln Asn Phe Ile Gly Ile Ser Ser
1               5                   10                  15
Leu Gln Lys Thr Leu Arg Asn Ala Leu Ile Pro Thr Glu Thr Thr Gln
            20                  25                  30
Gln Phe Ile Val Lys Asn Gly Ile Ile Lys Glu Asp Glu Leu Arg Gly
            35                  40                  45
Glu Asn Arg Gln Ile Leu Lys Asp Ile Met Asp Asp Tyr Tyr Arg Gly
50                  55                  60
Phe Ile Ser Glu Thr Leu Ser Ser Ile Asp Ile Asp Trp Thr Ser
65                  70                  75                  80
Leu Phe Glu Lys Met Glu Ile Gln Leu Lys Asn Gly Asp Asn Lys Asp
                85                  90                  95
Thr Leu Ile Lys Glu Gln Thr Glu Tyr Arg Lys Ala Ile His Lys Lys
            100                 105                 110
Phe Ala Asn Asp Asp Arg Phe Lys Asn Met Phe Ser Ala Lys Leu Ile
            115                 120                 125
Ser Asp Ile Leu Pro Glu Phe Val Ile His Asn Asn Tyr Ser Ala
130                 135                 140
Ser Glu Lys Glu Glu Lys Thr Gln Val Ile Lys Leu Phe Ser Arg Phe
145                 150                 155                 160
Ala Thr Ser Phe Lys Asp Tyr Phe Lys Asn Arg Ala Asn Cys Phe Ser
            165                 170                 175
Ala Asp Asp Ile Ser Ser Ser Cys His Arg Ile Val Asn Asp Asn
            180                 185                 190
Ala Glu Ile Phe Phe Ser Asn Ala Leu Val Tyr Arg Arg Ile Val Lys
            195                 200                 205
Ser Leu Ser Asn Asp Asp Ile Asn Lys Ile Ser Gly Asp Met Lys Asp
210                 215                 220
Ser Leu Lys Glu Met Ser Leu Glu Glu Ile Tyr Ser Tyr Glu Lys Tyr
225                 230                 235                 240
Gly Glu Phe Ile Thr Gln Glu Gly Ile Ser Phe Tyr Asn Asp Ile Cys
            245                 250                 255
Gly Lys Val Asn Ser Phe Met Asn Leu Tyr Cys Gln Lys Asn Lys Glu
            260                 265                 270
Asn Lys Asn Leu Tyr Lys Leu Gln Lys Leu His Lys Gln Ile Leu Cys
            275                 280                 285
Ile Ala Asp Thr Ser Tyr Glu Val Pro Tyr Lys Phe Glu Ser Asp Glu
            290                 295                 300
Glu Val Tyr Gln Ser Val Asn Gly Phe Leu Asp Asn Ile Ser Ser Lys
305                 310                 315                 320
His Ile Val Glu Arg Leu Arg Lys Ile Gly Asp Asn Tyr Asn Gly Tyr
            325                 330                 335
Asn Leu Asp Lys Ile Tyr Ile Val Ser Lys Phe Tyr Glu Ser Val Ser
            340                 345                 350
Gln Lys Thr Tyr Arg Asp Trp Glu Thr Ile Asn Thr Ala Leu Glu Ile
            355                 360                 365
His Tyr Asn Asn Ile Leu Pro Gly Asn Gly Lys Ser Lys Ala Asp Lys
            370                 375                 380
Val Lys Lys Ala Val Lys Asn Asp Leu Gln Lys Ser Ile Thr Glu Ile
385                 390                 395                 400
Asn Glu Leu Val Ser Asn Tyr Lys Leu Cys Ser Asp Asp Asn Ile Lys
            405                 410                 415
Ala Glu Thr Tyr Ile His Glu Ile Ser His Ile Leu Asn Asn Phe Glu

```
            420             425             430
Ala Gln Glu Leu Lys Tyr Asn Pro Glu Ile His Leu Val Glu Ser Glu
            435             440             445
Leu Lys Ala Ser Glu Leu Lys Asn Val Leu Asp Val Ile Met Asn Ala
            450             455             460
Phe His Trp Cys Ser Val Phe Met Thr Glu Glu Leu Val Asp Lys Asp
465             470             475             480
Asn Asn Phe Tyr Ala Glu Leu Glu Glu Ile Tyr Asp Glu Ile Tyr Pro
            485             490             495
Val Ile Ser Leu Tyr Asn Leu Val Arg Asn Tyr Val Thr Gln Lys Pro
            500             505             510
Tyr Ser Thr Lys Lys Ile Lys Leu Asn Phe Gly Ile Pro Thr Leu Ala
            515             520             525
Asp Gly Trp Ser Lys Ser Lys Glu Tyr Ser Asn Asn Ala Ile Ile Leu
            530             535             540
Met Arg Asp Asn Leu Tyr Tyr Leu Gly Ile Phe Asn Ala Lys Asn Lys
545             550             555             560
Pro Asp Lys Lys Ile Ile Glu Gly Asn Thr Ser Glu Asn Lys Gly Asp
            565             570             575
Tyr Lys Lys Met Ile Tyr Asn Leu Leu Pro Gly Pro Gly Lys Met Ile
            580             585             590
Pro Lys Val Phe Leu Ser Ser Lys Thr Gly Val Glu Thr Tyr Lys Pro
            595             600             605
Ser Ala Tyr Ile Leu Glu Gly Tyr Lys Gln Asn Lys His Ile Lys Ser
            610             615             620
Ser Lys Asp Phe Asp Ile Thr Phe Cys His Asp Leu Ile Asp Tyr Phe
625             630             635             640
Lys Asn Cys Ile Ala Ile His Pro Glu Trp Lys Asn Phe Gly Phe Asp
            645             650             655
Phe Ser Asp Thr Ser Thr Tyr Glu Asp Ile Ser Gly Phe Tyr Arg Glu
            660             665             670
Val Glu Leu Gln Gly Tyr Lys Ile Asp Trp Thr Tyr Ile Ser Glu Lys
            675             680             685
Asp Ile Asp Leu Leu Gln Glu Lys Gly Gln Leu Tyr Leu Phe Gln Ile
            690             695             700
Tyr Asn Lys Asp Phe Ser Lys Lys Ser Thr Gly Asn Asp Asn Leu His
705             710             715             720
Thr Met Tyr Leu Lys Asn Leu Phe Ser Glu Glu Asn Leu Lys Asp Ile
            725             730             735
Val Leu Lys Leu Asn Gly Glu Ala Glu Ile Phe Phe Arg Lys Ser Ser
            740             745             750
Ile Lys Asn Pro Ile Ile His Lys Gly Ser Ile Leu Val Asn Arg
            755             760             765
Thr Tyr Glu Ala Glu Lys Asp Gln Phe Gly Asn Ile Gln Ile Val
            770             775             780
Arg Lys Asn Ile Pro Glu Asn Ile Tyr Gln Glu Leu Tyr Lys Tyr Phe
785             790             795             800
Asn Asp Lys Ser Asp Lys Glu Leu Ser Asp Glu Ala Ala Lys Leu Lys
            805             810             815
Asn Val Val Gly His His Glu Ala Ala Thr Asn Ile Val Lys Asp Tyr
            820             825             830
Arg Tyr Thr Tyr Asp Lys Tyr Phe Leu His Met Pro Ile Thr Ile Asn
            835             840             845
```

-continued

Phe Lys Ala Asn Lys Thr Gly Phe Ile Asn Asp Arg Ile Leu Gln Tyr
    850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
                900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
        930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
        995                 1000                1005

Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 10
<211> LENGTH: 1263
<212> TYPE: PRT
<213> ORGANISM: Artificial Sequence
<220> FEATURE:
<223> OTHER INFORMATION: MAD70 VARIANT K281A

<400> SEQUENCE: 10

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Ala Leu His Lys Gln Ile Leu Cys
        275                 280                 285

Ile Ala Asp Thr Ser Tyr Glu Val Pro Tyr Lys Phe Glu Ser Asp Glu
    290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

```
Gln Lys Thr Tyr Arg Asp Trp Glu Thr Ile Asn Thr Ala Leu Glu Ile
            355                 360                 365

His Tyr Asn Asn Ile Leu Pro Gly Asn Gly Lys Ser Lys Ala Asp Lys
    370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
    450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
        515                 520                 525

Asp Gly Trp Ser Lys Ser Lys Glu Tyr Ser Asn Asn Ala Ile Ile Leu
    530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
        595                 600                 605

Ser Ala Tyr Ile Leu Glu Gly Tyr Lys Gln Asn Lys His Ile Lys Ser
    610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Ser Thr Gly Asn Asp Asn Leu His
705                 710                 715                 720

Thr Met Tyr Leu Lys Asn Leu Phe Ser Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
        755                 760                 765

Thr Tyr Glu Ala Glu Glu Lys Asp Gln Phe Gly Asn Ile Gln Ile Val
```

```
              770             775             780
Arg Lys Asn Ile Pro Glu Asn Ile Tyr Gln Glu Leu Tyr Lys Tyr Phe
785             790             795             800

Asn Asp Lys Ser Asp Lys Glu Leu Ser Asp Glu Ala Ala Lys Leu Lys
                805             810             815

Asn Val Val Gly His His Glu Ala Ala Thr Asn Ile Val Lys Asp Tyr
            820             825             830

Arg Tyr Thr Tyr Asp Lys Tyr Phe Leu His Met Pro Ile Thr Ile Asn
            835             840             845

Phe Lys Ala Asn Lys Thr Gly Phe Ile Asn Asp Arg Ile Leu Gln Tyr
850             855             860

Ile Ala Lys Glu Lys Asp Leu His Val Ile Gly Ile Asp Arg Gly Glu
865             870             875             880

Arg Asn Leu Ile Tyr Val Ser Val Ile Asp Thr Cys Gly Asn Ile Val
                885             890             895

Glu Gln Lys Ser Phe Asn Ile Val Asn Gly Tyr Asp Tyr Gln Ile Lys
                900             905             910

Leu Lys Gln Gln Glu Gly Ala Arg Gln Ile Ala Arg Lys Glu Trp Lys
            915             920             925

Glu Ile Gly Lys Ile Lys Glu Ile Lys Glu Gly Tyr Leu Ser Leu Val
930             935             940

Ile His Glu Ile Ser Lys Met Val Ile Lys Tyr Asn Ala Ile Ile Ala
945             950             955             960

Met Glu Asp Leu Ser Tyr Gly Phe Lys Lys Gly Arg Phe Lys Val Glu
                965             970             975

Arg Gln Val Tyr Gln Lys Phe Glu Thr Met Leu Ile Asn Lys Leu Asn
            980             985             990

Tyr Leu Val Phe Lys Asp Ile Ser Ile Thr Glu Asn Gly Gly Leu Leu
                995            1000            1005

Lys Gly Tyr Gln Leu Thr Tyr Ile Pro Asp Lys Leu Lys Asn Val
        1010            1015            1020

Gly His Gln Cys Gly Cys Ile Phe Tyr Val Pro Ala Ala Tyr Thr
        1025            1030            1035

Ser Lys Ile Asp Pro Thr Thr Gly Phe Val Asn Ile Phe Lys Phe
        1040            1045            1050

Lys Asp Leu Thr Val Asp Ala Lys Arg Glu Phe Ile Lys Lys Phe
        1055            1060            1065

Asp Ser Ile Arg Tyr Asp Ser Glu Lys Asn Leu Phe Cys Phe Thr
        1070            1075            1080

Phe Asp Tyr Asn Asn Phe Ile Thr Gln Asn Thr Val Met Ser Lys
        1085            1090            1095

Ser Ser Trp Ser Val Tyr Thr Tyr Gly Val Arg Ile Lys Arg Arg
        1100            1105            1110

Phe Val Asn Gly Arg Phe Ser Asn Glu Ser Asp Thr Ile Asp Ile
        1115            1120            1125

Thr Lys Asp Met Glu Lys Thr Leu Glu Met Thr Asp Ile Asn Trp
        1130            1135            1140

Arg Asp Gly His Asp Leu Arg Gln Asp Ile Ile Asp Tyr Glu Ile
        1145            1150            1155

Val Gln His Ile Phe Glu Ile Phe Arg Leu Thr Val Gln Met Arg
        1160            1165            1170

Asn Ser Leu Ser Glu Leu Glu Asp Arg Asp Tyr Asp Arg Leu Ile
        1175            1180            1185
```

-continued

```
Ser Pro Val Leu Asn Glu Asn Asn Ile Phe Tyr Asp Ser Ala Lys
    1190            1195                1200

Ala Gly Asp Ala Leu Pro Lys Asp Ala Asp Ala Asn Gly Ala Tyr
    1205            1210                1215

Cys Ile Ala Leu Lys Gly Leu Tyr Glu Ile Lys Gln Ile Thr Glu
    1220            1225                1230

Asn Trp Lys Glu Asp Gly Lys Phe Ser Arg Asp Lys Leu Lys Ile
    1235            1240                1245

Ser Asn Lys Asp Trp Phe Asp Phe Ile Gln Asn Lys Arg Tyr Leu
    1250            1255                1260
```

<210> SEQ ID NO 11
<211> LENGTH: 1263
<212> TYPE: PRT
<213> ORGANISM: Artificial Sequence
<220> FEATURE:
<223> OTHER INFORMATION: MAD70 VARIANT K535S

<400> SEQUENCE: 11

```
Met Asn Asn Gly Thr Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
                20                  25                  30

Gln Phe Ile Val Lys Asn Gly Ile Ile Lys Glu Asp Glu Leu Arg Gly
                35                  40                  45

Glu Asn Arg Gln Ile Leu Lys Asp Ile Met Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
                100                 105                 110

Phe Ala Asn Asp Asp Arg Phe Lys Asn Met Phe Ser Ala Lys Leu Ile
                115                 120                 125

Ser Asp Ile Leu Pro Glu Phe Val Ile His Asn Asn Asn Tyr Ser Ala
                130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Ser Cys His Arg Ile Val Asn Asp Asn
                180                 185                 190

Ala Glu Ile Phe Phe Ser Asn Ala Leu Val Tyr Arg Arg Ile Val Lys
                195                 200                 205

Ser Leu Ser Asn Asp Asp Ile Asn Lys Ile Ser Gly Asp Met Lys Asp
                210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
                260                 265                 270

Asn Lys Asn Leu Tyr Lys Leu Gln Lys Leu His Lys Gln Ile Leu Cys
                275                 280                 285
```

```
Ile Ala Asp Thr Ser Tyr Glu Val Pro Tyr Lys Phe Glu Ser Asp Glu
    290                 295                 300
Glu Val Tyr Gln Ser Val Asn Gly Phe Leu Asp Asn Ile Ser Ser Lys
305                 310                 315                 320
His Ile Val Glu Arg Leu Arg Lys Ile Gly Asp Asn Tyr Asn Gly Tyr
                325                 330                 335
Asn Leu Asp Lys Ile Tyr Ile Val Ser Lys Phe Tyr Glu Ser Val Ser
            340                 345                 350
Gln Lys Thr Tyr Arg Asp Trp Glu Thr Ile Asn Thr Ala Leu Glu Ile
        355                 360                 365
His Tyr Asn Asn Ile Leu Pro Gly Asn Gly Lys Ser Lys Ala Asp Lys
    370                 375                 380
Val Lys Lys Ala Val Lys Asn Asp Leu Gln Lys Ser Ile Thr Glu Ile
385                 390                 395                 400
Asn Glu Leu Val Ser Asn Tyr Lys Leu Cys Ser Asp Asp Asn Ile Lys
                405                 410                 415
Ala Glu Thr Tyr Ile His Glu Ile Ser His Ile Leu Asn Asn Phe Glu
            420                 425                 430
Ala Gln Glu Leu Lys Tyr Asn Pro Glu Ile His Leu Val Glu Ser Glu
        435                 440                 445
Leu Lys Ala Ser Glu Leu Lys Asn Val Leu Asp Val Ile Met Asn Ala
    450                 455                 460
Phe His Trp Cys Ser Val Phe Met Thr Glu Glu Leu Val Asp Lys Asp
465                 470                 475                 480
Asn Asn Phe Tyr Ala Glu Leu Glu Glu Ile Tyr Asp Glu Ile Tyr Pro
                485                 490                 495
Val Ile Ser Leu Tyr Asn Leu Val Arg Asn Tyr Val Thr Gln Lys Pro
            500                 505                 510
Tyr Ser Thr Lys Lys Ile Lys Leu Asn Phe Gly Ile Pro Thr Leu Ala
        515                 520                 525
Asp Gly Trp Ser Lys Ser Ser Glu Tyr Ser Asn Asn Ala Ile Ile Leu
    530                 535                 540
Met Arg Asp Asn Leu Tyr Tyr Leu Gly Ile Phe Asn Ala Lys Asn Lys
545                 550                 555                 560
Pro Asp Lys Lys Ile Ile Glu Gly Asn Thr Ser Glu Asn Lys Gly Asp
                565                 570                 575
Tyr Lys Lys Met Ile Tyr Asn Leu Leu Pro Gly Pro Asn Lys Met Ile
            580                 585                 590
Pro Lys Val Phe Leu Ser Ser Lys Thr Gly Val Glu Thr Tyr Lys Pro
        595                 600                 605
Ser Ala Tyr Ile Leu Glu Gly Tyr Lys Gln Asn Lys His Ile Lys Ser
    610                 615                 620
Ser Lys Asp Phe Asp Ile Thr Phe Cys His Asp Leu Ile Asp Tyr Phe
625                 630                 635                 640
Lys Asn Cys Ile Ala Ile His Pro Glu Trp Lys Asn Phe Gly Phe Asp
                645                 650                 655
Phe Ser Asp Thr Ser Thr Tyr Glu Asp Ile Ser Gly Phe Tyr Arg Glu
            660                 665                 670
Val Glu Leu Gln Gly Tyr Lys Ile Asp Trp Thr Tyr Ile Ser Glu Lys
        675                 680                 685
Asp Ile Asp Leu Leu Gln Glu Lys Gly Gln Leu Tyr Leu Phe Gln Ile
    690                 695                 700
```

```
Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
        755                 760                 765

Thr Tyr Glu Ala Glu Glu Lys Asp Gln Phe Gly Asn Ile Gln Ile Val
    770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
        835                 840                 845

Phe Lys Ala Asn Lys Thr Gly Phe Ile Asn Asp Arg Ile Leu Gln Tyr
    850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
    930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile  Ser Ile Thr Glu Asn Gly Gly Leu Leu
        995                 1000                1005

Lys Gly Tyr Gln Leu Thr Tyr  Ile Pro Asp Lys Leu  Lys Asn Val
    1010                1015                1020

Gly His Gln Cys Gly Cys Ile  Phe Tyr Val Pro Ala  Ala Tyr Thr
    1025                1030                1035

Ser Lys Ile Asp Pro Thr Thr  Gly Phe Val Asn Ile  Phe Lys Phe
    1040                1045                1050

Lys Asp Leu Thr Val Asp Ala Lys Arg Glu Phe Ile  Lys Lys Phe
    1055                1060                1065

Asp Ser Ile Arg Tyr Asp Ser  Glu Lys Asn Leu Phe  Cys Phe Thr
    1070                1075                1080

Phe Asp Tyr Asn Asn Phe Ile  Thr Gln Asn Thr Val  Met Ser Lys
    1085                1090                1095

Ser Ser Trp Ser Val Tyr Thr  Tyr Gly Val Arg Ile  Lys Arg Arg
    1100                1105                1110

Phe Val  Asn Gly Arg Phe Ser  Asn Glu Ser Asp Thr  Ile Asp Ile
```

-continued

```
                          1115                1120                1125

Thr Lys  Asp Met Glu Lys Thr  Leu Glu Met Thr Asp  Ile Asn Trp
         1130                1135                1140

Arg Asp  Gly His Asp Leu Arg  Gln Asp Ile Ile Asp  Tyr Glu Ile
         1145                1150                1155

Val Gln  His Ile Phe Glu Ile  Phe Arg Leu Thr Val  Gln Met Arg
         1160                1165                1170

Asn Ser  Leu Ser Glu Leu Glu  Asp Arg Asp Tyr Asp  Arg Leu Ile
         1175                1180                1185

Ser Pro  Val Leu Asn Glu Asn  Ile Phe Tyr Asp Ser  Ala Lys
         1190                1195                1200

Ala Gly  Asp Ala Leu Pro Lys  Asp Ala Asp Ala Asn  Gly Ala Tyr
         1205                1210                1215

Cys Ile  Ala Leu Lys Gly Leu  Tyr Glu Ile Lys Gln  Ile Thr Glu
         1220                1225                1230

Asn Trp  Lys Glu Asp Gly Lys  Phe Ser Arg Asp Lys  Leu Lys Ile
         1235                1240                1245

Ser Asn  Lys Asp Trp Phe Asp  Phe Ile Gln Asn Lys  Arg Tyr Leu
         1250                1255                1260
```

<210> SEQ ID NO 12
<211> LENGTH: 1263
<212> TYPE: PRT
<213> ORGANISM: Artificial Sequence
<220> FEATURE:
<223> OTHER INFORMATION: MAD70 VARIANT K535C

<400> SEQUENCE: 12

```
Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
```

```
             210                 215                 220
Ser Leu Lys Glu Met Ser Leu Glu Glu Ile Tyr Ser Tyr Glu Lys Tyr
225                 230                 235                 240

Gly Glu Phe Ile Thr Gln Gly Ile Ser Phe Tyr Asn Asp Ile Cys
                245                 250                 255

Gly Lys Val Asn Ser Phe Met Asn Leu Tyr Cys Gln Lys Asn Lys Glu
                260                 265                 270

Asn Lys Asn Leu Tyr Lys Leu Gln Lys Leu His Lys Gln Ile Leu Cys
                275                 280                 285

Ile Ala Asp Thr Ser Tyr Glu Val Pro Tyr Lys Phe Glu Ser Asp Glu
                290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
                340                 345                 350

Gln Lys Thr Tyr Arg Asp Trp Glu Thr Ile Asn Thr Ala Leu Glu Ile
                355                 360                 365

His Tyr Asn Asn Ile Leu Pro Gly Asn Gly Lys Ser Lys Ala Asp Lys
                370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
                435                 440                 445

Leu Lys Ala Ser Glu Leu Lys Asn Val Leu Asp Val Ile Met Asn Ala
                450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
                500                 505                 510

Tyr Ser Thr Lys Lys Ile Lys Leu Asn Phe Gly Ile Pro Thr Leu Ala
                515                 520                 525

Asp Gly Trp Ser Lys Ser Cys Glu Tyr Ser Asn Asn Ala Ile Ile Leu
                530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
                580                 585                 590

Pro Lys Val Phe Leu Ser Ser Lys Thr Gly Val Glu Thr Tyr Lys Pro
                595                 600                 605

Ser Ala Tyr Ile Leu Glu Gly Tyr Lys Gln Asn Lys His Ile Lys Ser
                610                 615                 620

Ser Lys Asp Phe Asp Ile Thr Phe Cys His Asp Leu Ile Asp Tyr Phe
625                 630                 635                 640
```

Lys Asn Cys Ile Ala Ile His Pro Glu Trp Lys Asn Phe Gly Phe Asp
            645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
            690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Asn Leu Lys Asp Ile
            725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
            755                 760                 765

Thr Tyr Glu Ala Glu Glu Lys Asp Gln Phe Gly Asn Ile Gln Ile Val
            770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
            805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
            835                 840                 845

Phe Lys Ala Asn Lys Thr Gly Phe Ile Asn Asp Arg Ile Leu Gln Tyr
            850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
            885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
            965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
            995                 1000                1005

Lys Gly Tyr Gln Leu Thr Tyr Ile Pro Asp Lys Leu Lys Asn Val
            1010                1015                1020

Gly His Gln Cys Gly Cys Ile Phe Tyr Val Pro Ala Ala Tyr Thr
            1025                1030                1035

Ser Lys Ile Asp Pro Thr Thr Gly Phe Val Asn Ile Phe Lys Phe
            1040                1045                1050

-continued

```
Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Phe Ile Gln Asn Lys Arg Tyr Leu
    1250                1255                1260

<210> SEQ ID NO 13
<211> LENGTH: 1263
<212> TYPE: PRT
<213> ORGANISM: Artificial Sequence
<220> FEATURE:
<223> OTHER INFORMATION: MAD70 VARIANT K535R

<400> SEQUENCE: 13

Met Asn Asn Gly Thr Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
                20                  25                  30

Gln Phe Ile Val Lys Asn Gly Ile Lys Glu Asp Glu Leu Arg Gly
                35                  40                  45

Glu Asn Arg Gln Ile Leu Lys Asp Ile Met Asp Asp Tyr Tyr Arg Gly
50                  55                      60

Phe Ile Ser Glu Thr Leu Ser Ser Ile Asp Ile Asp Trp Thr Ser
65                  70                  75                  80

Leu Phe Glu Lys Met Glu Ile Gln Leu Lys Asn Gly Asp Asn Lys Asp
                85                  90                      95

Thr Leu Ile Lys Glu Gln Thr Glu Tyr Arg Lys Ala Ile His Lys Lys
                100                 105                 110

Phe Ala Asn Asp Asp Arg Phe Lys Asn Met Phe Ser Ala Lys Leu Ile
                115                 120                 125

Ser Asp Ile Leu Pro Glu Phe Val Ile His Asn Asn Tyr Ser Ala
                130                 135                 140
```

```
Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
            165                 170                 175

Ala Asp Asp Ile Ser Ser Ser Cys His Arg Ile Val Asn Asp Asn
                180              185                 190

Ala Glu Ile Phe Phe Ser Asn Ala Leu Val Tyr Arg Arg Ile Val Lys
            195                 200                 205

Ser Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
                260                 265                 270

Asn Lys Asn Leu Tyr Lys Leu Gln Lys Leu His Lys Gln Ile Leu Cys
            275                 280                 285

Ile Ala Asp Thr Ser Tyr Glu Val Pro Tyr Lys Phe Glu Ser Asp Glu
290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
            355                 360                 365

His Tyr Asn Asn Ile Leu Pro Gly Asn Gly Lys Ser Lys Ala Asp Lys
370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
            435                 440                 445

Leu Lys Ala Ser Glu Leu Lys Asn Val Leu Asp Val Ile Met Asn Ala
450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
            515                 520                 525

Asp Gly Trp Ser Lys Ser Arg Glu Tyr Ser Asn Asn Ala Ile Ile Leu
            530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
```

-continued

```
            565                 570                 575
Tyr Lys Lys Met Ile Tyr Asn Leu Leu Pro Gly Pro Asn Lys Met Ile
            580                 585                 590
Pro Lys Val Phe Leu Ser Ser Lys Thr Gly Val Glu Thr Tyr Lys Pro
            595                 600                 605
Ser Ala Tyr Ile Leu Glu Gly Tyr Lys Gln Asn Lys His Ile Lys Ser
            610                 615                 620
Ser Lys Asp Phe Asp Ile Thr Phe Cys His Asp Leu Ile Asp Tyr Phe
625                 630                 635                 640
Lys Asn Cys Ile Ala Ile His Pro Glu Trp Lys Asn Phe Gly Phe Asp
                    645                 650                 655
Phe Ser Asp Thr Ser Thr Tyr Glu Asp Ile Ser Gly Phe Tyr Arg Glu
                    660                 665                 670
Val Glu Leu Gln Gly Tyr Lys Ile Asp Trp Thr Tyr Ile Ser Glu Lys
                    675                 680                 685
Asp Ile Asp Leu Leu Gln Glu Lys Gly Gln Leu Tyr Leu Phe Gln Ile
                    690                 695                 700
Tyr Asn Lys Asp Phe Ser Lys Lys Ser Thr Gly Asn Asp Asn Leu His
705                 710                 715                 720
Thr Met Tyr Leu Lys Asn Leu Phe Ser Glu Asn Leu Lys Asp Ile
                    725                 730                 735
Val Leu Lys Leu Asn Gly Glu Ala Glu Ile Phe Phe Arg Lys Ser Ser
                    740                 745                 750
Ile Lys Asn Pro Ile Ile His Lys Lys Gly Ser Ile Leu Val Asn Arg
                    755                 760                 765
Thr Tyr Glu Ala Glu Lys Asp Gln Phe Gly Asn Ile Gln Ile Val
                    770                 775                 780
Arg Lys Asn Ile Pro Glu Asn Ile Tyr Gln Glu Leu Tyr Lys Tyr Phe
785                 790                 795                 800
Asn Asp Lys Ser Asp Lys Glu Leu Ser Asp Glu Ala Ala Lys Leu Lys
                    805                 810                 815
Asn Val Val Gly His His Glu Ala Ala Thr Asn Ile Val Lys Asp Tyr
                    820                 825                 830
Arg Tyr Thr Tyr Asp Lys Tyr Phe Leu His Met Pro Ile Thr Ile Asn
                    835                 840                 845
Phe Lys Ala Asn Lys Thr Gly Phe Ile Asn Asp Arg Ile Leu Gln Tyr
                    850                 855                 860
Ile Ala Lys Glu Lys Asp Leu His Val Ile Gly Ile Asp Arg Gly Glu
865                 870                 875                 880
Arg Asn Leu Ile Tyr Val Ser Val Ile Asp Thr Cys Gly Asn Ile Val
                    885                 890                 895
Glu Gln Lys Ser Phe Asn Ile Val Asn Gly Tyr Asp Tyr Gln Ile Lys
                    900                 905                 910
Leu Lys Gln Gln Glu Gly Ala Arg Gln Ile Ala Arg Lys Glu Trp Lys
                    915                 920                 925
Glu Ile Gly Lys Ile Lys Glu Ile Lys Glu Gly Tyr Leu Ser Leu Val
                    930                 935                 940
Ile His Glu Ile Ser Lys Met Val Ile Lys Tyr Asn Ala Ile Ile Ala
945                 950                 955                 960
Met Glu Asp Leu Ser Tyr Gly Phe Lys Lys Gly Arg Phe Lys Val Glu
                    965                 970                 975
Arg Gln Val Tyr Gln Lys Phe Glu Thr Met Leu Ile Asn Lys Leu Asn
                    980                 985                 990
```

```
Tyr Leu Val Phe Lys Asp Ile Ser  Ile Thr Glu Asn Gly  Gly Leu Leu
            995                 1000                1005

Lys Gly Tyr Gln Leu Thr Tyr  Ile Pro Asp Lys Leu  Lys Asn Val
    1010                1015                1020

Gly His Gln Cys Gly Cys Ile  Phe Tyr Val Pro Ala  Ala Tyr Thr
    1025                1030                1035

Ser Lys Ile Asp Pro Thr Thr  Gly Phe Val Asn Ile  Phe Lys Phe
    1040                1045                1050

Lys Asp Leu Thr Val Asp Ala  Lys Arg Glu Phe Ile  Lys Lys Phe
    1055                1060                1065

Asp Ser Ile Arg Tyr Asp Ser  Glu Lys Asn Leu Phe  Cys Phe Thr
    1070                1075                1080

Phe Asp Tyr Asn Asn Phe Ile  Thr Gln Asn Thr Val  Met Ser Lys
    1085                1090                1095

Ser Ser Trp Ser Val Tyr Thr  Tyr Gly Val Arg Ile  Lys Arg Arg
    1100                1105                1110

Phe Val Asn Gly Arg Phe Ser  Asn Glu Ser Asp Thr  Ile Asp Ile
    1115                1120                1125

Thr Lys Asp Met Glu Lys Thr  Leu Glu Met Thr Asp  Ile Asn Trp
    1130                1135                1140

Arg Asp Gly His Asp Leu Arg  Gln Asp Ile Ile Asp  Tyr Glu Ile
    1145                1150                1155

Val Gln His Ile Phe Glu Ile  Phe Arg Leu Thr Val  Gln Met Arg
    1160                1165                1170

Asn Ser Leu Ser Glu Leu Glu  Asp Arg Asp Tyr Asp  Arg Leu Ile
    1175                1180                1185

Ser Pro Val Leu Asn Glu Asn  Asn Ile Phe Tyr Asp  Ser Ala Lys
    1190                1195                1200

Ala Gly Asp Ala Leu Pro Lys  Asp Ala Asp Ala Asn  Gly Ala Tyr
    1205                1210                1215

Cys Ile Ala Leu Lys Gly Leu  Tyr Glu Ile Lys Gln  Ile Thr Glu
    1220                1225                1230

Asn Trp Lys Glu Asp Gly Lys  Phe Ser Arg Asp Lys  Leu Lys Ile
    1235                1240                1245

Ser Asn Lys Asp Trp Phe Asp  Phe Ile Gln Asn Lys  Arg Tyr Leu
    1250                1255                1260

<210> SEQ ID NO 14
<211> LENGTH: 1263
<212> TYPE: PRT
<213> ORGANISM: Artificial Sequence
<220> FEATURE:
<223> OTHER INFORMATION: MAD70 VARIANT K535N

<400> SEQUENCE: 14

Met Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
65                  70                  75                  80
```

-continued

```
Leu Phe Glu Lys Met Glu Ile Gln Leu Lys Asn Gly Asp Asn Lys Asp
                 85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
            115                 120                 125

Ser Asp Ile Leu Pro Glu Phe Val Ile His Asn Asn Tyr Ser Ala
130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
            195                 200                 205

Ser Leu Ser Asn Asp Asp Ile Asn Lys Ile Ser Gly Asp Met Lys Asp
210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Lys Leu His Lys Gln Ile Leu Cys
            275                 280                 285

Ile Ala Asp Thr Ser Tyr Glu Val Pro Tyr Lys Phe Glu Ser Asp Glu
            290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
            355                 360                 365

His Tyr Asn Asn Ile Leu Pro Gly Asn Gly Lys Ser Lys Ala Asp Lys
            370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
            435                 440                 445

Leu Lys Ala Ser Glu Leu Lys Asn Val Leu Asp Val Ile Met Asn Ala
450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495
```

-continued

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
    515                 520                 525

Asp Gly Trp Ser Lys Ser Asn Glu Tyr Ser Asn Asn Ala Ile Ile Leu
    530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
            595                 600                 605

Ser Ala Tyr Ile Leu Glu Gly Tyr Lys Gln Asn Lys His Ile Lys Ser
    610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
    675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
    755                 760                 765

Thr Tyr Glu Ala Glu Glu Lys Asp Gln Phe Gly Asn Ile Gln Ile Val
    770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
    835                 840                 845

Phe Lys Ala Asn Lys Thr Gly Phe Ile Asn Asp Arg Ile Leu Gln Tyr
    850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys

-continued

```
                915                 920                 925
Glu Ile Gly Lys Ile Lys Glu Ile Lys Glu Gly Tyr Leu Ser Leu Val
        930                 935                 940
Ile His Glu Ile Ser Lys Met Val Ile Lys Tyr Asn Ala Ile Ile Ala
945                 950                 955                 960
Met Glu Asp Leu Ser Tyr Gly Phe Lys Gly Arg Phe Lys Val Glu
                965                 970                 975
Arg Gln Val Tyr Gln Lys Phe Glu Thr Met Leu Ile Asn Lys Leu Asn
            980                 985                 990
Tyr Leu Val Phe Lys Asp Ile Ser Ile Thr Glu Asn Gly Gly Leu Leu
            995                1000                1005
Lys Gly Tyr Gln Leu Thr Tyr Ile Pro Asp Lys Leu Lys Asn Val
1010                1015                1020
Gly His Gln Cys Gly Cys Ile Phe Tyr Val Pro Ala Ala Tyr Thr
    1025                1030                1035
Ser Lys Ile Asp Pro Thr Thr Gly Phe Val Asn Ile Phe Lys Phe
    1040                1045                1050
Lys Asp Leu Thr Val Asp Ala Lys Arg Glu Phe Ile Lys Lys Phe
    1055                1060                1065
Asp Ser Ile Arg Tyr Asp Ser Glu Lys Asn Leu Phe Cys Phe Thr
    1070                1075                1080
Phe Asp Tyr Asn Asn Phe Ile Thr Gln Asn Thr Val Met Ser Lys
    1085                1090                1095
Ser Ser Trp Ser Val Tyr Thr Tyr Gly Val Arg Ile Lys Arg Arg
    1100                1105                1110
Phe Val Asn Gly Arg Phe Ser Asn Glu Ser Asp Thr Ile Asp Ile
    1115                1120                1125
Thr Lys Asp Met Glu Lys Thr Leu Glu Met Thr Asp Ile Asn Trp
    1130                1135                1140
Arg Asp Gly His Asp Leu Arg Gln Asp Ile Ile Asp Tyr Glu Ile
    1145                1150                1155
Val Gln His Ile Phe Glu Ile Phe Arg Leu Thr Val Gln Met Arg
    1160                1165                1170
Asn Ser Leu Ser Glu Leu Glu Asp Arg Asp Tyr Asp Arg Leu Ile
    1175                1180                1185
Ser Pro Val Leu Asn Glu Asn Asn Ile Phe Tyr Asp Ser Ala Lys
    1190                1195                1200
Ala Gly Asp Ala Leu Pro Lys Asp Ala Asp Ala Asn Gly Ala Tyr
    1205                1210                1215
Cys Ile Ala Leu Lys Gly Leu Tyr Glu Ile Lys Gln Ile Thr Glu
    1220                1225                1230
Asn Trp Lys Glu Asp Gly Lys Phe Ser Arg Asp Lys Leu Lys Ile
    1235                1240                1245
Ser Asn Lys Asp Trp Phe Asp Phe Ile Gln Asn Lys Arg Tyr Leu
    1250                1255                1260
```

<210> SEQ ID NO 15
<211> LENGTH: 1263
<212> TYPE: PRT
<213> ORGANISM: Artificial Sequence
<220> FEATURE:
<223> OTHER INFORMATION: MAD70 VARIANT K281V

<400> SEQUENCE: 15

Met Asn Asn Gly Thr Asn Phe Gln Asn Phe Ile Gly Ile Ser Ser

-continued

```
1               5                    10                   15
Leu Gln Lys Thr Leu Arg Asn Ala Leu Ile Pro Thr Glu Thr Thr Gln
                20                  25                  30
Gln Phe Ile Val Lys Asn Gly Ile Ile Lys Glu Asp Glu Leu Arg Gly
                35                  40                  45
Glu Asn Arg Gln Ile Leu Lys Asp Ile Met Asp Tyr Tyr Arg Gly
        50                  55                  60
Phe Ile Ser Glu Thr Leu Ser Ser Ile Asp Asp Ile Asp Trp Thr Ser
65                  70                  75                  80
Leu Phe Glu Lys Met Glu Ile Gln Leu Lys Asn Gly Asp Asn Lys Asp
                    85                  90                  95
Thr Leu Ile Lys Glu Gln Thr Glu Tyr Arg Lys Ala Ile His Lys Lys
                100                 105                 110
Phe Ala Asn Asp Asp Arg Phe Lys Asn Met Phe Ser Ala Lys Leu Ile
                115                 120                 125
Ser Asp Ile Leu Pro Glu Phe Val Ile His Asn Asn Tyr Ser Ala
        130                 135                 140
Ser Glu Lys Glu Glu Lys Thr Gln Val Ile Lys Leu Phe Ser Arg Phe
145                 150                 155                 160
Ala Thr Ser Phe Lys Asp Tyr Phe Lys Asn Arg Ala Asn Cys Phe Ser
                    165                 170                 175
Ala Asp Asp Ile Ser Ser Ser Cys His Arg Ile Val Asn Asp Asn
        180                 185                 190
Ala Glu Ile Phe Phe Ser Asn Ala Leu Val Tyr Arg Arg Ile Val Lys
                195                 200                 205
Ser Leu Ser Asn Asp Asp Ile Asn Lys Ile Ser Gly Asp Met Lys Asp
210                 215                 220
Ser Leu Lys Glu Met Ser Leu Glu Glu Ile Tyr Ser Tyr Glu Lys Tyr
225                 230                 235                 240
Gly Glu Phe Ile Thr Gln Glu Gly Ile Ser Phe Tyr Asn Asp Ile Cys
                    245                 250                 255
Gly Lys Val Asn Ser Phe Met Asn Leu Tyr Cys Gln Lys Asn Lys Glu
                260                 265                 270
Asn Lys Asn Leu Tyr Lys Leu Gln Val Leu His Lys Gln Ile Leu Cys
                275                 280                 285
Ile Ala Asp Thr Ser Tyr Glu Val Pro Tyr Lys Phe Glu Ser Asp Glu
        290                 295                 300
Glu Val Tyr Gln Ser Val Asn Gly Phe Leu Asp Asn Ile Ser Ser Lys
305                 310                 315                 320
His Ile Val Glu Arg Leu Arg Lys Ile Gly Asp Asn Tyr Asn Gly Tyr
                    325                 330                 335
Asn Leu Asp Lys Ile Tyr Ile Val Ser Lys Phe Tyr Glu Ser Val Ser
                340                 345                 350
Gln Lys Thr Tyr Arg Asp Trp Glu Thr Ile Asn Thr Ala Leu Glu Ile
                355                 360                 365
His Tyr Asn Asn Ile Leu Pro Gly Asn Gly Lys Ser Lys Ala Asp Lys
        370                 375                 380
Val Lys Lys Ala Val Lys Asn Asp Leu Gln Lys Ser Ile Thr Glu Ile
385                 390                 395                 400
Asn Glu Leu Val Ser Asn Tyr Lys Leu Cys Ser Asp Asp Asn Ile Lys
                    405                 410                 415
Ala Glu Thr Tyr Ile His Glu Ile Ser His Ile Leu Asn Asn Phe Glu
                420                 425                 430
```

```
Ala Gln Glu Leu Lys Tyr Asn Pro Glu Ile His Leu Val Glu Ser Glu
        435                 440                 445
Leu Lys Ala Ser Glu Leu Lys Asn Val Leu Asp Val Ile Met Asn Ala
450                 455                 460
Phe His Trp Cys Ser Val Phe Met Thr Glu Glu Leu Val Asp Lys Asp
465                 470                 475                 480
Asn Asn Phe Tyr Ala Glu Leu Glu Glu Ile Tyr Asp Glu Ile Tyr Pro
                485                 490                 495
Val Ile Ser Leu Tyr Asn Leu Val Arg Asn Tyr Val Thr Gln Lys Pro
            500                 505                 510
Tyr Ser Thr Lys Lys Ile Lys Leu Asn Phe Gly Ile Pro Thr Leu Ala
        515                 520                 525
Asp Gly Trp Ser Lys Ser Lys Glu Tyr Ser Asn Asn Ala Ile Ile Leu
    530                 535                 540
Met Arg Asp Asn Leu Tyr Tyr Leu Gly Ile Phe Asn Ala Lys Asn Lys
545                 550                 555                 560
Pro Asp Lys Lys Ile Ile Glu Gly Asn Thr Ser Glu Asn Lys Gly Asp
                565                 570                 575
Tyr Lys Lys Met Ile Tyr Asn Leu Leu Pro Gly Pro Asn Lys Met Ile
            580                 585                 590
Pro Lys Val Phe Leu Ser Ser Lys Thr Gly Val Glu Thr Tyr Lys Pro
        595                 600                 605
Ser Ala Tyr Ile Leu Glu Gly Tyr Lys Gln Asn Lys His Ile Lys Ser
    610                 615                 620
Ser Lys Asp Phe Asp Ile Thr Phe Cys His Asp Leu Ile Asp Tyr Phe
625                 630                 635                 640
Lys Asn Cys Ile Ala Ile His Pro Glu Trp Lys Asn Phe Gly Phe Asp
                645                 650                 655
Phe Ser Asp Thr Ser Thr Tyr Glu Asp Ile Ser Gly Phe Tyr Arg Glu
            660                 665                 670
Val Glu Leu Gln Gly Tyr Lys Ile Asp Trp Thr Tyr Ile Ser Glu Lys
        675                 680                 685
Asp Ile Asp Leu Leu Gln Glu Lys Gly Gln Leu Tyr Leu Phe Gln Ile
    690                 695                 700
Tyr Asn Lys Asp Phe Ser Lys Lys Ser Thr Gly Asn Asp Asn Leu His
705                 710                 715                 720
Thr Met Tyr Leu Lys Asn Leu Phe Ser Glu Glu Asn Leu Lys Asp Ile
                725                 730                 735
Val Leu Lys Leu Asn Gly Glu Ala Glu Ile Phe Phe Arg Lys Ser Ser
            740                 745                 750
Ile Lys Asn Pro Ile Ile His Lys Lys Gly Ser Ile Leu Val Asn Arg
        755                 760                 765
Thr Tyr Glu Ala Glu Glu Lys Asp Gln Phe Gly Asn Ile Gln Ile Val
    770                 775                 780
Arg Lys Asn Ile Pro Glu Asn Ile Tyr Gln Glu Leu Tyr Lys Tyr Phe
785                 790                 795                 800
Asn Asp Lys Ser Asp Lys Glu Leu Ser Asp Glu Ala Ala Lys Leu Lys
                805                 810                 815
Asn Val Val Gly His His Glu Ala Ala Thr Asn Ile Val Lys Asp Tyr
            820                 825                 830
Arg Tyr Thr Tyr Asp Lys Tyr Phe Leu His Met Pro Ile Thr Ile Asn
        835                 840                 845
```

```
Phe Lys Ala Asn Lys Thr Gly Phe Ile Asn Asp Arg Ile Leu Gln Tyr
850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
                900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
                980                 985                 990

Tyr Leu Val Phe Lys Asp Ile Ser Ile Thr Glu Asn Gly Gly Leu Leu
                995                 1000                1005

Lys Gly Tyr Gln Leu Thr Tyr Ile Pro Asp Lys Leu Lys Asn Val
1010            1015                1020

Gly His Gln Cys Gly Cys Ile Phe Tyr Val Pro Ala Ala Tyr Thr
1025            1030                1035

Ser Lys Ile Asp Pro Thr Thr Gly Phe Val Asn Ile Phe Lys Phe
1040            1045                1050

Lys Asp Leu Thr Val Asp Ala Lys Arg Glu Phe Ile Lys Lys Phe
1055            1060                1065

Asp Ser Ile Arg Tyr Asp Ser Glu Lys Asn Leu Phe Cys Phe Thr
1070            1075                1080

Phe Asp Tyr Asn Asn Phe Ile Thr Gln Asn Thr Val Met Ser Lys
1085            1090                1095

Ser Ser Trp Ser Val Tyr Thr Tyr Gly Val Arg Ile Lys Arg Arg
1100            1105                1110

Phe Val Asn Gly Arg Phe Ser Asn Glu Ser Asp Thr Ile Asp Ile
1115            1120                1125

Thr Lys Asp Met Glu Lys Thr Leu Glu Met Thr Asp Ile Asn Trp
1130            1135                1140

Arg Asp Gly His Asp Leu Arg Gln Asp Ile Ile Asp Tyr Glu Ile
1145            1150                1155

Val Gln His Ile Phe Glu Ile Phe Arg Leu Thr Val Gln Met Arg
1160            1165                1170

Asn Ser Leu Ser Glu Leu Glu Asp Arg Asp Tyr Asp Arg Leu Ile
1175            1180                1185

Ser Pro Val Leu Asn Glu Asn Asn Ile Phe Tyr Asp Ser Ala Lys
1190            1195                1200

Ala Gly Asp Ala Leu Pro Lys Asp Ala Asp Ala Asn Gly Ala Tyr
1205            1210                1215

Cys Ile Ala Leu Lys Gly Leu Tyr Glu Ile Lys Gln Ile Thr Glu
1220            1225                1230

Asn Trp Lys Glu Asp Gly Lys Phe Ser Arg Asp Lys Leu Lys Ile
1235            1240                1245

Ser Asn Lys Asp Trp Phe Asp Phe Ile Gln Asn Lys Arg Tyr Leu
```

<210> SEQ ID NO 16
<211> LENGTH: 20
<212> TYPE: DNA
<213> ORGANISM: Artificial Sequence
<220> FEATURE:
<223> OTHER INFORMATION: PRIMER

<400> SEQUENCE: 16
ttgggtaacg ccagggtttt                                               20

<210> SEQ ID NO 17
<211> LENGTH: 20
<212> TYPE: DNA
<213> ORGANISM: Artificial Sequence
<220> FEATURE:
<223> OTHER INFORMATION: PRIMER

<400> SEQUENCE: 17
tgtgtggaat tgtgagcgga                                               20

<210> SEQ ID NO 18
<211> LENGTH: 21
<212> TYPE: DNA
<213> ORGANISM: Artificial Sequence
<220> FEATURE:
<223> OTHER INFORMATION: GRNA SCAFFOLD SEQUENCE

<400> SEQUENCE: 18
ggaatttcta ctcttgtaga t                                             21

<210> SEQ ID NO 19
<211> LENGTH: 20
<212> TYPE: DNA
<213> ORGANISM: Artificial Sequence
<220> FEATURE:
<223> OTHER INFORMATION: TARGET SEQUENCE

<400> SEQUENCE: 19
ccagtcagta atgttactgg                                               20

<210> SEQ ID NO 20
<211> LENGTH: 20
<212> TYPE: DNA
<213> ORGANISM: Artificial Sequence
<220> FEATURE:
<223> OTHER INFORMATION: TARGET SEQUENCE

<400> SEQUENCE: 20
agcaggacac tcctgcccca                                               20

<210> SEQ ID NO 21
<211> LENGTH: 97
<212> TYPE: DNA
<213> ORGANISM: Artificial Sequence
<220> FEATURE:
<223> OTHER INFORMATION: GRNA CONSTRUCT

<400> SEQUENCE: 21
cgaattaata cgactcacta tagggggaat ttctactctt gtagcaggac actcctgccc   60
cataactagc ataacccctc tctaacggag gggtttg                            97

<210> SEQ ID NO 22
<211> LENGTH: 34

```
<212> TYPE: PRT
<213> ORGANISM: Artificial Sequence
<220> FEATURE:
<223> OTHER INFORMATION: GRNA CONSTRUCT

<400> SEQUENCE: 22

Arg Ile Leu Val Val Ser Leu Leu Pro Phe Lys Leu Glu Gln Leu Tyr
1               5                   10                  15

Cys Ser Val Gly Ala Gly Tyr Ser Ala Tyr Gly Arg Glu Leu Arg Leu
            20                  25                  30

Pro Lys

<210> SEQ ID NO 23
<211> LENGTH: 106
<212> TYPE: DNA
<213> ORGANISM: Artificial Sequence
<220> FEATURE:
<223> OTHER INFORMATION: GRNA CONSTRUCT

<400> SEQUENCE: 23
gaattaatac gactcactat agggggaatt tctactcttg tagatccagt ccagtcagta      60
atgttactgg taactagcat aacccctctc taaacggagg ggttga                   106

<210> SEQ ID NO 24
<211> LENGTH: 35
<212> TYPE: PRT
<213> ORGANISM: Artificial Sequence
<220> FEATURE:
<223> OTHER INFORMATION: GRNA CONSTRUCTS

<400> SEQUENCE: 24

Arg Ile Leu Val Val Ser Leu Leu Pro Phe Lys Leu Glu Gln Leu Asp
1               5                   10                  15

Leu Ser Tyr His Leu Gln Tyr Ser Ala Tyr Gly Arg Glu Leu Arg Leu
            20                  25                  30

Pro Lys Phe
        35

<210> SEQ ID NO 25
<211> LENGTH: 26
<212> TYPE: DNA
<213> ORGANISM: Artificial Sequence
<220> FEATURE:
<223> OTHER INFORMATION: PRIMER
<220> FEATURE:
<221> NAME/KEY: N
<222> LOCATION: (5)..(5)
<223> OTHER INFORMATION: N = ANY NUCLEOTIDE
<220> FEATURE:
<221> NAME/KEY: misc_feature
<222> LOCATION: (5)..(7)
<223> OTHER INFORMATION: n is a, c, g, or t
<220> FEATURE:
<221> NAME/KEY: N
<222> LOCATION: (6)..(6)
<223> OTHER INFORMATION: N = ANY NUCLEOTIDE
<220> FEATURE:
<221> NAME/KEY: N
<222> LOCATION: (7)..(7)
<223> OTHER INFORMATION: N = G OR T

<400> SEQUENCE: 25
ttctnnnaac gctatcatac tgatgc                                          26

<210> SEQ ID NO 26
<211> LENGTH: 26
```

```
<212> TYPE: DNA
<213> ORGANISM: Artificial Sequence
<220> FEATURE:
<223> OTHER INFORMATION: PRIMER
<220> FEATURE:
<221> NAME/KEY: N
<222> LOCATION: (6)..(6)
<223> OTHER INFORMATION: N = A OR C
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: N
<222> LOCATION: (7)..(7)
<223> OTHER INFORMATION: N = ANY NUCLEOTIDE
<220> FEATURE:
<221> NAME/KEY: N
<222> LOCATION: (8)..(8)
<223> OTHER INFORMATION: N = ANY NUCLEOTIDE

<400> SEQUENCE: 26
tactcnnngg actttgacca accgtc                                          26

<210> SEQ ID NO 27
<211> LENGTH: 20
<212> TYPE: DNA
<213> ORGANISM: Artificial Sequence
<220> FEATURE:
<223> OTHER INFORMATION: TARGET SEQUENCE

<400> SEQUENCE: 27
ccagtcagta atgttactgg                                                 20

<210> SEQ ID NO 28
<211> LENGTH: 20
<212> TYPE: DNA
<213> ORGANISM: Artificial Sequence
<220> FEATURE:
<223> OTHER INFORMATION: TARGET SEQUENCE

<400> SEQUENCE: 28
agcaggacac tcctgcccca                                                 20

<210> SEQ ID NO 29
<211> LENGTH: 50
<212> TYPE: DNA
<213> ORGANISM: Artificial Sequence
<220> FEATURE:
<223> OTHER INFORMATION: PRIMER

<400> SEQUENCE: 29
gatgatttct ctagaggtac ttagagatag cgcttattct ggataaagtc                50

<210> SEQ ID NO 30
<211> LENGTH: 52
<212> TYPE: DNA
<213> ORGANISM: Artificial Sequence
<220> FEATURE:
<223> OTHER INFORMATION: PRIMER

<400> SEQUENCE: 30
cgattccgga aaggagatat ctcatgaaca acggcacaaa taattttcag aa             52

<210> SEQ ID NO 31
<211> LENGTH: 295
<212> TYPE: DNA
<213> ORGANISM: Artificial Sequence
<220> FEATURE:
```

<223> OTHER INFORMATION: EDITING CASSETTE SEQUENCE

<400> SEQUENCE: 31

```
gtgtgtgata cgaaacgaag cattggaggc attggaattt ctactcttgt agatacccctg    60
ccataaagaa actgtccatg ttgccactcg ctttaatgat gatttcagcc gcgctgtact    120
ggaggctgaa gttcagatgt gcggcgagtt gcgtgactac ctacgggtaa cataatgatt   180
atggtaatga gagacccagg tcgccagcgg caccgcgcct ttcggcggtg aaattatcga   240
tgagcgtggt ggttatgccg atcgcgtcac actaatccca gaaagacccc gtccg        295
```

<210> SEQ ID NO 32
<211> LENGTH: 295
<212> TYPE: DNA
<213> ORGANISM: Artificial Sequence
<220> FEATURE:
<223> OTHER INFORMATION: EDITING CASSETTE SEQUENCE

<400> SEQUENCE: 32

```
gtgtgtgata cgaaacgaag cattggaggc attggaattt ctactcttgt agatcatgtt    60
gccactcgct ttaatcaccc tgccataaag aaactgttac ccgtaggtag tcacgcaact   120
cgccgcacat ctgaacttca gcctccagta cagcgcggct gaaatcatca tttcattaag   180
tggctcatta gagatagctg atttgtgtag tcggtttatg cagcaacgag acgtcacgga   240
aaatgccgct catccgccac atatcctgat cttcatccca gaaagacccc gtccg        295
```

<210> SEQ ID NO 33
<211> LENGTH: 295
<212> TYPE: DNA
<213> ORGANISM: Artificial Sequence
<220> FEATURE:
<223> OTHER INFORMATION: EDITING CASSETTE SEQUENCE

<400> SEQUENCE: 33

```
gtgtgtgata cgaaacgaag cattggaggc attggaattt ctactcttgt agattgtagt    60
cggtttatgc agcaaccgcc tcgcggtgat ggtgctgcgc tggagtgacg gcagttatct   120
ggaagatcag gatatgtggc ggatgagcgg cattttccgt gacgtctcgt tgtaatgaaa   180
accgtaatga cagattagcg atttccatgt tgccactcgc tttaatgatg atttcagccg   240
cgctgtactg gaggctgaag ttcagatgtg cggcatccca gaaagacccc gtccg        295
```

<210> SEQ ID NO 34
<211> LENGTH: 295
<212> TYPE: DNA
<213> ORGANISM: Artificial Sequence
<220> FEATURE:
<223> OTHER INFORMATION: EDITING CASSETTE SEQUENCE

<400> SEQUENCE: 34

```
gtgtgtgata cgaaacgaag cattggaggc attggaattt ctactcttgt agatccgtct    60
gaatttgacc tgagctcatc cgccacatat cctgatcttc agataactg ccgtcactcc    120
agcgcagcac catcaccgcg aggcggtttt ctccggcgcg taaaaatgcg cttcattaaa   180
attctcatta cagaccactg tcctggccgt aaccgaccca gcgccgttg caccacagat   240
gaaacgccga gttaacgcca tcaaaaataa ttcgatccca gaaagacccc gtccg        295
```

<210> SEQ ID NO 35
<211> LENGTH: 295
<212> TYPE: DNA
<213> ORGANISM: Artificial Sequence

<220> FEATURE:
<223> OTHER INFORMATION: EDITING CASSETTE SEQUENCE

<400> SEQUENCE: 35

```
gtgtgtgata cgaaacgaag cattggaggc attggaattt ctactcttgt agattggcgg      60
atgagcggca tttttccagt acagcgcggc tgaaatcatc attaaagcga gtggcaacat     120
ggaaatcgct gatttgtgta gtcggtttat gcagcaacga gacgtcacgg aatcattagc     180
tcattcatta cacattctga tcttccagat aactgccgtc actccagcgc agcaccatca     240
ccgcgaggcg gttttctccg gcgcgtaaaa atgcatccca gaaaagaccc gtccg          295
```

<210> SEQ ID NO 36
<211> LENGTH: 295
<212> TYPE: DNA
<213> ORGANISM: Artificial Sequence
<220> FEATURE:
<223> OTHER INFORMATION: EDITING CASSETTE SEQUENCE

<400> SEQUENCE: 36

```
gtgtgtgata cgaaacgaag cattggaggc attggaattt ctactcttgt agataccatg      60
attacggatt cactctatta cgccagctgg cgaaagggggg atgtgctgca aggcgattaa    120
gttgggtaac gccagggttt tcccagtcac gacgttgtaa aacgacggcc agtcattacg     180
taattcatta cactcatgtt tcctgtgtga aattgttatc cgctcacaat tccacacaac     240
atacgagccg gaagcataaa gtgtaaagcc tgggatccca gaaaagaccc gtccg          295
```

<210> SEQ ID NO 37
<211> LENGTH: 295
<212> TYPE: DNA
<213> ORGANISM: Artificial Sequence
<220> FEATURE:
<223> OTHER INFORMATION: EDITING CASSETTE SEQUENCE

<400> SEQUENCE: 37

```
gtgtgtgata cgaaacgaag cattggaggc attggaattt ctactcttgt agatccatca      60
aaaataattc gcgtattacg gtcaatccgc cgtttgttcc cacgagaat ccgacgggtt      120
gttactcgct cacatttaat gttgatgaaa gctggctaca ggaaggccag acgtaatgaa     180
tttttaatg agtcaattcg gcgtttcatc tgtggtgcaa cgggcgctgg gtcggttacg      240
gccaggacag tcgtttgccg tctgaatttg acctatccca gaaaagaccc gtccg          295
```

<210> SEQ ID NO 38
<211> LENGTH: 295
<212> TYPE: DNA
<213> ORGANISM: Artificial Sequence
<220> FEATURE:
<223> OTHER INFORMATION: EDITING CASSETTE SEQUENCE

<400> SEQUENCE: 38

```
gtgtgtgata cgaaacgaag cattggaggc attggaattt ctactcttgt agatgggata      60
ctgacgaaac gcctaatggc tttcgctacc tggagagacg cgcccgctga tcctttgcga    120
atacgcccac gcgatgggta acagtcttgg cggtttcgct aaatactggc agtaatgacg     180
tcagtaatga cgacttcagg gcggcttcgt ctgggactgg gtggatcagt cgctgattaa     240
atatgatgaa aacggcaacc cgtggtcggc ttacatccca gaaaagaccc gtccg          295
```

<210> SEQ ID NO 39
<211> LENGTH: 30
<212> TYPE: DNA

```
<213> ORGANISM: Artificial Sequence
<220> FEATURE:
<223> OTHER INFORMATION: NUCLEAR LOCALIZATION SEQUENCE FRAGMENT

<400> SEQUENCE: 39
atggcaccca agaagaagag gaaggtgtta                                      30

<210> SEQ ID NO 40
<211> LENGTH: 10
<212> TYPE: PRT
<213> ORGANISM: Artificial Sequence
<220> FEATURE:
<223> OTHER INFORMATION: NUCLEAR LOCALIZATION PEPTIDE

<400> SEQUENCE: 40

Met Ala Pro Lys Lys Lys Arg Lys Val Leu
1               5                   10

<210> SEQ ID NO 41
<211> LENGTH: 199
<212> TYPE: DNA
<213> ORGANISM: Artificial Sequence
<220> FEATURE:
<223> OTHER INFORMATION: EDITING CASSETTE SEQUENCE

<400> SEQUENCE: 41
ggccccaaat tctaatttct actgttgtag atacgacgtt gaagcttcac aattttacg      60 ccgacataga ggagaagcat atgtacaatg agccggtcac aaccctcgag acacgacgtt    120
gaagcttaac aaacacacca cagacgtggg tcaataccat tgaaagatga gaaaagtaac    180
aatatacgcg ctcctgccc                                                 199

<210> SEQ ID NO 42
<211> LENGTH: 195
<212> TYPE: DNA
<213> ORGANISM: Artificial Sequence
<220> FEATURE:
<223> OTHER INFORMATION: EDITING CASSETTE SEQUENCE

<400> SEQUENCE: 42
ggccccaaat tctaatttct actgttgtag atcttttctc atctttcaat ggttttgta      60 tcctcgccat ttactctcgt cgggaaagag cgcaatggat acaattcccc acttttctca    120
tcttacaatg gtattgaccc acgtctgtgg tgtgtttgtg aagcttcaac gtcgtcaata    180
tacgcgctcc tgccc                                                     195

<210> SEQ ID NO 43
<211> LENGTH: 201
<212> TYPE: DNA
<213> ORGANISM: Artificial Sequence
<220> FEATURE:
<223> OTHER INFORMATION: EDITING CASSETTE SEQUENCE

<400> SEQUENCE: 43
ggccccaaat tctaatttct actgttgtag atccgacgag agtaaatggc gattttttca     60
ataccattga agatgagaaa agtaaagaa ttgtatccat tgcgctcgtt cccgacgaga     120
gtataaggcg aggatacgtt ctctatggag gatggcatag gtgatgaaga tgaaggagaa    180
gcaatatacg cgctcctgcc c                                              201

<210> SEQ ID NO 44
<211> LENGTH: 201
<212> TYPE: DNA
```

<213> ORGANISM: Artificial Sequence
<220> FEATURE:
<223> OTHER INFORMATION: EDITING CASSETTE SEQUENCE

<400> SEQUENCE: 44

```
ggccccaaat tctaatttct actgttgtag attccacacc tctgaccaac gctttttatt      60
ggtatgattg cccttggtgg tactattggt acaggtcttt tcattggatt atccacacct     120
ctgtaaaacg ccggcccagt gggcgctctt atatcatatt tatttatggg ttctttggca     180
tcaatatacg cgctcctgcc c                                                201
```

<210> SEQ ID NO 45
<211> LENGTH: 201
<212> TYPE: DNA
<213> ORGANISM: Artificial Sequence
<220> FEATURE:
<223> OTHER INFORMATION: EDITING CASSETTE SEQUENCE

<400> SEQUENCE: 45

```
ggccccaaat tctaatttct actgttgtag atacagtttt ctcacaaaga ttttttttct      60
gtcacgcagt ccttgggtga aatggctaca ttcatccctg ttacatcctc gttcacagtt     120
ttctcataaa gattcctttc tccagcattt ggtgcggcca atggttacat gtattggttt     180
tcaatatacg cgctcctgcc c                                                201
```

<210> SEQ ID NO 46
<211> LENGTH: 197
<212> TYPE: DNA
<213> ORGANISM: Artificial Sequence
<220> FEATURE:
<223> OTHER INFORMATION: EDITING CASSETTE SEQUENCE

<400> SEQUENCE: 46

```
ggccccaaat tctaatttct actgttgtag atggtaatta tcacaataat gattttcat       60
tcaattttgg acgtacaaag ttccactggc ggcatggatt agtatttgga aggtaattat     120
cacataaatg aacttgttcc ctgtcaaata ttacggtgaa ttcgagttct gggtcgccaa     180
tatacgcgct cctgccc                                                     197
```

<210> SEQ ID NO 47
<211> LENGTH: 201
<212> TYPE: DNA
<213> ORGANISM: Artificial Sequence
<220> FEATURE:
<223> OTHER INFORMATION: EDITING CASSETTE SEQUENCE

<400> SEQUENCE: 47

```
ggccccaaat tctaatttct actgttgtag attggaggat ggcataggtg atttttttaat     60
tgtatccatt gcgctctttc ccgacgagag taaatggcga ggatacgttc tccatggagg     120
atggcatata agatgaagat gaaggagaag tacagaacgc tgaagtgaag agagagctta     180
acaatatacg cgctcctgcc c                                                201
```

<210> SEQ ID NO 48
<211> LENGTH: 198
<212> TYPE: DNA
<213> ORGANISM: Artificial Sequence
<220> FEATURE:
<223> OTHER INFORMATION: EDITING CASSETTE SEQUENCE

<400> SEQUENCE: 48

```
ggccccaaat tctaatttct actgttgtag atttcacttc agcgttctgt acttttccca      60
```

```
atagtaccac caagggcaat cataccaata tgtctttgct taagctcccc cttcacttca    120
gcgttttata cttctccttc atcttcatca cctatgccat cctccataga gaacgtatca    180
atatacgcgc tcctgccc                                                  198
```

<210> SEQ ID NO 49
<211> LENGTH: 201
<212> TYPE: DNA
<213> ORGANISM: Artificial Sequence
<220> FEATURE:
<223> OTHER INFORMATION: EDITING CASSETTE SEQUENCE
<400> SEQUENCE: 49

```
ggccccaaat tctaatttct actgttgtag atacgcagtc cttgggtgaa attttttcca    60
gtgggcgctc ttatatcata tttatttatg ggttctttgg catattcggt cacgcagtcc    120
ttgggttaaa tggctacatt catccctgtt acatcctctt tcacagtttt ctcacaaaga    180
tcaatatacg cgctcctgcc c                                              201
```

<210> SEQ ID NO 50
<211> LENGTH: 198
<212> TYPE: DNA
<213> ORGANISM: Artificial Sequence
<220> FEATURE:
<223> OTHER INFORMATION: EDITING CASSETTE SEQUENCE
<400> SEQUENCE: 50

```
ggccccaaat tctaatttct actgttgtag atagaaaact gtgaaagagg atttttttaac   60 caatacatgt aaccattggc cgcaccaaat gctggagaaa ggaatctccc tgagaaaact    120
gtgaattagg atgtaacagg gatgaatgta gccatttcac ccaaggactg cgtgacagca    180
atatacgcgc tcctgccc                                                  198
```

<210> SEQ ID NO 51
<211> LENGTH: 201
<212> TYPE: DNA
<213> ORGANISM: Artificial Sequence
<220> FEATURE:
<223> OTHER INFORMATION: EDITING CASSETTE SEQUENCE
<400> SEQUENCE: 51

```
ggccccaaat tctaatttct actgttgtag attacaatga gccggtcaca acttttttggc  60 atagcaatga caaattcaaa agaagacgcc gacatagagg agaagcacgg gtacaatgag    120
ccgtaaacaa ccctctcttca cgacgttgaa gcttcacaaa cacaccacag acgtgggtca   180
acaatatacg cgctcctgcc c                                              201
```

<210> SEQ ID NO 52
<211> LENGTH: 201
<212> TYPE: DNA
<213> ORGANISM: Artificial Sequence
<220> FEATURE:
<223> OTHER INFORMATION: EDITING CASSETTE SEQUENCE
<400> SEQUENCE: 52

```
ggccccaaat tctaatttct actgttgtag atcacacctc tgaccaacgc cgttttgta    60 tgattgccct tggtggtact attggtacag gtcttttcat tggtttaagt acacctctga    120
cctaagccgg cccagtgggc gctcttatat catatttatt tatgggttct ttggcatatt    180
ccaatatacg cgctcctgcc c                                              201
```

```
<210> SEQ ID NO 53
<211> LENGTH: 21
<212> TYPE: DNA
<213> ORGANISM: Artificial Sequence
<220> FEATURE:
<223> OTHER INFORMATION: SPACER SEQUENCE

<400> SEQUENCE: 53
cctcccctag caacgcccct t                                              21

<210> SEQ ID NO 54
<211> LENGTH: 21
<212> TYPE: DNA
<213> ORGANISM: Artificial Sequence
<220> FEATURE:
<223> OTHER INFORMATION: SPACER SEQUENCE

<400> SEQUENCE: 54
ggatttttac cgtcaccaaa a                                              21

<210> SEQ ID NO 55
<211> LENGTH: 21
<212> TYPE: DNA
<213> ORGANISM: Artificial Sequence
<220> FEATURE:
<223> OTHER INFORMATION: SPACER SEQUENCE

<400> SEQUENCE: 55
tggctctatt ctctctccca t                                              21

<210> SEQ ID NO 56
<211> LENGTH: 21
<212> TYPE: DNA
<213> ORGANISM: Artificial Sequence
<220> FEATURE:
<223> OTHER INFORMATION: SPACER SEQUENCE

<400> SEQUENCE: 56
gctgaactct gcaggtcagt t                                              21

<210> SEQ ID NO 57
<211> LENGTH: 21
<212> TYPE: DNA
<213> ORGANISM: Artificial Sequence
<220> FEATURE:
<223> OTHER INFORMATION: SPACER SEQUENCE

<400> SEQUENCE: 57
tcaggttagc ttcttgtacc t                                              21

<210> SEQ ID NO 58
<211> LENGTH: 21
<212> TYPE: DNA
<213> ORGANISM: Artificial Sequence
<220> FEATURE:
<223> OTHER INFORMATION: SPACER SEQUENCE

<400> SEQUENCE: 58
agattcagaa ccacttctct a                                              21

<210> SEQ ID NO 59
<211> LENGTH: 21
<212> TYPE: DNA
<213> ORGANISM: Artificial Sequence
<220> FEATURE:
<223> OTHER INFORMATION: SPACER SEQUENCE
```

<400> SEQUENCE: 59
ctgtagtcca aggagggtat a                                              21

<210> SEQ ID NO 60
<211> LENGTH: 21
<212> TYPE: DNA
<213> ORGANISM: Artificial Sequence
<220> FEATURE:
<223> OTHER INFORMATION: SPACER SEQUENCE

<400> SEQUENCE: 60
gataagcatg ttttccaaga a                                              21

<210> SEQ ID NO 61
<211> LENGTH: 21
<212> TYPE: DNA
<213> ORGANISM: Artificial Sequence
<220> FEATURE:
<223> OTHER INFORMATION: SPACER SEQUENCE

<400> SEQUENCE: 61 ccccttttaaa gaagctaagt t                                             21

<210> SEQ ID NO 62
<211> LENGTH: 21
<212> TYPE: DNA
<213> ORGANISM: Artificial Sequence
<220> FEATURE:
<223> OTHER INFORMATION: SPACER SEQUENCE

<400> SEQUENCE: 62
acttctctaa aaatatggct c                                              21

<210> SEQ ID NO 63
<211> LENGTH: 21
<212> TYPE: DNA
<213> ORGANISM: Artificial Sequence
<220> FEATURE:
<223> OTHER INFORMATION: SPACER SEQUENCE

<400> SEQUENCE: 63
tcagattcag aaccacttct c                                              21

<210> SEQ ID NO 64
<211> LENGTH: 21
<212> TYPE: DNA
<213> ORGANISM: Artificial Sequence
<220> FEATURE:
<223> OTHER INFORMATION: SPACER SEQUENCE

<400> SEQUENCE: 64
tatggctcta ttctctctcc c                                              21

<210> SEQ ID NO 65
<211> LENGTH: 21
<212> TYPE: DNA
<213> ORGANISM: Artificial Sequence
<220> FEATURE:
<223> OTHER INFORMATION: SPACER SEQUENCE

<400> SEQUENCE: 65
tctctcccat cctcaggtta g                                              21

<210> SEQ ID NO 66

-continued

```
<211> LENGTH: 21
<212> TYPE: DNA
<213> ORGANISM: Artificial Sequence
<220> FEATURE:
<223> OTHER INFORMATION: SPACER SEQUENCE

<400> SEQUENCE: 66
tcaggtgtat tttgacctac g                                           21

<210> SEQ ID NO 67
<211> LENGTH: 1263
<212> TYPE: PRT
<213> ORGANISM: Artificial Sequence
<220> FEATURE:
<223> OTHER INFORMATION: MAD70 VARIANT K535R/N539S

<400> SEQUENCE: 67
```

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Lys Leu His Lys Gln Ile Leu Cys
        275                 280                 285

Ile Ala Asp Thr Ser Tyr Glu Val Pro Tyr Lys Phe Glu Ser Asp Glu
    290                 295                 300

Glu Val Tyr Gln Ser Val Asn Gly Phe Leu Asp Asn Ile Ser Ser Lys
305                 310                 315                 320

-continued

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
    370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
    450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
        515                 520                 525

Asp Gly Trp Ser Lys Ser Arg Glu Tyr Ser Ser Asn Ala Ile Ile Leu
    530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
        595                 600                 605

Ser Ala Tyr Ile Leu Glu Gly Tyr Lys Gln Asn Lys His Ile Lys Ser
    610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

```
Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
            755                 760                 765

Thr Tyr Glu Ala Glu Glu Lys Asp Gln Phe Gly Asn Ile Gln Ile Val
            770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
            805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
            835                 840                 845

Phe Lys Ala Asn Lys Thr Gly Phe Ile Asn Asp Arg Ile Leu Gln Tyr
            850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
            885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
            965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
            995                 1000                1005

Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
```

```
                  1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 68
<211> LENGTH: 1060
<212> TYPE: PRT
<213> ORGANISM: Artificial Sequence
<220> FEATURE:
<223> OTHER INFORMATION: MAD70 VARIANT K535R, N539S, K594L, E730Q

<400> SEQUENCE: 68

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
```

```
            245                 250                 255
Gly Lys Val Asn Ser Phe Met Asn Leu Tyr Cys Gln Lys Asn Lys Glu
            260                 265                 270
Asn Lys Asn Leu Tyr Lys Leu Gln Lys Leu His Lys Gln Ile Leu Cys
            275                 280                 285
Ile Ala Asp Thr Ser Tyr Glu Val Pro Tyr Lys Phe Glu Ser Asp Glu
            290                 295                 300
Glu Val Tyr Gln Ser Val Asn Gly Phe Leu Asp Asn Ile Ser Ser Lys
305                 310                 315                 320
His Ile Val Glu Arg Leu Arg Lys Ile Gly Asp Asn Tyr Asn Gly Tyr
            325                 330                 335
Asn Leu Asp Lys Ile Tyr Ile Val Ser Lys Phe Tyr Glu Ser Val Ser
            340                 345                 350
Gln Lys Thr Tyr Arg Asp Trp Glu Thr Ile Asn Thr Ala Leu Glu Ile
            355                 360                 365
His Tyr Asn Asn Ile Leu Pro Gly Asn Gly Lys Ser Lys Ala Asp Lys
            370                 375                 380
Val Lys Lys Ala Val Lys Asn Asp Leu Gln Lys Ser Ile Thr Glu Ile
385                 390                 395                 400
Asn Glu Leu Val Ser Asn Tyr Lys Leu Cys Ser Asp Asp Asn Ile Lys
            405                 410                 415
Ala Glu Thr Tyr Ile His Glu Ile Ser His Ile Leu Asn Asn Phe Glu
            420                 425                 430
Ala Gln Glu Leu Lys Tyr Asn Pro Glu Ile His Leu Val Glu Ser Glu
            435                 440                 445
Leu Lys Ala Ser Glu Leu Lys Asn Val Leu Asp Val Ile Met Asn Ala
450                 455                 460
Phe His Trp Cys Ser Val Phe Met Thr Glu Glu Leu Val Asp Lys Asp
465                 470                 475                 480
Asn Asn Phe Tyr Ala Glu Leu Glu Glu Ile Tyr Asp Glu Ile Tyr Pro
            485                 490                 495
Val Ile Ser Leu Tyr Asn Leu Val Arg Asn Tyr Val Thr Gln Lys Pro
            500                 505                 510
Tyr Ser Thr Lys Lys Ile Lys Leu Asn Phe Gly Ile Pro Thr Leu Ala
            515                 520                 525
Asp Gly Trp Ser Lys Ser Arg Glu Tyr Ser Ser Asn Ala Ile Ile Leu
            530                 535                 540
Met Arg Asp Asn Leu Tyr Tyr Leu Gly Ile Phe Asn Ala Lys Asn Lys
545                 550                 555                 560
Pro Asp Lys Lys Ile Ile Glu Gly Asn Thr Ser Glu Asn Lys Gly Asp
            565                 570                 575
Tyr Lys Lys Met Ile Tyr Asn Leu Leu Pro Gly Pro Asn Lys Met Ile
            580                 585                 590
Pro Leu Val Phe Leu Ser Ser Lys Thr Gly Val Glu Thr Tyr Lys Pro
            595                 600                 605
Ser Ala Tyr Ile Leu Glu Gly Tyr Lys Gln Asn Lys His Ile Lys Ser
            610                 615                 620
Ser Lys Asp Phe Asp Ile Thr Phe Cys His Asp Leu Ile Asp Tyr Phe
625                 630                 635                 640
Lys Asn Cys Ile Ala Ile His Pro Glu Trp Lys Asn Phe Gly Phe Asp
            645                 650                 655
Phe Ser Asp Thr Ser Thr Tyr Glu Asp Ile Ser Gly Phe Tyr Arg Glu
            660                 665                 670
```

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Ser Thr Gly Asn Asp Asn Leu His
705                 710                 715                 720

Thr Met Tyr Leu Lys Asn Leu Phe Ser Gln Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
                755                 760                 765

Thr Tyr Glu Ala Glu Lys Asp Gln Phe Gly Asn Ile Gln Ile Val
            770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
                835                 840                 845

Phe Lys Ala Asn Lys Thr Gly Phe Ile Asn Asp Arg Ile Leu Gln Tyr
    850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
                900                 905                 910

Leu Lys Gln Gln Glu Gly Ala Arg Gln Ile Ala Arg Lys Glu Trp Lys
    915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
    995                 1000                1005

Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Lys Asp Leu Thr Val Asp Ala
    1055                1060

<210> SEQ ID NO 69
<211> LENGTH: 1263

```
<212> TYPE: PRT
<213> ORGANISM: Artificial Sequence
<220> FEATURE:
<223> OTHER INFORMATION: MAD70 VARIANT K95L

<400> SEQUENCE: 69
```

| | | | | | | | | | | | | | | |
|---|---|---|---|---|---|---|---|---|---|---|---|---|---|---|
| Met | Asn | Asn | Gly | Thr | Asn | Asn | Phe | Gln | Asn | Phe | Ile | Gly | Ile | Ser | Ser |
| 1 | | | | 5 | | | | | 10 | | | | | 15 |
| Leu | Gln | Lys | Thr | Leu | Arg | Asn | Ala | Leu | Ile | Pro | Thr | Glu | Thr | Thr | Gln |
| | | | 20 | | | | | 25 | | | | | 30 | | |
| Gln | Phe | Ile | Val | Lys | Asn | Gly | Ile | Ile | Lys | Glu | Asp | Gl

```
Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
            405                 410                 415

Ala Glu Thr Tyr Ile His Glu Ile Ser His Ile Leu Asn Asn Phe Glu
        420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
    450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
            485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
        515                 520                 525

Asp Gly Trp Ser Lys Ser Lys Glu Tyr Ser Asn Asn Ala Ile Ile Leu
    530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
            565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
            595                 600                 605

Ser Ala Tyr Ile Leu Glu Gly Tyr Lys Gln Asn Lys His Ile Lys Ser
    610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
            645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Glu Lys Gly Gln Leu Tyr Leu Phe Gln Ile
        690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
            725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
        755                 760                 765

Thr Tyr Glu Ala Glu Glu Lys Asp Gln Phe Gly Asn Ile Gln Ile Val
        770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
```

```
            805                 810                 815
Asn Val Val Gly His His Glu Ala Ala Thr Asn Ile Val Lys Asp Tyr
            820                 825                 830
Arg Tyr Thr Tyr Asp Lys Tyr Phe Leu His Met Pro Ile Thr Ile Asn
            835                 840                 845
Phe Lys Ala Asn Lys Thr Gly Phe Ile Asn Asp Arg Ile Leu Gln Tyr
            850                 855                 860
Ile Ala Lys Glu Lys Asp Leu His Val Ile Gly Ile Asp Arg Gly Glu
865                 870                 875                 880
Arg Asn Leu Ile Tyr Val Ser Val Ile Asp Thr Cys Gly Asn Ile Val
            885                 890                 895
Glu Gln Lys Ser Phe Asn Ile Val Asn Gly Tyr Asp Tyr Gln Ile Lys
            900                 905                 910
Leu Lys Gln Gln Glu Gly Ala Arg Gln Ile Ala Arg Lys Glu Trp Lys
            915                 920                 925
Glu Ile Gly Lys Ile Lys Glu Ile Lys Glu Gly Tyr Leu Ser Leu Val
            930                 935                 940
Ile His Glu Ile Ser Lys Met Val Ile Lys Tyr Asn Ala Ile Ile Ala
945                 950                 955                 960
Met Glu Asp Leu Ser Tyr Gly Phe Lys Lys Gly Arg Phe Lys Val Glu
                965                 970                 975
Arg Gln Val Tyr Gln Lys Phe Glu Thr Met Leu Ile Asn Lys Leu Asn
            980                 985                 990
Tyr Leu Val Phe Lys Asp Ile Ser Ile Thr Glu Asn Gly Gly Leu Leu
            995                 1000                1005
Lys Gly Tyr Gln Leu Thr Tyr Ile Pro Asp Lys Leu Lys Asn Val
            1010                1015                1020
Gly His Gln Cys Gly Cys Ile Phe Tyr Val Pro Ala Ala Tyr Thr
            1025                1030                1035
Ser Lys Ile Asp Pro Thr Thr Gly Phe Val Asn Ile Phe Lys Phe
            1040                1045                1050
Lys Asp Leu Thr Val Asp Ala Lys Arg Glu Phe Ile Lys Lys Phe
            1055                1060                1065
Asp Ser Ile Arg Tyr Asp Ser Glu Lys Asn Leu Phe Cys Phe Thr
            1070                1075                1080
Phe Asp Tyr Asn Asn Phe Ile Thr Gln Asn Thr Val Met Ser Lys
            1085                1090                1095
Ser Ser Trp Ser Val Tyr Thr Tyr Gly Val Arg Ile Lys Arg Arg
            1100                1105                1110
Phe Val Asn Gly Arg Phe Ser Asn Glu Ser Asp Thr Ile Asp Ile
            1115                1120                1125
Thr Lys Asp Met Glu Lys Thr Leu Glu Met Thr Asp Ile Asn Trp
            1130                1135                1140
Arg Asp Gly His Asp Leu Arg Gln Asp Ile Ile Asp Tyr Glu Ile
            1145                1150                1155
Val Gln His Ile Phe Glu Ile Phe Arg Leu Thr Val Gln Met Arg
            1160                1165                1170
Asn Ser Leu Ser Glu Leu Glu Asp Arg Asp Tyr Asp Arg Leu Ile
            1175                1180                1185
Ser Pro Val Leu Asn Glu Asn Asn Ile Phe Tyr Asp Ser Ala Lys
            1190                1195                1200
Ala Gly Asp Ala Leu Pro Lys Asp Ala Asp Ala Asn Gly Ala Tyr
            1205                1210                1215
```

```
Cys Ile Ala Leu Lys Gly Leu Tyr Glu Ile Lys Gln Ile Thr Glu
    1220            1225                1230

Asn Trp Lys Glu Asp Gly Lys Phe Ser Arg Asp Lys Leu Lys Ile
    1235            1240                1245

Ser Asn Lys Asp Trp Phe Phe Ile Gln Asn Lys Arg Tyr Leu
    1250            1255                1260

<210> SEQ ID NO 70
<211> LENGTH: 1263
<212> TYPE: PRT
<213> ORGANISM: Artificial Sequence
<220> FEATURE:
<223> OTHER INFORMATION: MAD70 VARIANT V207I, K278T

<400> SEQUENCE: 70

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
                20                  25                  30

Gln Phe Ile Val Lys Asn Gly Ile Ile Lys Glu Asp Glu Leu Arg Gly
            35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Ile Lys
        195                 200                 205

Ser Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Thr Leu Gln Lys Leu His Lys Gln Ile Leu Cys
        275                 280                 285

Ile Ala Asp Thr Ser Tyr Glu Val Pro Tyr Lys Phe Glu Ser Asp Glu
    290                 295                 300

Glu Val Tyr Gln Ser Val Asn Gly Phe Leu Asp Asn Ile Ser Ser Lys
305                 310                 315                 320
```

```
His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
    370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
    450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
        515                 520                 525

Asp Gly Trp Ser Lys Ser Lys Glu Tyr Ser Asn Asn Ala Ile Ile Leu
    530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
        595                 600                 605

Ser Ala Tyr Ile Leu Glu Gly Tyr Lys Gln Asn Lys His Ile Lys Ser
    610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735
```

```
Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
            755                 760                 765

Thr Tyr Glu Ala Glu Glu Lys Asp Gln Phe Gly Asn Ile Gln Ile Val
            770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
            835                 840                 845

Phe Lys Ala Asn Lys Thr Gly Phe Ile Asn Asp Arg Ile Leu Gln Tyr
            850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
            995                 1000                1005

Lys Gly Tyr Gln Leu Thr Tyr Ile Pro Asp Lys Leu Lys Asn Val
            1010                1015                1020

Gly His Gln Cys Gly Cys Ile Phe Tyr Val Pro Ala Ala Tyr Thr
            1025                1030                1035

Ser Lys Ile Asp Pro Thr Thr Gly Phe Val Asn Ile Phe Lys Phe
            1040                1045                1050

Lys Asp Leu Thr Val Asp Ala Lys Arg Glu Phe Ile Lys Lys Phe
            1055                1060                1065

Asp Ser Ile Arg Tyr Asp Ser Glu Lys Asn Leu Phe Cys Phe Thr
            1070                1075                1080

Phe Asp Tyr Asn Asn Phe Ile Thr Gln Asn Thr Val Met Ser Lys
            1085                1090                1095

Ser Ser Trp Ser Val Tyr Thr Tyr Gly Val Arg Ile Lys Arg Arg
            1100                1105                1110

Phe Val Asn Gly Arg Phe Ser Asn Glu Ser Asp Thr Ile Asp Ile
            1115                1120                1125

Thr Lys Asp Met Glu Lys Thr Leu Glu Met Thr Asp Ile Asn Trp
            1130                1135                1140

Arg Asp Gly His Asp Leu Arg Gln Asp Ile Ile Asp Tyr Glu Ile
```

-continued

```
                    1145                1150                1155

Val Gln His Ile Phe Glu Ile Phe Arg Leu Thr Val Gln Met Arg
                1160                1165                1170

Asn Ser Leu Ser Glu Leu Glu Asp Arg Asp Tyr Asp Arg Leu Ile
                1175                1180                1185

Ser Pro Val Leu Asn Glu Asn Asn Ile Phe Tyr Asp Ser Ala Lys
                1190                1195                1200

Ala Gly Asp Ala Leu Pro Lys Asp Ala Asp Ala Asn Gly Ala Tyr
                1205                1210                1215

Cys Ile Ala Leu Lys Gly Leu Tyr Glu Ile Lys Gln Ile Thr Glu
                1220                1225                1230

Asn Trp Lys Glu Asp Gly Lys Phe Ser Arg Asp Lys Leu Lys Ile
                1235                1240                1245

Ser Asn Lys Asp Trp Phe Asp Phe Ile Gln Asn Lys Arg Tyr Leu
                1250                1255                1260

<210> SEQ ID NO 71
<211> LENGTH: 1263
<212> TYPE: PRT
<213> ORGANISM: Artificial Sequence
<220> FEATURE:
<223> OTHER INFORMATION: MAD70 VARIANT K511D

<400> SEQUENCE: 71

Met Asn Asn Gly Thr Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
                20                  25                  30

Gln Phe Ile Val Lys Asn Gly Ile Ile Lys Glu Asp Glu Leu Arg Gly
            35                  40                  45

Glu Asn Arg Gln Ile Leu Lys Asp Ile Met Asp Asp Tyr Tyr Arg Gly
        50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
                100                 105                 110

Phe Ala Asn Asp Asp Arg Phe Lys Asn Met Phe Ser Ala Lys Leu Ile
            115                 120                 125

Ser Asp Ile Leu Pro Glu Phe Val Ile His Asn Asn Tyr Ser Ala
        130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
        210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
```

```
                    245                 250                 255
Gly Lys Val Asn Ser Phe Met Asn Leu Tyr Cys Gln Lys Asn Lys Glu
                260                 265                 270
Asn Lys Asn Leu Tyr Lys Leu Gln Lys Leu His Lys Gln Ile Leu Cys
            275                 280                 285
Ile Ala Asp Thr Ser Tyr Glu Val Pro Tyr Lys Phe Glu Ser Asp Glu
        290                 295                 300
Glu Val Tyr Gln Ser Val Asn Gly Phe Leu Asp Asn Ile Ser Ser Lys
305                 310                 315                 320
His Ile Val Glu Arg Leu Arg Lys Ile Gly Asp Asn Tyr Asn Gly Tyr
                325                 330                 335
Asn Leu Asp Lys Ile Tyr Ile Val Ser Lys Phe Tyr Glu Ser Val Ser
            340                 345                 350
Gln Lys Thr Tyr Arg Asp Trp Glu Thr Ile Asn Thr Ala Leu Glu Ile
        355                 360                 365
His Tyr Asn Asn Ile Leu Pro Gly Asn Gly Lys Ser Lys Ala Asp Lys
    370                 375                 380
Val Lys Lys Ala Val Lys Asn Asp Leu Gln Lys Ser Ile Thr Glu Ile
385                 390                 395                 400
Asn Glu Leu Val Ser Asn Tyr Lys Leu Cys Ser Asp Asp Asn Ile Lys
                405                 410                 415
Ala Glu Thr Tyr Ile His Glu Ile Ser His Ile Leu Asn Asn Phe Glu
            420                 425                 430
Ala Gln Glu Leu Lys Tyr Asn Pro Glu Ile His Leu Val Glu Ser Glu
        435                 440                 445
Leu Lys Ala Ser Glu Leu Lys Asn Val Leu Asp Val Ile Met Asn Ala
    450                 455                 460
Phe His Trp Cys Ser Val Phe Met Thr Glu Gly Leu Val Asp Lys Asp
465                 470                 475                 480
Asn Asn Phe Tyr Ala Glu Leu Glu Glu Ile Tyr Asp Glu Ile Tyr Pro
                485                 490                 495
Val Ile Ser Leu Tyr Asn Leu Val Arg Asn Tyr Val Thr Gln Asp Pro
            500                 505                 510
Tyr Ser Thr Lys Lys Ile Lys Leu Asn Phe Gly Ile Pro Thr Leu Ala
        515                 520                 525
Asp Gly Trp Ser Lys Ser Lys Glu Tyr Ser Asn Asn Ala Ile Ile Leu
    530                 535                 540
Met Arg Asp Asn Leu Tyr Tyr Leu Gly Ile Phe Asn Ala Lys Asn Lys
545                 550                 555                 560
Pro Asp Lys Lys Ile Ile Glu Gly Asn Thr Ser Glu Asn Lys Gly Asp
                565                 570                 575
Tyr Lys Lys Met Ile Tyr Asn Leu Leu Pro Gly Pro Asn Lys Met Ile
            580                 585                 590
Pro Lys Val Phe Leu Ser Ser Lys Thr Gly Val Glu Thr Tyr Lys Pro
        595                 600                 605
Ser Ala Tyr Ile Leu Glu Gly Tyr Lys Gln Asn Lys His Ile Lys Ser
    610                 615                 620
Ser Lys Asp Phe Asp Ile Thr Phe Cys His Asp Leu Ile Asp Tyr Phe
625                 630                 635                 640
Lys Asn Cys Ile Ala Ile His Pro Glu Trp Lys Asn Phe Gly Phe Asp
                645                 650                 655
Phe Ser Asp Thr Ser Thr Tyr Glu Asp Ile Ser Gly Phe Tyr Arg Glu
            660                 665                 670
```

```
Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
690                 695                 700

Tyr Asn Lys Asp Phe Ser Lys Ser Thr Gly Asn Asp Asn Leu His
705                 710                 715                 720

Thr Met Tyr Leu Lys Asn Leu Phe Ser Glu Glu Asn Leu Lys Asp Ile
            725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
            755                 760                 765

Thr Tyr Glu Ala Glu Lys Asp Gln Phe Gly Asn Ile Gln Ile Val
770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
            835                 840                 845

Phe Lys Ala Asn Lys Thr Gly Phe Ile Asn Asp Arg Ile Leu Gln Tyr
850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
            995                 1000                1005

Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080
```

```
Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 72
<211> LENGTH: 1263
<212> TYPE: PRT
<213> ORGANISM: Artificial Sequence
<220> FEATURE:
<223> OTHER INFORMATION: MAD70 VARIANT N589H

<400> SEQUENCE: 72

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175
```

```
Ala Asp Asp Ile Ser Ser Ser Cys His Arg Ile Val Asn Asp Asn
            180             185                 190

Ala Glu Ile Phe Phe Ser Asn Ala Leu Val Tyr Arg Arg Ile Val Lys
        195                 200             205

Ser Leu Ser Asn Asp Asp Ile Asn Lys Ile Ser Gly Asp Met Lys Asp
    210             215                 220

Ser Leu Lys Glu Met Ser Leu Glu Glu Ile Tyr Ser Tyr Glu Lys Tyr
225             230             235                 240

Gly Glu Phe Ile Thr Gln Glu Gly Ile Ser Phe Tyr Asn Asp Ile Cys
                245             250                 255

Gly Lys Val Asn Ser Phe Met Asn Leu Tyr Cys Gln Lys Asn Lys Glu
            260             265                 270

Asn Lys Asn Leu Tyr Lys Leu Gln Lys Leu His Lys Gln Ile Leu Cys
        275             280             285

Ile Ala Asp Thr Ser Tyr Glu Val Pro Tyr Lys Phe Glu Ser Asp Glu
    290             295             300

Glu Val Tyr Gln Ser Val Asn Gly Phe Leu Asp Asn Ile Ser Ser Lys
305             310             315                 320

His Ile Val Glu Arg Leu Arg Lys Ile Gly Asp Asn Tyr Asn Gly Tyr
                325             330                 335

Asn Leu Asp Lys Ile Tyr Ile Val Ser Lys Phe Tyr Glu Ser Val Ser
            340             345             350

Gln Lys Thr Tyr Arg Asp Trp Glu Thr Ile Asn Thr Ala Leu Glu Ile
        355             360             365

His Tyr Asn Asn Ile Leu Pro Gly Asn Gly Lys Ser Lys Ala Asp Lys
    370             375             380

Val Lys Lys Ala Val Lys Asn Asp Leu Gln Lys Ser Ile Thr Glu Ile
385             390             395                 400

Asn Glu Leu Val Ser Asn Tyr Lys Leu Cys Ser Asp Asp Asn Ile Lys
                405             410                 415

Ala Glu Thr Tyr Ile His Glu Ile Ser His Ile Leu Asn Asn Phe Glu
            420             425             430

Ala Gln Glu Leu Lys Tyr Asn Pro Glu Ile His Leu Val Glu Ser Glu
        435             440             445

Leu Lys Ala Ser Glu Leu Lys Asn Val Leu Asp Val Ile Met Asn Ala
    450             455             460

Phe His Trp Cys Ser Val Phe Met Thr Glu Glu Leu Val Asp Lys Asp
465             470             475                 480

Asn Asn Phe Tyr Ala Glu Leu Glu Glu Ile Tyr Asp Glu Ile Tyr Pro
                485             490                 495

Val Ile Ser Leu Tyr Asn Leu Val Arg Asn Tyr Val Thr Gln Lys Pro
            500             505             510

Tyr Ser Thr Lys Lys Ile Lys Leu Asn Phe Gly Ile Pro Thr Leu Ala
        515             520             525

Asp Gly Trp Ser Lys Ser Lys Glu Tyr Ser Asn Asn Ala Ile Ile Leu
    530             535             540

Met Arg Asp Asn Leu Tyr Tyr Leu Gly Ile Phe Asn Ala Lys Asn Lys
545             550             555                 560

Pro Asp Lys Lys Ile Ile Glu Gly Asn Thr Ser Glu Asn Lys Gly Asp
                565             570                 575

Tyr Lys Lys Met Ile Tyr Asn Leu Leu Pro Gly Pro His Lys Met Ile
            580             585             590

Pro Lys Val Phe Leu Ser Ser Lys Thr Gly Val Glu Thr Tyr Lys Pro
```

-continued

```
                595                 600                 605
Ser Ala Tyr Ile Leu Glu Gly Tyr Lys Gln Asn Lys His Ile Lys Ser
610                     615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
                660                 665                 670

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
                755                 760                 765

Thr Tyr Glu Ala Glu Glu Lys Asp Gln Phe Gly Asn Ile Gln Ile Val
770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
        835                 840                 845

Phe Lys Ala Asn Lys Thr Gly Phe Ile Asn Asp Arg Ile Leu Gln Tyr
850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
    930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser  Ile Thr Glu Asn Gly  Gly Leu Leu
        995                 1000                1005

Lys Gly Tyr Gln Leu Thr Tyr  Ile Pro Asp Lys Leu  Lys Asn Val
    1010                1015                1020
```

```
Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 73
<211> LENGTH: 1263
<212> TYPE: PRT
<213> ORGANISM: Artificial Sequence
<220> FEATURE:
<223> OTHER INFORMATION: MAD70 VARIANT L597V

<400> SEQUENCE: 73

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
                20                  25                  30

Gln Phe Ile Val Lys Asn Gly Ile Ile Lys Glu Asp Glu Leu Arg Gly
            35                  40                  45

Glu Asn Arg Gln Ile Leu Lys Asp Ile Met Asp Asp Tyr Tyr Arg Gly
        50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110
```

```
Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Asn Tyr Ser Ala
130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
                180                 185                 190

Ala Glu Ile Phe Phe Ser Asn Ala Leu Val Tyr Arg Arg Ile Val Lys
                195                 200                 205

Ser Leu Ser Asn Asp Asp Ile Asn Lys Ile Ser Gly Asp Met Lys Asp
210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
                260                 265                 270

Asn Lys Asn Leu Tyr Lys Leu Gln Lys Leu His Lys Gln Ile Leu Cys
            275                 280                 285

Ile Ala Asp Thr Ser Tyr Glu Val Pro Tyr Lys Phe Glu Ser Asp Glu
        290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
                340                 345                 350

Gln Lys Thr Tyr Arg Asp Trp Glu Thr Ile Asn Thr Ala Leu Glu Ile
            355                 360                 365

His Tyr Asn Asn Ile Leu Pro Gly Asn Gly Lys Ser Lys Ala Asp Lys
        370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
            435                 440                 445

Leu Lys Ala Ser Glu Leu Lys Asn Val Leu Asp Val Ile Met Asn Ala
        450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
        515                 520                 525
```

-continued

Asp Gly Trp Ser Lys Ser Lys Glu Tyr Ser Asn Asn Ala Ile Ile Leu
         530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                 565                 570                 575

Tyr Lys Lys Met Ile Tyr Asn Leu Leu Pro Gly Pro Asn Lys Met Ile
             580                 585                 590

Pro Lys Val Phe Val Ser Ser Lys Thr Gly Val Glu Thr Tyr Lys Pro
         595                 600                 605

Ser Ala Tyr Ile Leu Glu Gly Tyr Lys Gln Asn Lys His Ile Lys Ser
    610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                 645                 650                 655

Phe Ser Asp Thr Ser Thr Tyr Glu Asp Ile Ser Gly Phe Tyr Arg Glu
             660                 665                 670

Val Glu Leu Gln Gly Tyr Lys Ile Asp Trp Thr Tyr Ile Ser Glu Lys
         675                 680                 685

Asp Ile Asp Leu Leu Gln Glu Lys Gly Gln Leu Tyr Leu Phe Gln Ile
690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                 725                 730                 735

Val Leu Lys Leu Asn Gly Glu Ala Glu Ile Phe Phe Arg Lys Ser Ser
             740                 745                 750

Ile Lys Asn Pro Ile Ile His Lys Lys Gly Ser Ile Leu Val Asn Arg
         755                 760                 765

Thr Tyr Glu Ala Glu Glu Lys Asp Gln Phe Gly Asn Ile Gln Ile Val
    770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                 805                 810                 815

Asn Val Val Gly His His Glu Ala Ala Thr Asn Ile Val Lys Asp Tyr
             820                 825                 830

Arg Tyr Thr Tyr Asp Lys Tyr Phe Leu His Met Pro Ile Thr Ile Asn
         835                 840                 845

Phe Lys Ala Asn Lys Thr Gly Phe Ile Asn Asp Arg Ile Leu Gln Tyr
    850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                 885                 890                 895

Glu Gln Lys Ser Phe Asn Ile Val Asn Gly Tyr Asp Tyr Gln Ile Lys
             900                 905                 910

Leu Lys Gln Gln Glu Gly Ala Arg Gln Ile Ala Arg Lys Glu Trp Lys
         915                 920                 925

Glu Ile Gly Lys Ile Lys Glu Ile Lys Glu Gly Tyr Leu Ser Leu Val
    930                 935                 940

Ile His Glu Ile Ser Lys Met Val Ile Lys Tyr Asn Ala Ile Ile Ala

```
                945                 950                 955                 960
Met Glu Asp Leu Ser Tyr Gly Phe Lys Lys Gly Arg Phe Lys Val Glu
                    965                 970                 975

Arg Gln Val Tyr Gln Lys Phe Glu Thr Met Leu Ile Asn Lys Leu Asn
                    980                 985                 990

Tyr Leu Val Phe Lys Asp Ile Ser  Ile Thr Glu Asn Gly  Gly Leu Leu
                    995                1000                1005

Lys Gly Tyr Gln Leu Thr Tyr  Ile Pro Asp Lys Leu  Lys Asn Val
        1010                1015                1020

Gly His Gln Cys Gly Cys Ile  Phe Tyr Val Pro Ala  Ala Tyr Thr
        1025                1030                1035

Ser Lys Ile Asp Pro Thr Thr  Gly Phe Val Asn Ile  Phe Lys Phe
        1040                1045                1050

Lys Asp Leu Thr Val Asp Ala Lys Arg Glu Phe Ile  Lys Lys Phe
        1055                1060                1065

Asp Ser Ile Arg Tyr Asp Ser  Glu Lys Asn Leu Phe  Cys Phe Thr
        1070                1075                1080

Phe Asp Tyr Asn Asn Phe Ile  Thr Gln Asn Thr Val  Met Ser Lys
        1085                1090                1095

Ser Ser Trp Ser Val Tyr Thr  Tyr Gly Val Arg Ile  Lys Arg Arg
        1100                1105                1110

Phe Val Asn Gly Arg Phe Ser  Asn Glu Ser Asp Thr  Ile Asp Ile
        1115                1120                1125

Thr Lys Asp Met Glu Lys Thr  Leu Glu Met Thr Asp  Ile Asn Trp
        1130                1135                1140

Arg Asp Gly His Asp Leu Arg  Gln Asp Ile Ile Asp  Tyr Glu Ile
        1145                1150                1155

Val Gln His Ile Phe Glu Ile  Phe Arg Leu Thr Val  Gln Met Arg
        1160                1165                1170

Asn Ser Leu Ser Glu Leu Glu  Asp Arg Asp Tyr Asp  Arg Leu Ile
        1175                1180                1185

Ser Pro Val Leu Asn Glu Asn  Asn Ile Phe Tyr Asp  Ser Ala Lys
        1190                1195                1200

Ala Gly Asp Ala Leu Pro Lys  Asp Ala Asp Ala Asn  Gly Ala Tyr
        1205                1210                1215

Cys Ile Ala Leu Lys Gly Leu  Tyr Glu Ile Lys Gln  Ile Thr Glu
        1220                1225                1230

Asn Trp Lys Glu Asp Gly Lys  Phe Ser Arg Asp Lys  Leu Lys Ile
        1235                1240                1245

Ser Asn Lys Asp Trp Phe Asp  Phe Ile Gln Asn Lys  Arg Tyr Leu
        1250                1255                1260

<210> SEQ ID NO 74
<211> LENGTH: 1263
<212> TYPE: PRT
<213> ORGANISM: Artificial Sequence
<220> FEATURE:
<223> OTHER INFORMATION: MAD70 VARIANT K712V

<400> SEQUENCE: 74

Met Asn Asn Gly Thr Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
                20                  25                  30

Gln Phe Ile Val Lys Asn Gly Ile Ile Lys Glu Asp Glu Leu Arg Gly
```

35                  40                  45
Glu Asn Arg Gln Ile Leu Lys Asp Ile Met Asp Asp Tyr Tyr Arg Gly
 50                  55                  60

Phe Ile Ser Glu Thr Leu Ser Ser Ile Asp Asp Ile Asp Trp Thr Ser
 65                  70                  75                  80

Leu Phe Glu Lys Met Glu Ile Gln Leu Lys Asn Gly Asp Asn Lys Asp
                 85                  90                  95

Thr Leu Ile Lys Glu Gln Thr Glu Tyr Arg Lys Ala Ile His Lys Lys
                100                 105                 110

Phe Ala Asn Asp Asp Arg Phe Lys Asn Met Phe Ser Ala Lys Leu Ile
            115                 120                 125

Ser Asp Ile Leu Pro Glu Phe Val Ile His Asn Asn Tyr Ser Ala
130                 135                 140

Ser Glu Lys Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
            195                 200                 205

Ser Leu Ser Asn Asp Asp Ile Asn Lys Ile Ser Gly Asp Met Lys Asp
210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Lys Leu His Lys Gln Ile Leu Cys
            275                 280                 285

Ile Ala Asp Thr Ser Tyr Glu Val Pro Tyr Lys Phe Glu Ser Asp Glu
            290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
            355                 360                 365

His Tyr Asn Asn Ile Leu Pro Gly Asn Gly Lys Ser Lys Ala Asp Lys
            370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
            435                 440                 445

Leu Lys Ala Ser Glu Leu Lys Asn Val Leu Asp Val Ile Met Asn Ala
450                 455                 460

```
Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
            515                 520                 525

Asp Gly Trp Ser Lys Ser Lys Glu Tyr Ser Asn Asn Ala Ile Ile Leu
530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
                580                 585                 590

Pro Lys Val Phe Leu Ser Ser Lys Thr Gly Val Glu Thr Tyr Lys Pro
                595                 600                 605

Ser Ala Tyr Ile Leu Glu Gly Tyr Lys Gln Asn Lys His Ile Lys Ser
610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
                660                 665                 670

Val Glu Leu Gln Gly Tyr Lys Ile Asp Trp Thr Tyr Ile Ser Glu Lys
                675                 680                 685

Asp Ile Asp Leu Leu Gln Glu Lys Gly Gln Leu Tyr Leu Phe Gln Ile
690                 695                 700

Tyr Asn Lys Asp Phe Ser Lys Val Ser Thr Gly Asn Asp Asn Leu His
705                 710                 715                 720

Thr Met Tyr Leu Lys Asn Leu Phe Ser Glu Asn Leu Lys Asp Ile
                725                 730                 735

Val Leu Lys Leu Asn Gly Glu Ala Glu Ile Phe Phe Arg Lys Ser Ser
                740                 745                 750

Ile Lys Asn Pro Ile Ile His Lys Lys Gly Ser Ile Leu Val Asn Arg
                755                 760                 765

Thr Tyr Glu Ala Glu Glu Lys Asp Gln Phe Gly Asn Ile Gln Ile Val
                770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
                820                 825                 830

Arg Tyr Thr Tyr Asp Lys Tyr Phe Leu His Met Pro Ile Thr Ile Asn
                835                 840                 845

Phe Lys Ala Asn Lys Thr Gly Phe Ile Asn Asp Arg Ile Leu Gln Tyr
                850                 855                 860

Ile Ala Lys Glu Lys Asp Leu His Val Ile Gly Ile Asp Arg Gly Glu
865                 870                 875                 880
```

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
    930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
        995                 1000                1005

Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 75
<211> LENGTH: 1263
<212> TYPE: PRT

<213> ORGANISM: Artificial Sequence
<220> FEATURE:
<223> OTHER INFORMATION: MAD70 VARIANT E743I

<400> SEQUENCE: 75

```
Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Lys Glu Asp Glu Leu Arg Gly
        35                  40                  45

Glu Asn Arg Gln Ile Leu Lys Asp Ile Met Asp Tyr Tyr Arg Gly
50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Gly Tyr Arg Lys Ala Ile His Lys Lys
            100                 105                 110

Phe Ala Asn Asp Asp Arg Phe Lys Asn Met Phe Ser Ala Lys Leu Ile
            115                 120                 125

Ser Asp Ile Leu Pro Glu Phe Val Ile His Asn Asn Asn Tyr Ser Ala
            130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Ar

```
                385                 390                 395                 400
Asn Glu Leu Val Ser Asn Tyr Lys Leu Cys Ser Asp Asp Asn Ile Lys
                    405                 410                 415
Ala Glu Thr Tyr Ile His Glu Ile Ser His Ile Leu Asn Asn Phe Glu
                    420                 425                 430
Ala Gln Glu Leu Lys Tyr Asn Pro Glu Ile His Leu Val Glu Ser Glu
                    435                 440                 445
Leu Lys Ala Ser Glu Leu Lys Asn Val Leu Asp Val Ile Met Asn Ala
                    450                 455                 460
Phe His Trp Cys Ser Val Phe Met Thr Glu Glu Leu Val Asp Lys Asp
465                 470                 475                 480
Asn Asn Phe Tyr Ala Glu Leu Glu Glu Ile Tyr Asp Glu Ile Tyr Pro
                    485                 490                 495
Val Ile Ser Leu Tyr Asn Leu Val Arg Asn Tyr Val Thr Gln Lys Pro
                    500                 505                 510
Tyr Ser Thr Lys Lys Ile Lys Leu Asn Phe Gly Ile Pro Thr Leu Ala
                    515                 520                 525
Asp Gly Trp Ser Lys Ser Lys Glu Tyr Ser Asn Asn Ala Ile Ile Leu
                    530                 535                 540
Met Arg Asp Asn Leu Tyr Tyr Leu Gly Ile Phe Asn Ala Lys Asn Lys
545                 550                 555                 560
Pro Asp Lys Lys Ile Ile Glu Gly Asn Thr Ser Glu Asn Lys Gly Asp
                    565                 570                 575
Tyr Lys Lys Met Ile Tyr Asn Leu Leu Pro Gly Pro Asn Lys Met Ile
                    580                 585                 590
Pro Lys Val Phe Leu Ser Ser Lys Thr Gly Val Glu Thr Tyr Lys Pro
                    595                 600                 605
Ser Ala Tyr Ile Leu Glu Gly Tyr Lys Gln Asn Lys His Ile Lys Ser
                    610                 615                 620
Ser Lys Asp Phe Asp Ile Thr Phe Cys His Asp Leu Ile Asp Tyr Phe
625                 630                 635                 640
Lys Asn Cys Ile Ala Ile His Pro Glu Trp Lys Asn Phe Gly Phe Asp
                    645                 650                 655
Phe Ser Asp Thr Ser Thr Tyr Glu Asp Ile Ser Gly Phe Tyr Arg Glu
                    660                 665                 670
Val Glu Leu Gln Gly Tyr Lys Ile Asp Trp Thr Tyr Ile Ser Glu Lys
                    675                 680                 685
Asp Ile Asp Leu Leu Gln Glu Lys Gly Gln Leu Tyr Leu Phe Gln Ile
                    690                 695                 700
Tyr Asn Lys Asp Phe Ser Lys Ser Thr Gly Asn Asp Asn Leu His Thr
705                 710                 715                 720
Thr Met Tyr Leu Lys Asn Leu Phe Ser Glu Asn Leu Lys Asp Ile
                    725                 730                 735
Val Leu Lys Leu Asn Gly Ile Ala Glu Ile Phe Phe Arg Lys Ser Ser
                    740                 745                 750
Ile Lys Asn Pro Ile Ile His Lys Lys Gly Ser Ile Leu Val Asn Arg
                    755                 760                 765
Thr Tyr Glu Ala Glu Glu Lys Asp Gln Phe Gly Asn Ile Gln Ile Val
                    770                 775                 780
Arg Lys Asn Ile Pro Glu Asn Ile Tyr Gln Glu Leu Tyr Lys Tyr Phe
785                 790                 795                 800
Asn Asp Lys Ser Asp Lys Glu Leu Ser Asp Glu Ala Ala Lys Leu Lys
                    805                 810                 815
```

```
Asn Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
        835                 840                 845

Phe Lys Ala Asn Lys Thr Gly Phe Ile Asn Asp Arg Ile Leu Gln Tyr
    850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
    930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
        995                 1000                1005

Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215
```

```
Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260
```

<210> SEQ ID NO 76
<211> LENGTH: 1263
<212> TYPE: PRT
<213> ORGANISM: Artificial Sequence
<220> FEATURE:
<223> OTHER INFORMATION: MAD70 VARIANT K786S

<400> SEQUENCE: 76

```
Met Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
                20                  25                  30

Gln Phe Ile Val Lys Asn Gly Ile Ile Lys Glu Asp Glu Leu Arg Gly
                35                  40                  45

Glu Asn Arg Gln Ile Leu Lys Asp Ile Met Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
                100                 105                 110

Phe Ala Asn Asp Asp Arg Phe Lys Asn Met Phe Ser Ala Lys Leu Ile
                115                 120                 125

Ser Asp Ile Leu Pro Glu Phe Val Ile His Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Ser Cys His Arg Ile Val Asn Asp Asn
                180                 185                 190

Ala Glu Ile Phe Phe Ser Asn Ala Leu Val Tyr Arg Arg Ile Val Lys
                195                 200                 205

Ser Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
                260                 265                 270

Asn Lys Asn Leu Tyr Lys Leu Gln Lys Leu His Lys Gln Ile Leu Cys
    275                 280                 285

Ile Ala Asp Thr Ser Tyr Glu Val Pro Tyr Lys Phe Glu Ser Asp Glu
    290                 295                 300

Glu Val Tyr Gln Ser Val Asn Gly Phe Leu Asp Asn Ile Ser Ser Lys
305                 310                 315                 320
```

```
His Ile Val Glu Arg Leu Arg Lys Ile Gly Asp Asn Tyr Asn Gly Tyr
            325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
            355                 360                 365

His Tyr Asn Asn Ile Leu Pro Gly Asn Gly Lys Ser Lys Ala Asp Lys
            370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
            405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
            435                 440                 445

Leu Lys Ala Ser Glu Leu Lys Asn Val Leu Asp Val Ile Met Asn Ala
            450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
            485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
            515                 520                 525

Asp Gly Trp Ser Lys Ser Lys Glu Tyr Ser Asn Asn Ala Ile Ile Leu
            530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
            565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
            595                 600                 605

Ser Ala Tyr Ile Leu Glu Gly Tyr Lys Gln Asn Lys His Ile Lys Ser
            610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
            645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
            690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
            725                 730                 735

Val Leu Lys Leu Asn Gly Glu Ala Glu Ile Phe Phe Arg Lys Ser Ser
```

```
                740             745             750
Ile Lys Asn Pro Ile Ile His Lys Lys Gly Ser Ile Leu Val Asn Arg
            755             760             765

Thr Tyr Glu Ala Glu Lys Asp Gln Phe Gly Asn Ile Gln Ile Val
    770             775             780

Arg Ser Asn Ile Pro Glu Asn Ile Tyr Gln Glu Leu Tyr Lys Tyr Phe
785             790             795             800

Asn Asp Lys Ser Asp Lys Glu Leu Ser Asp Glu Ala Ala Lys Leu Lys
            805             810             815

Asn Val Val Gly His His Glu Ala Ala Thr Asn Ile Val Lys Asp Tyr
            820             825             830

Arg Tyr Thr Tyr Asp Lys Tyr Phe Leu His Met Pro Ile Thr Ile Asn
            835             840             845

Phe Lys Ala Asn Lys Thr Gly Phe Ile Asn Asp Arg Ile Leu Gln Tyr
            850             855             860

Ile Ala Lys Glu Lys Asp Leu His Val Ile Gly Ile Asp Arg Gly Glu
865             870             875             880

Arg Asn Leu Ile Tyr Val Ser Val Ile Asp Thr Cys Gly Asn Ile Val
            885             890             895

Glu Gln Lys Ser Phe Asn Ile Val Asn Gly Tyr Asp Tyr Gln Ile Lys
            900             905             910

Leu Lys Gln Gln Glu Gly Ala Arg Gln Ile Ala Arg Lys Glu Trp Lys
            915             920             925

Glu Ile Gly Lys Ile Lys Glu Ile Lys Glu Gly Tyr Leu Ser Leu Val
            930             935             940

Ile His Glu Ile Ser Lys Met Val Ile Lys Tyr Asn Ala Ile Ile Ala
945             950             955             960

Met Glu Asp Leu Ser Tyr Gly Phe Lys Lys Gly Arg Phe Lys Val Glu
            965             970             975

Arg Gln Val Tyr Gln Lys Phe Glu Thr Met Leu Ile Asn Lys Leu Asn
            980             985             990

Tyr Leu Val Phe Lys Asp Ile Ser Ile Thr Glu Asn Gly Gly Leu Leu
            995             1000            1005

Lys Gly Tyr Gln Leu Thr Tyr Ile Pro Asp Lys Leu Lys Asn Val
    1010            1015            1020

Gly His Gln Cys Gly Cys Ile Phe Tyr Val Pro Ala Ala Tyr Thr
    1025            1030            1035

Ser Lys Ile Asp Pro Thr Thr Gly Phe Val Asn Ile Phe Lys Phe
    1040            1045            1050

Lys Asp Leu Thr Val Asp Ala Lys Arg Glu Phe Ile Lys Lys Phe
    1055            1060            1065

Asp Ser Ile Arg Tyr Asp Ser Glu Lys Asn Leu Phe Cys Phe Thr
    1070            1075            1080

Phe Asp Tyr Asn Asn Phe Ile Thr Gln Asn Thr Val Met Ser Lys
    1085            1090            1095

Ser Ser Trp Ser Val Tyr Thr Tyr Gly Val Arg Ile Lys Arg Arg
    1100            1105            1110

Phe Val Asn Gly Arg Phe Ser Asn Glu Ser Asp Thr Ile Asp Ile
    1115            1120            1125

Thr Lys Asp Met Glu Lys Thr Leu Glu Met Thr Asp Ile Asn Trp
    1130            1135            1140

Arg Asp Gly His Asp Leu Arg Gln Asp Ile Ile Asp Tyr Glu Ile
    1145            1150            1155
```

```
Val Gln His Ile Phe Glu Ile Phe Arg Leu Thr Val Gln Met Arg
        1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 77
<211> LENGTH: 1263
<212> TYPE: PRT
<213> ORGANISM: Artificial Sequence
<220> FEATURE:
<223> OTHER INFORMATION: MAD70 VARIANT : K853R

<400> SEQUENCE: 77

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
                20                  25                  30

Gln Phe Ile Val Lys Asn Gly Ile Ile Lys Glu Asp Glu Leu Arg Gly
            35                  40                  45

Glu Asn Arg Gln Ile Leu Lys Asp Ile Met Asp Tyr Tyr Arg Gly
        50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255
```

```
Gly Lys Val Asn Ser Phe Met Asn Leu Tyr Cys Gln Lys Asn Lys Glu
            260                 265                 270

Asn Lys Asn Leu Tyr Lys Leu Gln Lys Leu His Lys Gln Ile Leu Cys
        275                 280                 285

Ile Ala Asp Thr Ser Tyr Glu Val Pro Tyr Lys Phe Glu Ser Asp Glu
    290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
    370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
    450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
        515                 520                 525

Asp Gly Trp Ser Lys Ser Lys Glu Tyr Ser Asn Asn Ala Ile Ile Leu
    530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
        595                 600                 605

Ser Ala Tyr Ile Leu Glu Gly Tyr Lys Gln Asn Lys His Ile Lys Ser
    610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670
```

-continued

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
            690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
            755                 760                 765

Thr Tyr Glu Ala Glu Glu Lys Asp Gln Phe Gly Asn Ile Gln Ile Val
            770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
            835                 840                 845

Phe Lys Ala Asn Arg Thr Gly Phe Ile Asn Asp Arg Ile Leu Gln Tyr
            850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
            995                 1000                1005

Lys Gly Tyr Gln Leu Thr Tyr Ile Pro Asp Lys Leu Lys Asn Val
            1010                1015                1020

Gly His Gln Cys Gly Cys Ile Phe Tyr Val Pro Ala Ala Tyr Thr
            1025                1030                1035

Ser Lys Ile Asp Pro Thr Thr Gly Phe Val Asn Ile Phe Lys Phe
            1040                1045                1050

Lys Asp Leu Thr Val Asp Ala Lys Arg Glu Phe Ile Lys Lys Phe
            1055                1060                1065

Asp Ser Ile Arg Tyr Asp Ser Glu Lys Asn Leu Phe Cys Phe Thr
            1070                1075                1080

Phe Asp Tyr Asn Asn Phe Ile Thr Gln Asn Thr Val Met Ser Lys

-continued

```
              1085                1090                1095

Ser Ser Trp Ser Val Tyr Thr Tyr Gly Val Arg Ile Lys Arg Arg
        1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260
```

<210> SEQ ID NO 78
<211> LENGTH: 1263
<212> TYPE: PRT
<213> ORGANISM: Artificial Sequence
<220> FEATURE:
<223> OTHER INFORMATION: MAD70 VARIANT R1113F

<400> SEQUENCE: 78

```
Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Ile Asp Trp Thr Ser
65                  70                  75              80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Asn Tyr Ser Ala
    130                 135                 140

Ser Glu Lys Glu Glu Lys Thr Gln Val Ile Lys Leu Phe Ser Arg Phe
145                 150                 155             160

Ala Thr Ser Phe Lys Asp Tyr Phe Lys Asn Arg Ala Asn Cys Phe Ser
                165                 170                 175

Ala Asp Asp Ile Ser Ser Ser Ser Cys His Arg Ile Val Asn Asp Asn
```

```
            180             185             190
Ala Glu Ile Phe Phe Ser Asn Ala Leu Val Tyr Arg Arg Ile Val Lys
            195             200             205
Ser Leu Ser Asn Asp Asp Ile Asn Lys Ile Ser Gly Asp Met Lys Asp
            210             215             220
Ser Leu Lys Glu Met Ser Leu Glu Glu Ile Tyr Ser Tyr Glu Lys Tyr
225             230             235             240
Gly Glu Phe Ile Thr Gln Glu Gly Ile Ser Phe Tyr Asn Asp Ile Cys
            245             250             255
Gly Lys Val Asn Ser Phe Met Asn Leu Tyr Cys Gln Lys Asn Lys Glu
            260             265             270
Asn Lys Asn Leu Tyr Lys Leu Gln Lys Leu His Lys Gln Ile Leu Cys
            275             280             285
Ile Ala Asp Thr Ser Tyr Glu Val Pro Tyr Lys Phe Glu Ser Asp Glu
            290             295             300
Glu Val Tyr Gln Ser Val Asn Gly Phe Leu Asp Asn Ile Ser Ser Lys
305             310             315             320
His Ile Val Glu Arg Leu Arg Lys Ile Gly Asp Asn Tyr Asn Gly Tyr
            325             330             335
Asn Leu Asp Lys Ile Tyr Ile Val Ser Lys Phe Tyr Glu Ser Val Ser
            340             345             350
Gln Lys Thr Tyr Arg Asp Trp Glu Thr Ile Asn Thr Ala Leu Glu Ile
            355             360             365
His Tyr Asn Asn Ile Leu Pro Gly Asn Gly Lys Ser Lys Ala Asp Lys
            370             375             380
Val Lys Lys Ala Val Lys Asn Asp Leu Gln Lys Ser Ile Thr Glu Ile
385             390             395             400
Asn Glu Leu Val Ser Asn Tyr Lys Leu Cys Ser Asp Asp Asn Ile Lys
            405             410             415
Ala Glu Thr Tyr Ile His Glu Ile Ser His Ile Leu Asn Asn Phe Glu
            420             425             430
Ala Gln Glu Leu Lys Tyr Asn Pro Glu Ile His Leu Val Glu Ser Glu
            435             440             445
Leu Lys Ala Ser Glu Leu Lys Asn Val Leu Asp Val Ile Met Asn Ala
            450             455             460
Phe His Trp Cys Ser Val Phe Met Thr Glu Glu Leu Val Asp Lys Asp
465             470             475             480
Asn Asn Phe Tyr Ala Glu Leu Glu Glu Ile Tyr Asp Glu Ile Tyr Pro
            485             490             495
Val Ile Ser Leu Tyr Asn Leu Val Arg Asn Tyr Val Thr Gln Lys Pro
            500             505             510
Tyr Ser Thr Lys Lys Ile Lys Leu Asn Phe Gly Ile Pro Thr Leu Ala
            515             520             525
Asp Gly Trp Ser Lys Ser Lys Glu Tyr Ser Asn Asn Ala Ile Ile Leu
            530             535             540
Met Arg Asp Asn Leu Tyr Tyr Leu Gly Ile Phe Asn Ala Lys Asn Lys
545             550             555             560
Pro Asp Lys Lys Ile Ile Glu Gly Asn Thr Ser Glu Asn Lys Gly Asp
            565             570             575
Tyr Lys Lys Met Ile Tyr Asn Leu Leu Pro Gly Pro Asn Lys Met Ile
            580             585             590
Pro Lys Val Phe Leu Ser Ser Lys Thr Gly Val Glu Thr Tyr Lys Pro
            595             600             605
```

```
Ser Ala Tyr Ile Leu Glu Gly Tyr Lys Gln Asn Lys His Ile Lys Ser
    610                 615                 620
Ser Lys Asp Phe Asp Ile Thr Phe Cys His Asp Leu Ile Asp Tyr Phe
625                 630                 635                 640
Lys Asn Cys Ile Ala Ile His Pro Glu Trp Lys Asn Phe Gly Phe Asp
                645                 650                 655
Phe Ser Asp Thr Ser Thr Tyr Glu Asp Ile Ser Gly Phe Tyr Arg Glu
            660                 665                 670
Val Glu Leu Gln Gly Tyr Lys Ile Asp Trp Thr Tyr Ile Ser Glu Lys
        675                 680                 685
Asp Ile Asp Leu Leu Gln Glu Lys Gly Gln Leu Tyr Leu Phe Gln Ile
    690                 695                 700
Tyr Asn Lys Asp Phe Ser Lys Lys Ser Thr Gly Asn Asp Asn Leu His
705                 710                 715                 720
Thr Met Tyr Leu Lys Asn Leu Phe Ser Glu Glu Asn Leu Lys Asp Ile
                725                 730                 735
Val Leu Lys Leu Asn Gly Glu Ala Glu Ile Phe Phe Arg Lys Ser Ser
            740                 745                 750
Ile Lys Asn Pro Ile Ile His Lys Lys Gly Ser Ile Leu Val Asn Arg
        755                 760                 765
Thr Tyr Glu Ala Glu Lys Asp Gln Phe Gly Asn Ile Gln Ile Val
    770                 775                 780
Arg Lys Asn Ile Pro Glu Asn Ile Tyr Gln Glu Leu Tyr Lys Tyr Phe
785                 790                 795                 800
Asn Asp Lys Ser Asp Lys Glu Leu Ser Asp Glu Ala Ala Lys Leu Lys
                805                 810                 815
Asn Val Val Gly His His Glu Ala Ala Thr Asn Ile Val Lys Asp Tyr
            820                 825                 830
Arg Tyr Thr Tyr Asp Lys Tyr Phe Leu His Met Pro Ile Thr Ile Asn
        835                 840                 845
Phe Lys Ala Asn Lys Thr Gly Phe Ile Asn Asp Arg Ile Leu Gln Tyr
    850                 855                 860
Ile Ala Lys Glu Lys Asp Leu His Val Ile Gly Ile Asp Arg Gly Glu
865                 870                 875                 880
Arg Asn Leu Ile Tyr Val Ser Val Ile Asp Thr Cys Gly Asn Ile Val
                885                 890                 895
Glu Gln Lys Ser Phe Asn Ile Val Asn Gly Tyr Asp Tyr Gln Ile Lys
            900                 905                 910
Leu Lys Gln Gln Glu Gly Ala Arg Gln Ile Ala Arg Lys Glu Trp Lys
        915                 920                 925
Glu Ile Gly Lys Ile Lys Glu Ile Lys Glu Gly Tyr Leu Ser Leu Val
    930                 935                 940
Ile His Glu Ile Ser Lys Met Val Ile Lys Tyr Asn Ala Ile Ile Ala
945                 950                 955                 960
Met Glu Asp Leu Ser Tyr Gly Phe Lys Lys Gly Arg Phe Lys Val Glu
                965                 970                 975
Arg Gln Val Tyr Gln Lys Phe Glu Thr Met Leu Ile Asn Lys Leu Asn
            980                 985                 990
Tyr Leu Val Phe Lys Asp Ile Ser Ile Thr Glu Asn Gly Gly Leu Leu
        995                 1000                1005
Lys Gly Tyr Gln Leu Thr Tyr Ile Pro Asp Lys Leu Lys Asn Val
    1010                1015                1020
```

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 79
<211> LENGTH: 1263
<212> TYPE: PRT
<213> ORGANISM: Artificial Sequence
<220> FEATURE:
<223> OTHER INFORMATION: MAD70 VARIANT S124T, K511I, N589H, K712V,
      K853R, H946W

<400> SEQUENCE: 79

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
                20                  25                  30

Gln Phe Ile Val Lys Asn Gly Ile Ile Lys Glu Asp Glu Leu Arg Gly
            35                  40                  45

Glu Asn Arg Gln Ile Leu Lys Asp Ile Met Asp Asp Tyr Tyr Arg Gly
        50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

```
Phe Ala Asn Asp Asp Arg Phe Lys Asn Met Phe Thr Ala Lys Leu Ile
        115                 120                 125

Ser Asp Ile Leu Pro Glu Phe Val Ile His Asn Asn Asn Tyr Ser Ala
130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
                180                 185                 190

Ala Glu Ile Phe Phe Ser Asn Ala Leu Val Tyr Arg Arg Ile Val Lys
                195                 200                 205

Ser Leu Ser Asn Asp Asp Ile Asn Lys Ile Ser Gly Asp Met Lys Asp
210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
                260                 265                 270

Asn Lys Asn Leu Tyr Lys Leu Gln Lys Leu His Lys Gln Ile Leu Cys
        275                 280                 285

Ile Ala Asp Thr Ser Tyr Glu Val Pro Tyr Lys Phe Glu Ser Asp Glu
290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
                340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
        370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Ile Pro
                500                 505                 510

Tyr Ser Thr Lys Lys Ile Lys Leu Asn Phe Gly Ile Pro Thr Leu Ala
        515                 520                 525
```

-continued

Asp Gly Trp Ser Lys Ser Lys Glu Tyr Ser Asn Asn Ala Ile Ile Leu
    530             535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
            565                 570                 575

Tyr Lys Lys Met Ile Tyr Asn Leu Leu Pro Gly Pro His Lys Met Ile
            580                 585                 590

Pro Lys Val Phe Leu Ser Ser Lys Thr Gly Val Glu Thr Tyr Lys Pro
        595                 600                 605

Ser Ala Tyr Ile Leu Glu Gly Tyr Lys Gln Asn Lys His Ile Lys Ser
    610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
            645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Val Ser Thr Gly Asn Asp Asn Leu His
705                 710                 715                 720

Thr Met Tyr Leu Lys Asn Leu Phe Ser Glu Glu Asn Leu Lys Asp Ile
            725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
        755                 760                 765

Thr Tyr Glu Ala Glu Glu Lys Asp Gln Phe Gly Asn Ile Gln Ile Val
    770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
            805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
        835                 840                 845

Phe Lys Ala Asn Arg Thr Gly Phe Ile Asn Asp Arg Ile Leu Gln Tyr
    850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
            885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
    930                 935                 940

Ile Trp Glu Ile Ser Lys Met Val Ile Lys Tyr Asn Ala Ile Ile Ala

Met Glu Asp Leu Ser Tyr Gly Phe Lys Lys Gly Arg Phe Lys Val Glu
945                 950                 955                 960

Arg Gln Val Tyr Gln Lys Phe Glu Thr Met Leu Ile Asn Lys Leu Asn
            965                 970                 975

Tyr Leu Val Phe Lys Asp Ile Ser Ile Thr Glu Asn Gly Gly Leu Leu
        980                 985                 990

Lys Gly Tyr Gln Leu Thr Tyr Ile Pro Asp Lys Leu Lys Asn Val
    995                 1000                1005

Gly His Gln Cys Gly Cys Ile Phe Tyr Val Pro Ala Ala Tyr Thr
1010                1015                1020

Ser Lys Ile Asp Pro Thr Thr Gly Phe Val Asn Ile Phe Lys Phe
1025                1030                1035

Lys Asp Leu Thr Val Asp Ala Lys Arg Glu Phe Ile Lys Lys Phe
1040                1045                1050

Asp Ser Ile Arg Tyr Asp Ser Glu Lys Asn Leu Phe Cys Phe Thr
1055                1060                1065

Phe Asp Tyr Asn Asn Phe Ile Thr Gln Asn Thr Val Met Ser Lys
1070                1075                1080

Ser Ser Trp Ser Val Tyr Thr Tyr Gly Val Arg Ile Lys Arg Arg
1085                1090                1095

Phe Val Asn Gly Arg Phe Ser Asn Glu Ser Asp Thr Ile Asp Ile
1100                1105                1110

Thr Lys Asp Met Glu Lys Thr Leu Glu Met Thr Asp Ile Asn Trp
1115                1120                1125

Arg Asp Gly His Asp Leu Arg Gln Asp Ile Ile Asp Tyr Glu Ile
1130                1135                1140

Val Gln His Ile Phe Glu Ile Phe Arg Leu Thr Val Gln Met Arg
1145                1150                1155

Asn Ser Leu Ser Glu Leu Glu Asp Arg Asp Tyr Asp Arg Leu Ile
1160                1165                1170

Ser Pro Val Leu Asn Glu Asn Ile Phe Tyr Asp Ser Ala Lys
1175                1180                1185

Ala Gly Asp Ala Leu Pro Lys Asp Ala Asp Ala Asn Gly Ala Tyr
1190                1195                1200

Cys Ile Ala Leu Lys Gly Leu Tyr Glu Ile Lys Gln Ile Thr Glu
1205                1210                1215

Asn Trp Lys Glu Asp Gly Lys Phe Ser Arg Asp Lys Leu Lys Ile
1220                1225                1230

Ser Asn Lys Asp Trp Phe Asp Phe Ile Gln Asn Lys Arg Tyr Leu
1235                1240                1245

<210> SEQ ID NO 80
<211> LENGTH: 1263
<212> TYPE: PRT
<213> ORGANISM: Artificial Sequence
<220> FEATURE:
<223> OTHER INFORMATION: MAD70 VARIANT S124T, K511I, N589H, K786S, H946K, R1113F

<400> SEQUENCE: 80

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

-continued

```
Gln Phe Ile Val Lys Asn Gly Ile Lys Glu Asp Glu Leu Arg Gly
         35                  40                  45

Glu Asn Arg Gln Ile Leu Lys Asp Ile Met Asp Tyr Tyr Arg Gly
 50                  55                  60

Phe Ile Ser Glu Thr Leu Ser Ser Ile Asp Asp Ile Asp Trp Thr Ser
 65                  70                  75                  80

Leu Phe Glu Lys Met Glu Ile Gln Leu Lys Asn Gly Asp Asn Lys Asp
                 85                  90                  95

Thr Leu Ile Lys Glu Gln Thr Glu Tyr Arg Lys Ala Ile His Lys Lys
                100                 105                 110

Phe Ala Asn Asp Asp Arg Phe Lys Asn Met Phe Thr Ala Lys Leu Ile
            115                 120                 125

Ser Asp Ile Leu Pro Glu Phe Val Ile His Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Lys Leu His Lys Gln Ile Leu Cys
        275                 280                 285

Ile Ala Asp Thr Ser Tyr Glu Val Pro Tyr Lys Phe Glu Ser Asp Glu
290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
```

```
            450                 455                 460
Phe His Trp Cys Ser Val Phe Met Thr Glu Glu Leu Val Asp Lys Asp
465                 470                 475                 480
Asn Asn Phe Tyr Ala Glu Leu Glu Glu Ile Tyr Asp Glu Ile Tyr Pro
                    485                 490                 495
Val Ile Ser Leu Tyr Asn Leu Val Arg Asn Tyr Val Thr Gln Ile Pro
                500                 505                 510
Tyr Ser Thr Lys Lys Ile Lys Leu Asn Phe Gly Ile Pro Thr Leu Ala
            515                 520                 525
Asp Gly Trp Ser Lys Ser Lys Glu Tyr Ser Asn Asn Ala Ile Ile Leu
        530                 535                 540
Met Arg Asp Asn Leu Tyr Tyr Leu Gly Ile Phe Asn Ala Lys Asn Lys
545                 550                 555                 560
Pro Asp Lys Lys Ile Ile Glu Gly Asn Thr Ser Glu Asn Lys Gly Asp
                    565                 570                 575
Tyr Lys Lys Met Ile Tyr Asn Leu Leu Pro Gly Pro His Lys Met Ile
                580                 585                 590
Pro Lys Val Phe Leu Ser Ser Lys Thr Gly Val Glu Thr Tyr Lys Pro
            595                 600                 605
Ser Ala Tyr Ile Leu Glu Gly Tyr Lys Gln Asn Lys His Ile Lys Ser
        610                 615                 620
Ser Lys Asp Phe Asp Ile Thr Phe Cys His Asp Leu Ile Asp Tyr Phe
625                 630                 635                 640
Lys Asn Cys Ile Ala Ile His Pro Glu Trp Lys Asn Phe Gly Phe Asp
                    645                 650                 655
Phe Ser Asp Thr Ser Thr Tyr Glu Asp Ile Ser Gly Phe Tyr Arg Glu
                660                 665                 670
Val Glu Leu Gln Gly Tyr Lys Ile Asp Trp Thr Tyr Ile Ser Glu Lys
            675                 680                 685
Asp Ile Asp Leu Leu Gln Glu Lys Gly Gln Leu Tyr Leu Phe Gln Ile
        690                 695                 700
Tyr Asn Lys Asp Phe Ser Lys Lys Ser Thr Gly Asn Asp Asn Leu His
705                 710                 715                 720
Thr Met Tyr Leu Lys Asn Leu Phe Ser Glu Glu Asn Leu Lys Asp Ile
                    725                 730                 735
Val Leu Lys Leu Asn Gly Glu Ala Glu Ile Phe Phe Arg Lys Ser Ser
                740                 745                 750
Ile Lys Asn Pro Ile Ile His Lys Lys Gly Ser Ile Leu Val Asn Arg
            755                 760                 765
Thr Tyr Glu Ala Glu Glu Lys Asp Gln Phe Gly Asn Ile Gln Ile Val
        770                 775                 780
Arg Ser Asn Ile Pro Glu Asn Ile Tyr Gln Glu Leu Tyr Lys Tyr Phe
785                 790                 795                 800
Asn Asp Lys Ser Asp Lys Glu Leu Ser Asp Glu Ala Ala Lys Leu Lys
                    805                 810                 815
Asn Val Val Gly His His Glu Ala Ala Thr Asn Ile Val Lys Asp Tyr
                820                 825                 830
Arg Tyr Thr Tyr Asp Lys Tyr Phe Leu His Met Pro Ile Thr Ile Asn
            835                 840                 845
Phe Lys Ala Asn Lys Thr Gly Phe Ile Asn Asp Arg Ile Leu Gln Tyr
        850                 855                 860
Ile Ala Lys Glu Lys Asp Leu His Val Ile Gly Ile Asp Arg Gly Glu
865                 870                 875                 880
```

```
Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
930                 935                 940

Ile Lys Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
        995                 1000                1005

Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Phe
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260
```

<210> SEQ ID NO 81
<211> LENGTH: 1263

<212> TYPE: PRT
<213> ORGANISM: Artificial Sequence
<220> FEATURE:
<223> OTHER INFORMATION: MAD70 VARIANT K511H, N589H, K853R, K1021L, D1181E, D1183E

<400> SEQUENCE: 81

```
Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Lys Leu His Lys Gln Ile Leu Cys
        275                 280                 285

Ile Ala Asp Thr Ser Tyr Glu Val Pro Tyr Lys Phe Glu Ser Asp Glu
290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
370                 375                 380
```

```
Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
            405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
    450                 455                 460

Phe His Trp Cys Ser Val Phe Met Thr Glu Leu Val Asp Lys Asp
465                 470                 475                 480

Asn Asn Phe Tyr Ala Glu Leu Glu Glu Ile Tyr Asp Glu Ile Tyr Pro
            485                 490                 495

Val Ile Ser Leu Tyr Asn Leu Val Arg Asn Tyr Val Thr Gln His Pro
            500                 505                 510

Tyr Ser Thr Lys Lys Ile Lys Leu Asn Phe Gly Ile Pro Thr Leu Ala
        515                 520                 525

Asp Gly Trp Ser Lys Ser Lys Glu Tyr Ser Asn Asn Ala Ile Ile Leu
    530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
            565                 570                 575

Tyr Lys Lys Met Ile Tyr Asn Leu Leu Pro Gly Pro His Lys Met Ile
            580                 585                 590

Pro Lys Val Phe Leu Ser Ser Lys Thr Gly Val Glu Thr Tyr Lys Pro
        595                 600                 605

Ser Ala Tyr Ile Leu Glu Gly Tyr Lys Gln Asn Lys His Ile Lys Ser
    610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
            645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
            725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
        755                 760                 765

Thr Tyr Glu Ala Glu Glu Lys Asp Gln Phe Gly Asn Ile Gln Ile Val
    770                 775                 780

Arg Lys Asn Ile Pro Glu Asn Ile Tyr Gln Glu Leu Tyr Lys Tyr Phe
785                 790                 795                 800
```

```
Asn Asp Lys Ser Asp Lys Glu Leu Ser Asp Glu Ala Ala Lys Leu Lys
            805                 810                 815
Asn Val Val Gly His His Glu Ala Ala Thr Asn Ile Val Lys Asp Tyr
        820                 825                 830
Arg Tyr Thr Tyr Asp Lys Tyr Phe Leu His Met Pro Ile Thr Ile Asn
        835                 840                 845
Phe Lys Ala Asn Arg Thr Gly Phe Ile Asn Asp Arg Ile Leu Gln Tyr
        850                 855                 860
Ile Ala Lys Glu Lys Asp Leu His Val Ile Gly Ile Asp Arg Gly Glu
865                 870                 875                 880
Arg Asn Leu Ile Tyr Val Ser Val Ile Asp Thr Cys Gly Asn Ile Val
                885                 890                 895
Glu Gln Lys Ser Phe Asn Ile Val Asn Gly Tyr Asp Tyr Gln Ile Lys
        900                 905                 910
Leu Lys Gln Gln Glu Gly Ala Arg Gln Ile Ala Arg Lys Glu Trp Lys
        915                 920                 925
Glu Ile Gly Lys Ile Lys Glu Ile Lys Glu Gly Tyr Leu Ser Leu Val
        930                 935                 940
Ile His Glu Ile Ser Lys Met Val Ile Lys Tyr Asn Ala Ile Ile Ala
945                 950                 955                 960
Met Glu Asp Leu Ser Tyr Gly Phe Lys Lys Gly Arg Phe Lys Val Glu
                965                 970                 975
Arg Gln Val Tyr Gln Lys Phe Glu Thr Met Leu Ile Asn Lys Leu Asn
        980                 985                 990
Tyr Leu Val Phe Lys Asp Ile Ser Ile Thr Glu Asn Gly Gly Leu Leu
        995                 1000                1005
Lys Gly Tyr Gln Leu Thr Tyr Ile Pro Asp Lys Leu Leu Asn Val
        1010                1015                1020
Gly His Gln Cys Gly Cys Ile Phe Tyr Val Pro Ala Ala Tyr Thr
        1025                1030                1035
Ser Lys Ile Asp Pro Thr Thr Gly Phe Val Asn Ile Phe Lys Phe
        1040                1045                1050
Lys Asp Leu Thr Val Asp Ala Lys Arg Glu Phe Ile Lys Lys Phe
        1055                1060                1065
Asp Ser Ile Arg Tyr Asp Ser Glu Lys Asn Leu Phe Cys Phe Thr
        1070                1075                1080
Phe Asp Tyr Asn Asn Phe Ile Thr Gln Asn Thr Val Met Ser Lys
        1085                1090                1095
Ser Ser Trp Ser Val Tyr Thr Tyr Gly Val Arg Ile Lys Arg Arg
        1100                1105                1110
Phe Val Asn Gly Arg Phe Ser Asn Glu Ser Asp Thr Ile Asp Ile
        1115                1120                1125
Thr Lys Asp Met Glu Lys Thr Leu Glu Met Thr Asp Ile Asn Trp
        1130                1135                1140
Arg Asp Gly His Asp Leu Arg Gln Asp Ile Ile Asp Tyr Glu Ile
        1145                1150                1155
Val Gln His Ile Phe Glu Ile Phe Arg Leu Thr Val Gln Met Arg
        1160                1165                1170
Asn Ser Leu Ser Glu Leu Glu Arg Glu Tyr Asp Arg Leu Ile
        1175                1180                1185
Ser Pro Val Leu Asn Glu Asn Asn Ile Phe Tyr Asp Ser Ala Lys
        1190                1195                1200
Ala Gly Asp Ala Leu Pro Lys Asp Ala Asp Ala Asn Gly Ala Tyr
```

<210> SEQ ID NO 82
<211> LENGTH: 1263
<212> TYPE: PRT
<213> ORGANISM: Artificial Sequence
<220> FEATURE:
<223> OTHER INFORMATION: MAD70 VARIANT K95L, S124T, K511I, N589H

<400> SEQUENCE: 82

```
Cys Ile Ala Leu Lys Gly Leu Tyr Glu Ile Lys Gln Ile Thr Glu
        1220                1225                1230
Asn Trp Lys Glu Asp Gly Lys Phe Ser Arg Asp Lys Leu Lys Ile
        1235                1240                1245
Ser Asn Lys Asp Trp Phe Asp Phe Ile Gln Asn Lys Arg Tyr Leu
        1250                1255                1260

Met Asn Asn Gly Thr Asn Asn Phe Gln Asn Phe Ile Gly Ile Ser Ser
 1               5                   10                  15
Leu Gln Lys Thr Leu Arg Asn Ala Leu Ile Pro Thr Glu Thr Thr Gln
                20                  25                  30

```
                305                 310                 315                 320
        His Ile Val Glu Arg Leu Arg Lys Ile Gly Asp Asn Tyr Asn Gly Tyr
                        325                 330                 335

Asn Leu Asp Lys Ile Tyr Ile Val Ser Lys Phe Tyr Glu Ser Val Ser
                        340                 345                 350

Gln Lys Thr Tyr Arg Asp Trp Glu Thr Ile Asn Thr Ala Leu Glu Ile
                        355                 360                 365

His Tyr Asn Asn Ile Leu Pro Gly Asn Gly Lys Ser Lys Ala Asp Lys
                        370                 375                 380

Val Lys Lys Ala Val Lys Asn Asp Leu Gln Lys Ser Ile Thr Glu Ile
        385                 390                 395                 400

Asn Glu Leu Val Ser Asn Tyr Lys Leu Cys Ser Asp Asp Asn Ile Lys
                        405                 410                 415

Ala Glu Thr Tyr Ile His Glu Ile Ser His Ile Leu Asn Asn Phe Glu
                        420                 425                 430

Ala Gln Glu Leu Lys Tyr Asn Pro Glu Ile His Leu Val Glu Ser Glu
                        435                 440                 445

Leu Lys Ala Ser Glu Leu Lys Asn Val Leu Asp Val Ile Met Asn Ala
                450                 455                 460

Phe His Trp Cys Ser Val Phe Met Thr Glu Glu Leu Val Asp Lys Asp
        465                 470                 475                 480

Asn Asn Phe Tyr Ala Glu Leu Glu Glu Ile Tyr Asp Glu Ile Tyr Pro
                        485                 490                 495

Val Ile Ser Leu Tyr Asn Leu Val Arg Asn Tyr Val Thr Gln Ile Pro
                        500                 505                 510

Tyr Ser Thr Lys Lys Ile Lys Leu Asn Phe Gly Ile Pro Thr Leu Ala
                        515                 520                 525

Asp Gly Trp Ser Lys Ser Lys Glu Tyr Ser Asn Asn Ala Ile Ile Leu
                        530                 535                 540

Met Arg Asp Asn Leu Tyr Tyr Leu Gly Ile Phe Asn Ala Lys Asn Lys
        545                 550                 555                 560

Pro Asp Lys Lys Ile Ile Glu Gly Asn Thr Ser Glu Asn Lys Gly Asp
                        565                 570                 575

Tyr Lys Lys Met Ile Tyr Asn Leu Leu Pro Gly Pro His Lys Met Ile
                        580                 585                 590

Pro Lys Val Phe Leu Ser Ser Lys Thr Gly Val Glu Thr Tyr Lys Pro
                        595                 600                 605

Ser Ala Tyr Ile Leu Glu Gly Tyr Lys Gln Asn Lys His Ile Lys Ser
                        610                 615                 620

Ser Lys Asp Phe Asp Ile Thr Phe Cys His Asp Leu Ile Asp Tyr Phe
        625                 630                 635                 640

Lys Asn Cys Ile Ala Ile His Pro Glu Trp Lys Asn Phe Gly Phe Asp
                        645                 650                 655

Phe Ser Asp Thr Ser Thr Tyr Glu Asp Ile Ser Gly Phe Tyr Arg Glu
                        660                 665                 670

Val Glu Leu Gln Gly Tyr Lys Ile Asp Trp Thr Tyr Ile Ser Glu Lys
                        675                 680                 685

Asp Ile Asp Leu Leu Gln Glu Lys Gly Gln Leu Tyr Leu Phe Gln Ile
                        690                 695                 700

Tyr Asn Lys Asp Phe Ser Lys Lys Ser Thr Gly Asn Asp Asn Leu His
        705                 710                 715                 720

Thr Met Tyr Leu Lys Asn Leu Phe Ser Glu Glu Asn Leu Lys Asp Ile
                        725                 730                 735
```

```
Val Leu Lys Leu Asn Gly Glu Ala Glu Ile Phe Phe Arg Lys Ser Ser
            740                 745                 750

Ile Lys Asn Pro Ile Ile His Lys Gly Ser Ile Leu Val Asn Arg
        755                 760                 765

Thr Tyr Glu Ala Glu Lys Asp Gln Phe Gly Asn Ile Gln Ile Val
    770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
                820                 825                 830

Arg Tyr Thr Tyr Asp Lys Tyr Phe Leu His Met Pro Ile Thr Ile Asn
            835                 840                 845

Phe Lys Ala Asn Lys Thr Gly Phe Ile Asn Asp Arg Ile Leu Gln Tyr
    850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
                900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
        995                 1000                1005

Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140
```

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 83
<211> LENGTH: 1263
<212> TYPE: PRT
<213> ORGANISM: Artificial Sequence
<220> FEATURE:
<223> OTHER INFORMATION: MAD70 VARIANT S124T, K511I, N589H, K712L,
      K786S, K1021V

<400> SEQUENCE: 83

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Lys Glu Asp Glu Leu Arg Gly
            35                  40                  45

Glu Asn Arg Gln Ile Leu Lys Asp Ile Met Asp Asp Tyr Tyr Arg Gly
        50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Thr Ala Lys Leu Ile
        115                 120                 125

Ser Asp Ile Leu Pro Glu Phe Val Ile His Asn Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
225                 230                 235                 240

-continued

```
Gly Glu Phe Ile Thr Gln Gly Ile Ser Phe Tyr Asn Asp Ile Cys
            245                 250                 255

Gly Lys Val Asn Ser Phe Met Asn Leu Tyr Cys Gln Lys Asn Lys Glu
        260                 265                 270

Asn Lys Asn Leu Tyr Lys Leu Gln Lys Leu His Lys Gln Ile Leu Cys
        275                 280                 285

Ile Ala Asp Thr Ser Tyr Glu Val Pro Tyr Lys Phe Glu Ser Asp Glu
        290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asn Tyr Asn Gly Tyr
            325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
        370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
            405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
            485                 490                 495

Val Ile Ser Leu Tyr Asn Leu Val Arg Asn Tyr Val Thr Gln Ile Pro
            500                 505                 510

Tyr Ser Thr Lys Lys Ile Lys Leu Asn Phe Gly Ile Pro Thr Leu Ala
        515                 520                 525

Asp Gly Trp Ser Lys Ser Lys Glu Tyr Ser Asn Asn Ala Ile Ile Leu
        530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
            565                 570                 575

Tyr Lys Lys Met Ile Tyr Asn Leu Leu Pro Gly Pro His Lys Met Ile
            580                 585                 590

Pro Lys Val Phe Leu Ser Ser Lys Thr Gly Val Glu Thr Tyr Lys Pro
        595                 600                 605

Ser Ala Tyr Ile Leu Glu Gly Tyr Lys Gln Asn Lys His Ile Lys Ser
        610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
            645                 650                 655
```

-continued

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Leu Ser Thr Gly Asn Asp Asn Leu His
705                 710                 715                 720

Thr Met Tyr Leu Lys Asn Leu Phe Ser Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
        755                 760                 765

Thr Tyr Glu Ala Glu Glu Lys Asp Gln Phe Gly Asn Ile Gln Ile Val
    770                 775                 780

Arg Ser Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
        835                 840                 845

Phe Lys Ala Asn Lys Thr Gly Phe Ile Asn Asp Arg Ile Leu Gln Tyr
    850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
    930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
        995                 1000                1005

Lys Gly Tyr Gln Leu Thr Tyr Ile Pro Asp Lys Leu Val Asn Val
        1010                1015                1020

Gly His Gln Cys Gly Cys Ile Phe Tyr Val Pro Ala Ala Tyr Thr
        1025                1030                1035

Ser Lys Ile Asp Pro Thr Thr Gly Phe Val Asn Ile Phe Lys Phe
        1040                1045                1050

Lys Asp Leu Thr Val Asp Ala Lys Arg Glu Phe Ile Lys Lys Phe
        1055                1060                1065

Asp Ser Ile Arg Tyr Asp Ser Glu Lys Asn Leu Phe Cys Phe Thr

```
                    1070                1075                1080

Phe Asp Tyr Asn Asn Phe Ile Thr Gln Asn Thr Val Met Ser Lys
        1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260
```

<210> SEQ ID NO 84
<211> LENGTH: 1263
<212> TYPE: PRT
<213> ORGANISM: Artificial Sequence
<220> FEATURE:
<223> OTHER INFORMATION: MAD70 VARIANT S124T, K511H, N589H, K853R, H946K, K1054Y

<400> SEQUENCE: 84

```
Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Thr Ala Lys Leu Ile
        115                 120                 125

Ser Asp Ile Leu Pro Glu Phe Val Ile His Asn Asn Asn Tyr Ser Ala
    130                 135                 140

Ser Glu Lys Glu Glu Lys Thr Gln Val Ile Lys Leu Phe Ser Arg Phe
145                 150                 155                 160
```

-continued

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
            195                 200                 205

Ser Leu Ser Asn Asp Asp Ile Asn Lys Ile Ser Gly Asp Met Lys Asp
        210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Lys Leu His Lys Gln Ile Leu Cys
        275                 280                 285

Ile Ala Asp Thr Ser Tyr Glu Val Pro Tyr Lys Phe Glu Ser Asp Glu
        290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
        370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
        450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln His Pro
            500                 505                 510

Tyr Ser Thr Lys Lys Ile Lys Leu Asn Phe Gly Ile Pro Thr Leu Ala
        515                 520                 525

Asp Gly Trp Ser Lys Ser Lys Glu Tyr Ser Asn Asn Ala Ile Ile Leu
        530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro His Lys Met Ile

```
                 580              585                590
Pro Lys Val Phe Leu Ser Ser Lys Thr Gly Val Glu Thr Tyr Lys Pro
            595             600             605

Ser Ala Tyr Ile Leu Glu Gly Tyr Lys Gln Asn Lys His Ile Lys Ser
            610             615             620

Ser Lys Asp Phe Asp Ile Thr Phe Cys His Asp Leu Ile Asp Tyr Phe
625             630             635             640

Lys Asn Cys Ile Ala Ile His Pro Glu Trp Lys Asn Phe Gly Phe Asp
                645             650             655

Phe Ser Asp Thr Ser Thr Tyr Glu Asp Ile Ser Gly Phe Tyr Arg Glu
            660             665             670

Val Glu Leu Gln Gly Tyr Lys Ile Asp Trp Thr Tyr Ile Ser Glu Lys
            675             680             685

Asp Ile Asp Leu Leu Gln Glu Lys Gly Gln Leu Tyr Leu Phe Gln Ile
            690             695             700

Tyr Asn Lys Asp Phe Ser Lys Lys Ser Thr Gly Asn Asp Asn Leu His
705             710             715             720

Thr Met Tyr Leu Lys Asn Leu Phe Ser Glu Glu Asn Leu Lys Asp Ile
                725             730             735

Val Leu Lys Leu Asn Gly Glu Ala Glu Ile Phe Phe Arg Lys Ser Ser
            740             745             750

Ile Lys Asn Pro Ile Ile His Lys Lys Gly Ser Ile Leu Val Asn Arg
            755             760             765

Thr Tyr Glu Ala Glu Glu Lys Asp Gln Phe Gly Asn Ile Gln Ile Val
            770             775             780

Arg Lys Asn Ile Pro Glu Asn Ile Tyr Gln Glu Leu Tyr Lys Tyr Phe
785             790             795             800

Asn Asp Lys Ser Asp Lys Glu Leu Ser Asp Glu Ala Ala Lys Leu Lys
                805             810             815

Asn Val Val Gly His His Glu Ala Ala Thr Asn Ile Val Lys Asp Tyr
            820             825             830

Arg Tyr Thr Tyr Asp Lys Tyr Phe Leu His Met Pro Ile Thr Ile Asn
            835             840             845

Phe Lys Ala Asn Arg Thr Gly Phe Ile Asn Asp Arg Ile Leu Gln Tyr
            850             855             860

Ile Ala Lys Glu Lys Asp Leu His Val Ile Gly Ile Asp Arg Gly Glu
865             870             875             880

Arg Asn Leu Ile Tyr Val Ser Val Ile Asp Thr Cys Gly Asn Ile Val
                885             890             895

Glu Gln Lys Ser Phe Asn Ile Val Asn Gly Tyr Asp Tyr Gln Ile Lys
            900             905             910

Leu Lys Gln Gln Glu Gly Ala Arg Gln Ile Ala Arg Lys Glu Trp Lys
            915             920             925

Glu Ile Gly Lys Ile Lys Glu Ile Lys Glu Gly Tyr Leu Ser Leu Val
            930             935             940

Ile Lys Glu Ile Ser Lys Met Val Ile Lys Tyr Asn Ala Ile Ile Ala
945             950             955             960

Met Glu Asp Leu Ser Tyr Gly Phe Lys Lys Gly Arg Phe Lys Val Glu
                965             970             975

Arg Gln Val Tyr Gln Lys Phe Glu Thr Met Leu Ile Asn Lys Leu Asn
            980             985             990

Tyr Leu Val Phe Lys Asp Ile Ser  Ile Thr Glu Asn Gly  Gly Leu Leu
            995             1000            1005
```

-continued

```
Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Tyr Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gly Asn Lys Arg Tyr Leu
    1250                1255                1260
```

<210> SEQ ID NO 85
<211> LENGTH: 1263
<212> TYPE: PRT
<213> ORGANISM: Artificial Sequence
<220> FEATURE:
<223> OTHER INFORMATION: MAD70 VARIANT K95L, S124T, N589H, K853R, K1052Q

<400> SEQUENCE: 85

```
Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
                20                  25                  30

Gln Phe Ile Val Lys Asn Gly Ile Ile Lys Glu Asp Glu Leu Arg Gly
            35                  40                  45

Glu Asn Arg Gln Ile Leu Lys Asp Ile Met Asp Tyr Tyr Arg Gly
        50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Leu Asp
                85                  90                  95
```

-continued

```
Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Thr Ala Lys Leu Ile
            115                 120                 125

Ser Asp Ile Leu Pro Glu Phe Val Ile His Asn Asn Tyr Ser Ala
        130                 135                 140

Ser Glu Lys Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
        180                 185                 190

Ala Glu Ile Phe Phe Ser Asn Ala Leu Val Tyr Arg Arg Ile Val Lys
            195                 200                 205

Ser Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Lys Leu His Lys Gln Ile Leu Cys
        275                 280                 285

Ile Ala Asp Thr Ser Tyr Glu Val Pro Tyr Lys Phe Glu Ser Asp Glu
    290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
    370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
    450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln His Pro
            500                 505                 510
```

Tyr Ser Thr Lys Lys Ile Lys Leu Asn Phe Gly Ile Pro Thr Leu Ala
        515                 520                 525

Asp Gly Trp Ser Lys Ser Lys Glu Tyr Ser Asn Asn Ala Ile Ile Leu
    530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro His Lys Met Ile
            580                 585                 590

Pro Lys Val Phe Leu Ser Ser Lys Thr Gly Val Glu Thr Tyr Lys Pro
            595                 600                 605

Ser Ala Tyr Ile Leu Glu Gly Tyr Lys Gln Asn Lys His Ile Lys Ser
    610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
    675                 680                 685

Asp Ile Asp Leu Leu Gln Glu Lys Gly Gln Leu Tyr Leu Phe Gln Ile
            690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
    755                 760                 765

Thr Tyr Glu Ala Glu Glu Lys Asp Gln Phe Gly Asn Ile Gln Ile Val
770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
    835                 840                 845

Phe Lys Ala Asn Arg Thr Gly Phe Ile Asn Asp Arg Ile Leu Gln Tyr
    850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
    915                 920                 925

Glu Ile Gly Lys Ile Lys Glu Ile Lys Glu Gly Tyr Leu Ser Leu Val

```
                930           935           940
Ile His Glu Ile Ser Lys Met Val Ile Lys Tyr Asn Ala Ile Ile Ala
945               950           955                   960

Met Glu Asp Leu Ser Tyr Gly Phe Lys Lys Gly Arg Phe Lys Val Glu
            965               970               975

Arg Gln Val Tyr Gln Lys Phe Glu Thr Met Leu Ile Asn Lys Leu Asn
                980               985               990

Tyr Leu Val Phe Lys Asp Ile Ser Ile Thr Glu Asn Gly Gly Leu Leu
        995               1000              1005

Lys Gly Tyr Gln Leu Thr Tyr Ile Pro Asp Lys Leu Lys Asn Val
1010              1015             1020

Gly His Gln Cys Gly Cys Ile Phe Tyr Val Pro Ala Ala Tyr Thr
1025              1030             1035

Ser Lys Ile Asp Pro Thr Thr Gly Phe Val Asn Ile Phe Gln Phe
1040              1045             1050

Lys Asp Leu Thr Val Asp Ala Lys Arg Glu Phe Ile Lys Lys Phe
1055              1060             1065

Asp Ser Ile Arg Tyr Asp Ser Glu Lys Asn Leu Phe Cys Phe Thr
1070              1075             1080

Phe Asp Tyr Asn Asn Phe Ile Thr Gln Asn Thr Val Met Ser Lys
1085              1090             1095

Ser Ser Trp Ser Val Tyr Thr Tyr Gly Val Arg Ile Lys Arg Arg
1100              1105             1110

Phe Val Asn Gly Arg Phe Ser Asn Glu Ser Asp Thr Ile Asp Ile
1115              1120             1125

Thr Lys Asp Met Glu Lys Thr Leu Glu Met Thr Asp Ile Asn Trp
1130              1135             1140

Arg Asp Gly His Asp Leu Arg Gln Asp Ile Ile Asp Tyr Glu Ile
1145              1150             1155

Val Gln His Ile Phe Glu Ile Phe Arg Leu Thr Val Gln Met Arg
1160              1165             1170

Asn Ser Leu Ser Glu Leu Glu Asp Arg Asp Tyr Asp Arg Leu Ile
1175              1180             1185

Ser Pro Val Leu Asn Glu Asn Asn Ile Phe Tyr Asp Ser Ala Lys
1190              1195             1200

Ala Gly Asp Ala Leu Pro Lys Asp Ala Asp Ala Asn Gly Ala Tyr
1205              1210             1215

Cys Ile Ala Leu Lys Gly Leu Tyr Glu Ile Lys Gln Ile Thr Glu
1220              1225             1230

Asn Trp Lys Glu Asp Gly Lys Phe Ser Arg Asp Lys Leu Lys Ile
1235              1240             1245

Ser Asn Lys Asp Trp Phe Asp Phe Ile Gln Asn Lys Arg Tyr Leu
1250              1255             1260

<210> SEQ ID NO 86
<211> LENGTH: 1263
<212> TYPE: PRT
<213> ORGANISM: Artificial Sequence
<220> FEATURE:
<223> OTHER INFORMATION: MAD70 VARIANT S124T, K511I, N589H, K712L,
      H946T, K1052Q, K1054N

<400> SEQUENCE: 86

Met Asn Asn Gly Thr Asn Asn Phe Gln Asn Phe Ile Gly Ile Ser Ser
1               5                   10                  15
```

Leu Gln Lys Thr Leu Arg Asn Ala Leu Ile Pro Thr Glu Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Thr Ala Lys Leu Ile
        115                 120                 125

Ser Asp Ile Leu Pro Glu Phe Val Ile His Asn Asn Asn Tyr Ser Ala
130                 135                 140

Ser Glu Lys Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
            165                 170                 175

Ala Asp Asp Ile Ser Ser Ser Cys His Arg Ile Val Asn Asp Asn
        180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
            245                 250                 255

Gly Lys Val Asn Ser Phe Met Asn Leu Tyr Cys Gln Lys Asn Lys Glu
        260                 265                 270

Asn Lys Asn Leu Tyr Lys Leu Gln Lys Leu His Lys Gln Ile Leu Cys
        275                 280                 285

Ile Ala Asp Thr Ser Tyr Glu Val Pro Tyr Lys Phe Glu Ser Asp Glu
290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
            325                 330                 335

Asn Leu Asp Lys Ile Tyr Ile Val Ser Lys Phe Tyr Glu Ser Val Ser
        340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
            405                 410                 415

Ala Glu Thr Tyr Ile His Glu Ile Ser His Ile Leu Asn Asn Phe Glu
        420                 425                 430

Ala Gln Glu Leu Lys Tyr Asn Pro Glu Ile His Leu Val Glu Ser Glu

```
                435                 440                 445
Leu Lys Ala Ser Glu Leu Lys Asn Val Leu Asp Val Ile Met Asn Ala
    450                 455                 460
Phe His Trp Cys Ser Val Phe Met Thr Glu Glu Leu Val Asp Lys Asp
465                 470                 475                 480
Asn Asn Phe Tyr Ala Glu Leu Glu Glu Ile Tyr Asp Glu Ile Tyr Pro
                485                 490                 495
Val Ile Ser Leu Tyr Asn Leu Val Arg Asn Tyr Val Thr Gln Ile Pro
            500                 505                 510
Tyr Ser Thr Lys Lys Ile Lys Leu Asn Phe Gly Ile Pro Thr Leu Ala
            515                 520                 525
Asp Gly Trp Ser Lys Ser Lys Glu Tyr Ser Asn Asn Ala Ile Ile Leu
            530                 535                 540
Met Arg Asp Asn Leu Tyr Tyr Leu Gly Ile Phe Asn Ala Lys Asn Lys
545                 550                 555                 560
Pro Asp Lys Lys Ile Ile Glu Gly Asn Thr Ser Glu Asn Lys Gly Asp
                565                 570                 575
Tyr Lys Lys Met Ile Tyr Asn Leu Leu Pro Gly Pro His Lys Met Ile
            580                 585                 590
Pro Lys Val Phe Leu Ser Ser Lys Thr Gly Val Glu Thr Tyr Lys Pro
            595                 600                 605
Ser Ala Tyr Ile Leu Glu Gly Tyr Lys Gln Asn Lys His Ile Lys Ser
            610                 615                 620
Ser Lys Asp Phe Asp Ile Thr Phe Cys His Asp Leu Ile Asp Tyr Phe
625                 630                 635                 640
Lys Asn Cys Ile Ala Ile His Pro Glu Trp Lys Asn Phe Gly Phe Asp
                645                 650                 655
Phe Ser Asp Thr Ser Thr Tyr Glu Asp Ile Ser Gly Phe Tyr Arg Glu
                660                 665                 670
Val Glu Leu Gln Gly Tyr Lys Ile Asp Trp Thr Tyr Ile Ser Glu Lys
            675                 680                 685
Asp Ile Asp Leu Leu Gln Glu Lys Gly Gln Leu Tyr Leu Phe Gln Ile
690                 695                 700
Tyr Asn Lys Asp Phe Ser Lys Leu Ser Thr Gly Asn Asp Asn Leu His
705                 710                 715                 720
Thr Met Tyr Leu Lys Asn Leu Phe Ser Glu Glu Asn Leu Lys Asp Ile
                725                 730                 735
Val Leu Lys Leu Asn Gly Glu Ala Glu Ile Phe Phe Arg Lys Ser Ser
            740                 745                 750
Ile Lys Asn Pro Ile Ile His Lys Lys Gly Ser Ile Leu Val Asn Arg
    755                 760                 765
Thr Tyr Glu Ala Glu Lys Asp Gln Phe Gly Asn Ile Gln Ile Val
    770                 775                 780
Arg Lys Asn Ile Pro Glu Asn Ile Tyr Gln Glu Leu Tyr Lys Tyr Phe
785                 790                 795                 800
Asn Asp Lys Ser Asp Lys Glu Leu Ser Asp Glu Ala Ala Lys Leu Lys
                805                 810                 815
Asn Val Val Gly His His Glu Ala Ala Thr Asn Ile Val Lys Asp Tyr
            820                 825                 830
Arg Tyr Thr Tyr Asp Lys Tyr Phe Leu His Met Pro Ile Thr Ile Asn
            835                 840                 845
Phe Lys Ala Asn Lys Thr Gly Phe Ile Asn Asp Arg Ile Leu Gln Tyr
    850                 855                 860
```

-continued

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
            885                 890                 895

Glu Gln Lys Ser Phe Asn Ile Val Asn Gly Tyr Asp Tyr Gln Ile Lys
        900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
        930                 935                 940

Ile Thr Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
            965                 970                 975

Arg Gln Val Tyr Gln Lys Phe Glu Thr Met Leu Ile Asn Lys Leu Asn
        980                 985                 990

Tyr Leu Val Phe Lys Asp Ile Ser Ile Thr Glu Asn Gly Gly Leu Leu
            995                 1000                1005

Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Gln Phe
    1040                1045                1050

Asn Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 87
<211> LENGTH: 8059
<212> TYPE: DNA
<213> ORGANISM: Artificial Sequence
<220> FEATURE:
<223> OTHER INFORMATION: EE0026 VECTOR SEQ

<400> SEQUENCE: 87

| | | | | | |
|---|---|---|---|---|---|
| gctgtttgct | cctctacaaa | acagacctta | aaccctaaa | ggcttaagta | gcaccctcgc | 60 |
| aagctcggtt | gcggccgcaa | tcgggcaaat | cgctgaatat | tccttttgtc | tccgaccatc | 120 |
| aggcacctga | gtcgctgtct | ttttcgtgac | attcagttcg | ctgcgctcac | ggctctggca | 180 |
| gtgaatgggg | gtaaatggca | ctacaggcgc | cttttatgga | ttcatgcaag | gaaactaccc | 240 |
| ataatacaag | aaaagcccgt | cacgggcttc | tcagggcgtt | ttatggcggg | tctgctatgt | 300 |
| ggtgctatct | gacttttttgc | tgttcagcag | ttcctgccct | ctgattttcc | agtctgacca | 360 |
| cttcggatta | tcccgtgaca | ggtcattcag | actggctaat | gcacccagta | aggcagcggt | 420 |
| atcatcaacg | gggtctgacg | ctcagtggaa | cgaaaactca | cgttaaggga | ttttggtcat | 480 |
| gagattatca | aaaaggatct | tcacctagat | cctttaaat | taaaaatgaa | gttttaaatc | 540 |
| aatctaaagt | atatatgagt | aaacttggtc | tgacagttat | tcttatggct | cttgtatcta | 600 |
| tcagtgaagc | atcaagacta | acaaacaaaa | gtagaacaac | tgttcaccgt | tacatatcaa | 660 |
| agggaaaact | gtccatatgc | acagatgaaa | acggtgtaaa | aaagatagat | acatcagagc | 720 |
| ttttacgagt | ttttggtgca | ttcaaagctg | ttcaccatga | acagatcgac | aatgtaacag | 780 |
| atgaacagca | tgtaacacct | aatagaacag | gtgaaaccag | taaaacaaag | caactagaac | 840 |
| atgaaattga | acacctgaga | caacttgtta | cagctcaaca | gtcacacata | gacagcctga | 900 |
| aacaggcgat | gctgcttatc | gaatcaaagc | tgccgacaac | acgggagcca | gtgacgcctc | 960 |
| ccgtggggaa | aaaatcatgg | caattctgga | agaaatagcg | ctttcagccg | gcaaaccggc | 1020 |
| tgaagccgga | tctgcgattc | tgataacaaa | ctagcaacac | cagaacagcc | cgtttgcggg | 1080 |
| cagcaaaacc | cgtcagctgt | ctcttataca | catctcgttg | ttccatacaa | cctccttagt | 1140 |
| acatgcaacc | attatcaccg | ccagaggtaa | aatagtcaac | acgcacggtg | ttagacattt | 1200 |
| atcccttgcg | gtgatagatt | taacgtatga | gcacaaaaaa | gaaaccatta | acacaagagc | 1260 |
| agcttgagga | cgcacgtcgc | cttaaagcaa | tttatgaaaa | aagaaaaat | gaacttggct | 1320 |
| tatcccagga | atctgtcgca | gacaagatgg | ggatgggca | gtcaggcgtt | ggtgctttat | 1380 |
| ttaatggcat | caatgcatta | aatgcttata | cgccgcatt | gcttacaaaa | attctcaaag | 1440 |
| ttagcgttga | agaatttagc | ccttcaatcg | ccagagaaat | ctacgagatg | tatgaagcgg | 1500 |
| ttagtatgca | gccgtcactt | agaagtgagt | atgagtaccc | tgttttttct | catgttcagg | 1560 |
| cagggatgtt | ctcacctgag | cttagaacct | ttaccaaagg | tgatgcggag | agatgggtaa | 1620 |
| gcacaaccaa | aaaagccagt | gattctgcat | tctggcttga | ggttgaaggt | aattccatga | 1680 |
| ccgcaccaac | aggctccaag | ccaagctttc | ctgacgaat | gttaattctc | gttgaccctg | 1740 |
| agcaggctgt | tgagccaggt | gatttctgca | tagccagact | tggggtgat | gagtttacct | 1800 |
| tcaagaaact | gatcagggat | agcggtcagg | tgttttaca | accactaaac | ccacagtacc | 1860 |
| caatgatccc | atgcaatgag | agttgttccg | ttgtgggaa | agttatcgct | agtcagtggc | 1920 |
| ctgaagagac | gtttggctga | tcggcaaggt | gttctggtcg | gcgcatagct | gataacaatt | 1980 |
| gagcaagaat | cttcatcgaa | ttaggggaat | tttcgctccc | ctcagaacat | aacatagtaa | 2040 |
| atggattgaa | ttatggaaaa | aaaaatcact | ggatatacca | ccgttgatat | atcccaatgg | 2100 |

```
catcgtaaag aacattttga ggcatttcag tcagttgctc aatgtaccta taaccagacc    2160
gttcagctgg atattacggc cttttaaag accgtaaaga aaataagca caagttttat    2220
ccggccttta ttcacattct tgcccgcctg atgaatgctc atccggaatt ccgtatggca    2280
atgaaagacg gtgagctggt gatatgggat agtgttcacc cttgttacac cgttttccat    2340
gagcaaactg aaacgttttc atcgctctgg agtgaatacc acgacgattt ccggcagttt    2400
ctacacatat attcgcaaga tgtggcgtgt tacggtgaaa acctggccta tttccctaaa    2460
gggtttattg agaatatgtt tttcgtctca gccaatccct gggtgagttt caccagtttt    2520
gatttaaacg tggccaatat ggacaacttc ttcgcccccg ttttcaccat gggcaaatat    2580
tatacgcaag gcgacaaggt gctgatgccg ctggcgattc aggttcatca tgccgtttgt    2640
gatggcttcc atgtcggcag aatgcttaat gaattacaac agtactgcga tgagtggcag    2700
ggcggggcgt aacccggcct cagcgccggg ttttctttgc ctcacgatcg cccccaaaac    2760
acataaccaa ttgtatttat tgaaaaataa atagatacaa ctcactaaac atagcaattc    2820
agatctctca cctaccaaac aatgcccccc tgcaaaaaat aaattcatat aaaaaacata    2880
cagataacca tctgcggtga taaattatct ctggcggtgt tgacataaat accactggcg    2940
gtgatactga gcacatcagc aggacgcact gaccaccatg aaggtgacgc tcttaaaaat    3000
taagccctga agaagggcag cattcaaagc agaaggcttt ggggtgtgtg atacgaaacg    3060
aagcattggc cgtaagtgcg attccggaaa ggagatatct cgagaaatac atctgcacta    3120
cgggggtacc tctagagaaa tcatccttag cgaaagctaa ggctgatact cttccttttt    3180
caatattatt gaagcattta tcagggttat tgtctcatga gcggatacat atttgagtgt    3240
atttagaaaa ataacaaat aggggttccg cgcacatttc cccgaaaagt gccacctgca    3300
tcgatttatt atgacaactt gacggctaca tcattcactt tttcttcaca accggcacgg    3360
aactcgctcg gctgcccc ggtgcatttt ttaaataccc gcgagaagta gagttgatcg    3420
tcaaaccaa cattgcgacc gacggtggcg ataggcatcc gggtggtgct caaaagcagc    3480
ttcgcctggc tgatacgttg gtcctcgcgc cagcttaaga cgctaatccc taactgctgg    3540
cggaaaagat gtgacagacg cgacggcgac aagcaaacat gctgtgcgac gctggcgata    3600
tcaaaattgc tgtctgccag gtgatcgctg atgtactgac aagcctcgcg tacccgatta    3660
tccatcggtg gatggagcga ctcgttaatc gcttccatgc gccgcagtaa caattgctca    3720
agcagattta tcgccagcag ctccgaatag cgcccttccc cttgcccggc gttaatgatt    3780
tgcccaaaca ggtcgctgaa atgcggctgg tgcgcttcat ccgggcgaaa gaaccccgta    3840
ttggcaaata ttgacggcca gttaagccat tcatgccagt aggcgcgcgg acgaaagtaa    3900
acccactggt gataccattc gcgagcctcc ggatgacgac cgtagtgatg aatctctcct    3960
ggcgggaaca gcaaaatatc acccggtcgg caaacaaatt ctcgtccctg attttcacc    4020
acccctgac cgcgaatggt gagattgaga atataacctt tcattcccag cggtcggtcg    4080
ataaaaaaat cgagataacc gttggcctca atcggcgtta aacccgccac cagatgggca    4140
ttaaacgagt atcccggcag caggggatca ttttgcgctt cagccatact tttcatactc    4200
ccgccattca gagaagaaac caattgtcca tattgcatca gacattgccg tcactgcgtc    4260
ttttactggc tcttctcgct aaccaaaccg gtaaccccgc ttattaaaag cattctgtaa    4320
caaagcggga ccaaagccat gacaaaaacg cgtaacaaaa gtgtctataa tcacggaaga    4380
aaagtccaca ttgattattt gcacggcgtc acactttgct atgccatagc atttttatcc    4440
```

```
ataagattag cggatcctac ctgacgcttt ttatcgcaac tctctactgt ttctccatac    4500
ccgttttttt gggaattcga gctctaagga ggttataaaa aatggatatt aatactgaaa    4560
ctgagatcaa gcaaaagcat tcactaaccc cctttcctgt tttcctaatc agcccggcat    4620
ttcgcgggcg atattttcac agctatttca ggagttcagc catgaacgct tattacattc    4680
aggatcgtct tgaggctcag agctgggcgc gtcactacca gcagctcgcc cgtgaagaga    4740
aagaggcaga actggcagac gacatggaaa aaggcctgcc ccagcacctg tttgaatcgc    4800
tatgcatcga tcatttgcaa cgccacgggg ccagcaaaaa atccattacc cgtgcgtttg    4860
atgacgatgt tgagtttcag gagcgcatgg cagaacacat ccggtacatg gttgaaacca    4920
ttgctcacca ccaggttgat attgattcag aggtatataaa cgaatgagta ctgcactcgc    4980
aacgctggct gggaagctgg ctgaacgtgt cggcatggat tctgtcgacc cacaggaact    5040
gatcaccact cttcgccaga cggcatttaa aggtgatgcc agcgatgcgc agttcatcgc    5100
attactgatc gttgccaacc agtacggcct taatccgtgg acgaaagaaa tttacgcctt    5160
tcctgataag cagaatggca tcgttccggt ggtgggcgtt gatggctggt cccgcatcat    5220
caatgaaaac cagcagtttg atggcatgga ctttgagcag acaatgaat cctgtacatg    5280 ccggatttac cgcaaggacc gtaatcatcc gatctgcgtt accgaatgga tggatgaatg    5340
ccgccgcgaa ccattcaaaa ctcgcgaagg cagagaaatc acggggccgt ggcagtcgca    5400
tcccaaacgg atgttacgtc ataaagccat gattcagtgt gcccgtctgg ccttcggatt    5460
tgctggtatc tatgacaagg atgaagccga gcgcattgtc gaaatactg catacactgc    5520 agaacgtcag ccggaacgcg acatcactcc ggttaacgat gaaaccatgc aggagattaa    5580
cactctgctg atcgccctgg ataaaacatg ggatgacgac ttattgccgc tctgttccca    5640
gatatttcgc cgcgacattc gtgcatcgtc agaactgaca caggccgaag cagtaaaagc    5700
tcttggattc ctgaaacaga agccgcaga gcagaaggtg gcagcatgac accggacatt    5760
atcctgcagc gtaccgggat cgatgtgaga gctgtcgaac aggggatga tgcgtggcac    5820 aaattacggc tcggcgtcat caccgcttca gaagttcaca acgtgatagc aaaaccccgc    5880
tccggaaaga agtggcctga catgaaaatg tcctacttcc acaccctgct tgctgaggtt    5940
tgcaccggtg tggctccgga agttaacgct aaagcactgg cctggggaaa acagtacgag    6000
aacgacgcca gaaccctgtt tgaattcact tccggcgtga atgttactga atccccgatc    6060
atctatcgcg acgaaagtat gcgtaccgcc tgctctcccg atggtttatg cagtgacggc    6120
aacggccttg aactgaaatg cccgtttacc tcccgggatt tcatgaagtt ccggctcggt    6180
ggtttcgagg ccataaagtc agcttacatg gcccaggtgc agtacagcat gtgggtgacg    6240
cgaaaaaatg cctggtactt tgccaactat gacccgcgta tgaagcgtga aggcctgcat    6300
tatgtcgtga ttgagcggga tgaaaagtac atggcgagtt ttgacgagat cgtgccggag    6360
ttcatcgaaa aaatggacga ggcactggct gaaattggtt ttgtatttgg ggagcaatgg    6420
cgatgacgca tcctcacgat aatatccggg taggcgcaat cactttcgtc tactccgtta    6480
caaagcgagg ctgggtattt cccggccttt ctgttatccg aaatccactg aaagcacagc    6540
ggctggctga ggagataaat aataaacgag gggctgtatg cacaaagcat cttctgttga    6600
gttaagaacg agtatcgaga tggcacatag ccttgctcaa attggaatca ggtttgtgcc    6660
aataccagta gaaacagacg aagaatccat gggtatggac agtttttccct ttgatatgta    6720 acggtgaaca gttgttctac ttttgtttgt tagtcttgat gcttcactga tagatacaag    6780
agccataaga acctcagatc cttccgtatt tagccagtat gttctctagt gtggttcgtt    6840
```

```
gtttttgcgt gagccatgag aacgaaccat tgagatcata cttactttgc atgtcactca   6900
aaaattttgc ctcaaaactg gtgagctgaa tttttgcagt taaagcatcg tgtagtgttt   6960
ttcttagtcc gttatgtagg taggaatctg atgtaatggt tgttggtatt ttgtcaccat   7020 tcattttat ctggttgttc tcaagttcgg ttacgagatc catttgtcta tctagttcaa    7080
cttggaaaat caacgtatca gtcgggcggc ctcgcttatc aaccaccaat ttcatattgc   7140
tgtaagtgtt taaatcttta cttattggtt tcaaaaccca ttggttaagc cttttaaact   7200
catggtagtt attttcaagc attaacatga acttaaattc atcaaggcta atctctatat   7260
ttgccttgtg agttttcttt tgtgttagtt cttttaataa ccactcataa atcctcatag   7320
agtatttgtt ttcaaaagac ttaacatgtt ccagattata ttttatgaat tttttaact    7380 ggaaaagata aggcaatatc tcttcactaa aaactaattc taattttcg cttgagaact    7440 tggcatagtt tgtccactgg aaaatctcaa agcctttaac caaaggattc ctgatttcca   7500
cagttctcgt catcagctct ctggttgctt tagctaatac accataagca tttccctac    7560 tgatgttcat catctgaacg tattggttat aagtgaacga taccgtccgt tctttccttg   7620
tagggttttc aatcgtgggg ttgagtagtg ccacacagca taaaattagc ttggtttcat   7680
gctccgttaa gtcatagcga ctaatcgcta gttcatttgc tttgaaaaca actaattcag   7740
acatacatct caattggtct aggtgatttt aatcactata ccaattgaga tgggctagtc   7800
aatgataatt actagtcctt ttcctttgag ttgtgggtat ctgtaaattc tgctagacct   7860
ttgctggaaa acttgtaaat tctgctagac cctctgtaaa ttccgctaga cctttgtgtg   7920 tttttttgt ttatattcaa gtggttataa tttatagaat aaagaaagaa taaaaaaga    7980 taaaagaat agatcccagc cctgtgtata actcactact ttagtcagtt ccgcagtatt   8040
acaaaaggat gtcgcaaac                                              8059
```

<210> SEQ ID NO 88
<211> LENGTH: 2796
<212> TYPE: DNA
<213> ORGANISM: Artificial Sequence
<220> FEATURE:
<223> OTHER INFORMATION: P346bb

<400> SEQUENCE: 88

```
atcccagaaa agacccgtcc gccatgccgt accgacccca atacccgatt ccgacaccgt    60
agcactgtga cccggccaac tcccaccatt tgtttcccaa tgtgcgccac cccatctcgg   120
gaagcttggg cccgaacaaa aactcatctc agaagaggat ctgaatagcg ccgtcgacca   180
tcatcatcat catcattgag tttaaacggt ctccagcttg gctgttttgg cggatgagag   240
aagattttca gcctgataca gattaaatca gaacgcagaa gcggtctgat aaaacagaat   300
ttgcctggcg gcagtagcgc ggtggtccca cctgacccca tgccgaactc agaagtgaaa   360
cgccgtagcg ccgatggtag tgtggggtct ccccatgcga gagtagggaa ctgccaggca   420
tcaaataaaa cgaaaggctc agtcgaaaga ctgggccttt cgttttatct gttgtttgtc   480
ggtgaactgg atccttactc gagtctagac tgcaggcttc ctcgctcact gactcgctgc   540
gctcggtcgt tcggctgcgg cgagcggtat cagctcactc aaaggcggta atacggttat   600
ccacagaatc aggggataac gcaggaaaga acatgtgagc aaaaggccag caaaaggcca   660
ggaaccgtaa aaaggccgcg ttgctggcgt ttttccatag gctccgcccc cctgacgagc   720
atcacaaaaa tcgacgctca agtcagaggt ggcgaaaccc gacaggacta taaagatacc   780
```

```
aggcgtttcc ccctggaagc tccctcgtgc gctctcctgt tccgaccctg ccgcttaccg      840
gatacctgtc cgccttttctc ccttcgggaa gcgtggcgct ttctcatagc tcacgctgta      900
ggtatctcag ttcggtgtag gtcgttcgct ccaagctggg ctgtgtgcac gaaccccccg      960
ttcagcccga ccgctgcgcc ttatccggta actatcgtct tgagtccaac ccggtaagac     1020
acgacttatc gccactggca gcagccactg gtaacaggat tagcagagcg aggtatgtag     1080
gcggtgctac agagttcttg aagtggtggc ctaactacgg ctacactaga aggacagtat     1140
ttggtatctg cgctctgctg aagccagtta ccttcggaaa aagagttggt agctcttgat     1200
ccggcaaaca aaccaccgct ggtagcggtg gttttttgt ttgcaagcag cagattacgc     1260
gcagaaaaaa aggatctcaa gaagatcctt tgatcttttc tacggggtct gacgctcagt     1320
ggaacgaaaa ctcacgttaa gggattttgg tcatgagatt atcaaaaagg atcttcacct     1380
agatcctttt aaattaaaaa tgaagtttta atcaatcta aagtatatat gagtaaactt     1440
ggtctgacag ttaccaatgc ttaatcagtg aggcacctat ctcagcgatc tgtctatttc     1500
gttcatccat agttgcctga ctccccgtcg tgtagataac tacgatacgg gagggcttac     1560
catctggccc cagtgctgca atgataccgc gagacccacg ctcaccggct ccagatttat     1620
cagcaataaa ccagccagcc ggaagggccg agcgcagaag tggtcctgca actttatccg     1680
cctccatcca gtctattaat tgttgccggg aagctagagt aagtagttcg ccagttaata     1740
gtttgcgcaa cgttgttgcc attgctacag gcatcgtggt gtcacgctcg tcgtttggta     1800
tggcttcatt cagctccggt tcccaacgat caaggcgagt tacatgatcc cccatgttgt     1860
gcaaaaaagc ggttagctcc ttcggtcctc cgatcgttgt cagaagtaag ttggccgcag     1920
tgttatcact catggttatg gcagcactgc ataattctct tactgtcatg ccatccgtaa     1980
gatgcttttc tgtgactggt gagtactcaa ccaagtcatt ctgagaatag tgtatgcggc     2040
gaccgagttg ctcttgcccg gcgtcaatac gggataatac cgcgccacat agcagaactt     2100
taaaagtgct catcattgga aaacgttctt cggggcgaaa actctcaagg atcttaccgc     2160
tgttgagatc cagttcgatg taacccactc gtgcacccaa ctgatcttca gcatctttta     2220
ctttcaccag cgtttctggg tgagcaaaaa caggaaggca aaatgccgca aaaaagggaa     2280
taagggcgac acggaaatgt tgaatactca tactcttcct ttttcaatat tattgaagca     2340
tttatcaggg ttattgtctc atgagcggat acatatttga atgtatttag aaaaataaac     2400
aaatagggt tccgcgcaca tttccccgaa aagtgccacc tgacgtctaa gaaaccatta     2460
ttatcatgac attaacctat aaaaataggc gtatcacgag gcagaatttc agataaaaaa     2520
aatccttagc tttcgctaag gatgatttct ggtctcacct accaaacaat gcccccctgc     2580
aaaaaataaa ttcatataaa aaacatacag ataaccatct gcggtgataa attatctctg     2640
gcggtgttga cataaatacc actggcggtg atactgagca catcagcagg acgcactgac     2700
caccatgaag gtgacgctct taaaaattaa gccctgaaga agggcagcat tcaaagcaga     2760
aggctttggg gtgtgtgata cgaaacgaag cattgg                             2796
```

<210> SEQ ID NO 89  
<211> LENGTH: 9232  
<212> TYPE: DNA  
<213> ORGANISM: Artificial Sequence  
<220> FEATURE:  
<223> OTHER INFORMATION: MAD70 EXPRESSION VECTOR

<400> SEQUENCE: 89

```
gcgatcgcgg ctcccgacat cttggaccat tagctccaca ggtatcttct tccctctagt        60
```

```
ggtcataaca gcagcttcag ctacctctca attcaaaaaa cccctcaaga cccgtttaga    120
ggccccaagg ggttatgcta tcaatcgttg cgttacacac acaaaaaacc aacacacatc    180
catcttcgat ggatagcgat tttattatct aactgctgat cgagtgtagc cagatctata    240
gtaatcaatt acggggtcat tagttcatag cccatatatg gagttccgcg ttacataact    300
tacggtaaat ggcccgcctg gctgaccgcc caacgacccc cgcccattga cgtcaataat    360
gacgtatgtt cccatagtaa cgccaatagg gactttccat tgacgtcaat gggtggacta    420
tttacggtaa actgcccact tggcagtaca tcaagtgtat catatgccaa gtacgccccc    480
tattgacgtc aatgacggta aatggcccgc ctggcattat gcccagtaca tgaccttatg    540
ggactttcct acttggcagt acatctacgt attagtcatc gctattacca tgcgtcgagg    600
tgagccccac gttctgcttc actctcccca tctcccccc ctcccacccc caattttgt     660 atttatttat ttttaatta ttttatgcag cgatggggg gggggggggg ggggcgcgcg    720
ccaggcgggg cggggcgggg cgaggggcgg ggcgggcga ggcggagagg tgcggcggca    780
gccaatcaga gcggcgcgct ccgaaagttt cctttatgg cgaggcggcg gcggcggcgg    840
ccctataaaa agcgaagcgc gcggcgggcg ggagtcgctg cgttgccttc gccccgtgcc    900
ccgctccgcg ccgcctcgcg ccgcccgccc cggctctgac tgaccgcgtt actcccacag    960
gtgagcgggc gggacggccc ttctccctcc gggctgtaat tagcgcttgg tttaatgacg   1020
gctcgttcct tttctgtggc tgcgtgaaag ccttaaaggg ctccgggagg gcctttgtgc   1080
gggggggagc ggctcggggg gtgcgtgcgt gtgtgtgtgc gtggggagcg ccgcgtgcgg   1140
cccgcgctgc ccggcggctg tgagcgctgc gggcgcggcg cggggctttg tgcgctccgc   1200
gtgtgcgcga ggggagcgcg ggccggggc ggtgccccgc ggtgcggggg ggctgcgagg   1260
ggaacaaagg ctgcgtgcgg ggtgtgtgcg tggggggtg agcaggggt gtgggcgcgg   1320 cggtcgggct gtaacccccc cctggcaccc ccctccccga gttgctgagc acggcccggc   1380
ttcgggtgcg gggctccgtg cggggcgtgg cgcggggctc gccgtgccgg gcgggggtg    1440 gcggcaggtg ggggtgccgg gcggggcggg gccgcctcgg gccggggagg gctcggggga   1500
ggggcgcggc ggccccggag cgccggcggc tgtcgaggcg cggcgagccg cagccattgc   1560 ctttatggt aatcgtgcga gagggcgcag ggacttcctt tgtcccaaat ctggcggagc    1620
cgaaatctgg gaggcgccgc cgcacccct ctagcgggcg cggcgaagc ggtgcggcgc    1680 cggcaggaag gaaatgggcg gggagggcct tcgtgcgtcg ccgcgccgcc gtccccttct   1740
ccatctccag cctcggggct gccgcagggg gacggctgcc ttcgggggg acggggcagg   1800 gcggggttcg gcttctggcg tgtgaccggc ggctttagag cctctgctaa ccatgttcat   1860
gccttcttct ttttcctaca gctcctgggc aacgtgctgg ttgttgtgct gtctcatcat   1920
tttggcaaag atctttgtcg atcctaccat ccactcgaca cacccgccag cggccgctgc   1980
caagcttccg agctctcgaa ttcaaaggag gtacccacat gaacaacggc acaaataatt   2040
ttcagaactt catcgggatc tcaagtttgc agaaaacgct gcgcaatgct ctgatcccca   2100
cggaaaccac gcaacagttc atcgtcaaga acggaataat taagaagat gagttacgtg   2160 gcgagaaccg ccagattctg aaagatatca tggatgacta ctaccgcgga ttcatctctg   2220
agactctgag ttctattgat gacatagatt ggactagcct gttcgaaaaa atggaaattc   2280
agctgaaaaa tggtgataat aaagataccct taattaagga acagacagag tatcggaaag   2340
caatccataa aaaatttgcg aacgacgatc ggtttaagaa catgtttagc gccaaactga   2400
```

-continued

```
ttagtgacat attacctgaa tttgtcatcc acaacaataa ttattcggca tcagagaaag    2460
aggaaaaaac ccaggtgata aaattgtttt cgcgctttgc gactagcttt aaagattact    2520
tcaagaaccg tgcaaattgc ttttcagcgg acgatatttc atcaagcagc tgccatcgca    2580
tcgtcaacga caatgcagag atattctttt caaatgcgct ggtctaccgc cggatcgtaa    2640
aatcgctgag caatgacgat atcaacaaaa tttcgggcga tatgaaagat tcattaaaag    2700
aaatgagtct ggaagaaata tattcttacg agaagtatgg ggaatttatt acccaggaag    2760
gcattagctt ctataatgat atctgtggga aagtgaattc ttttatgaac ctgtattgtc    2820
agaaaaataa agaaaacaaa aatttataca aacttcagaa acttcacaaa cagattctat    2880
gcattgcgga cactagctat gaggtcccgt ataaatttga aagtgacgag gaagtgtacc    2940
aatcagttaa cggcttcctt gataacatta gcagcaaaca tatagtcgaa agattacgca    3000
aaatcggcga taactataac ggctacaacc tggataaaat ttatatcgtg tccaaatttt    3060
acgagagcgt tagccaaaaa acctaccgcg actgggaaac aattaatacc gccctcgaaa    3120
ttcattacaa taatatcttg ccgggtaacg gtaaaagtaa agccgacaaa gtaaaaaaag    3180
cggttaagaa tgatttacag aaatccatca ccgaaataaa tgaactagtg tcaaactata    3240
agctgtgcag tgacgacaac atcaaagcgg agacttatat acatgagatt agccatatct    3300
tgaataactt tgaagcacag gaattgaaat acaatccgga aattcaccta gttgaatccg    3360
agctcaaagc gagtgagctt aaaaacgtgc tggacgtgat catgaatgcg tttcattggt    3420
gttcggtttt tatgactgag gaacttgttg ataaagacaa caatttttat gcggaactgg    3480
aggagattta cgatgaaatt tatccagtaa ttagtctgta caacctggtt cgtaactacg    3540
ttacccagaa accgtacagc acgaaaaaga ttaaattgaa ctttggaata ccgacgttag    3600
cagacggttg gtcaaagtcc aaagagtatt ctaataacgc tatcatactg atgcgcgaca    3660
atctgtatta tctgggcatc tttaatgcga agaataaacc ggacaagaag attatcgagg    3720
gtaatacgtc agaaaataag ggtgactaca aaaagatgat ttataatttg ctcccgggtc    3780
ccaacaaaat gatcccgaaa gttttcttga gcagcaagac gggggtggaa acgtataaac    3840
cgagcgccta tatcctagag gggtataaac agaataaaca tatcaagtct tcaaaagact    3900
ttgatatcac tttctgtcat gatctgatcg actacttcaa aaactgtatt gcaattcatc    3960
ccgagtggaa aaacttcggt tttgatttta gcgacaccag tacttatgaa gacatttccg    4020
ggttttatcg tgaggtagag ttacaaggtt acaagattga ttggacatac attagcgaaa    4080
aagacattga tctgctgcag gaaaaaggtc aactgtatct gttccagata tataacaaag    4140
atttttcgaa aaaatcaacc gggaatgaca accttcacac catgtacctg aaaaatcttt    4200
tctcagaaga aaatcttaag gatatcgtcc tgaaacttaa cggcgaagcg gaaatcttct    4260
tcaggaagag cagcataaag aacccaatca ttcataaaaa aggctcgatt ttagtcaacc    4320
gtacctacga agcagaagaa aaagaccagt tggcaacat tcaaattgtg cgtaaaaata    4380
ttccggaaaa catttatcag gagctgtaca aatacttcaa cgataaaagc gacaaagagc    4440
tgtctgatga agcagccaaa ctgaagaatg tagtgggaca ccacgaggca gcgacgaata    4500
tagtcaagga ctatcgctac acgtatgata aatacttcct tcatatgcct attacgatca    4560
atttcaaagc caataaaacg ggttttatta atgataggat cttacagtat atcgctaaag    4620
aaaaagactt acatgtgatc ggcattgatc ggggcgagcg taacctgatc tacgtgtccg    4680
tgattgatac ttgtggtaat atagttgaac agaaaagctt taacattgta aacggctacg    4740
actatcagat aaaactgaaa caacaggagg gcgctagaca gattgcgcgg aaagaatgga    4800
```

```
aagaaattgg taaaattaaa gagatcaaag agggctacct gagcttagta atccacgaga    4860
tctctaaaat ggtaatcaaa tacaatgcaa ttatagcgat ggaggatttg tcttatggtt    4920
ttaaaaaagg gcgctttaag gtcgaacggc aagtttacca gaaatttgaa accatgctca    4980
tcaataaact caactatctg gtatttaaag atatttcgat taccgagaat ggcggtctcc    5040
tgaaaggtta tcagctgaca tacattcctg ataaacttaa aaacgtgggt catcagtgcg    5100
gctgcatttt ttatgtgcct gctgcataca cgagcaaaat tgatccgacc accggctttg    5160
tgaatatctt taaattttaaa gacctgacag tggacgcaaa acgtgaattc attaaaaaat    5220
ttgactcaat tcgttatgac agtgaaaaaa atctgttctg ctttacattt gactacaata    5280
actttattac gcaaaacacg gtcatgagca atcatcgtg gagtgtgtat acatacggcg      5340
tgcgcatcaa acgtcgcttt gtgaacggcc gcttctcaaa cgaaagtgat accattgaca    5400
taaccaaaga tatggagaaa acgttggaaa tgacggacat taactggcgc gatggccacg    5460
atcttcgtca agacattata gattatgaaa ttgttcagca catattcgaa attttccgtt    5520
taacagtgca aatgcgtaac tccttgtctg aactggagga ccgtgattac gatcgtctca    5580
tttcacctgt actgaacgaa ataacatttt tttatgacag cgcgaaagcg ggggatgcac    5640
ttcctaagga tgccgatgca aatggtgcgt attgtattgc attaaaaggg ttatatgaaa    5700
ttaaacaaat taccgaaaat tggaagaag atggtaaatt ttcgcgcgat aaactcaaaa     5760
tcagcaataa agattggttc gactttatcc agaataagcg ctatctcatc tacctcgagg    5820
tttcgaagag accggcggcc accaaaaaag ctgggcaggc aaaaaagaag aagggttctg    5880
ggaagccgat acctaaccca ctcctcgggc ttgacagcac ataactagaa gttgtctcct    5940
cctgcactga ctgactgata caatcgattt ctggatccgc aggcctctgc tagcttgact    6000
gactgagata cagcgtacct tcagctcaca gacatgataa gatacattga tgagtttgga    6060
caaaccacaa ctagaatgca gtgaaaaaaa tgctttattt tgtgaaatttg tgatgctatt    6120 gctttatttg taaccattat aagctgcaat aaacaagtta acaacaacaa ttgcattcat    6180
tttatgtttc aggttcaggg ggaggtgtgg gaggtttttt aaagcaagta aaacctctac    6240
aaatgtggta ttggcccatc tctatcggta tcgtagcata accccttggg gcctctaaac    6300
gggtcttgag gggttttttg tgccccctcgg gccggattgc tatctaccgg cattggcgca    6360
gaaaaaaatg cctgatgcga cgctgcgcgt cttatactcc cacatatgcc agattcagca    6420
acggatacgg cttccccaac ttgcccactt ccatacgtgt cctccttacc agaaatttat    6480
ccttaaggtc gtcagctatc ctgcaggcga tctctcgatt tcgatcaaga cattccttta    6540
atggtctttt ctggacacca ctaggggtca gaagtagttc atcaaacttt cttccctccc    6600
taatctcatt ggttaccttg ggctatcgaa acttaattaa ccagtcaagt cagctacttg    6660
gcgagatcga cttgtctggg tttcgactac gctcagaatt gcgtcagtca agttcgatct    6720
ggtccttgct attgcacccg ttctccgatt acgagtttca tttaaatcat gtgagcaaaa    6780
ggccagcaaa aggccaggaa ccgtaaaaag gccgcgttgc tggcgttttt ccataggctc    6840 cgccccctg acgagcatca caaaaatcga cgctcaagtc agaggtggcg aaacccgaca     6900
ggactataaa gataccaggc gtttccccct ggaagctccc tcgtgcgctc tcctgttccg    6960
accctgccgc ttaccggata cctgtccgcc tttctccctt cgggaagcgt ggcgctttct    7020
catagctcac gctgtaggta tctcagttcg gtgtaggtcg ttcgctccaa gctgggctgt    7080
gtgcacgaac cccccgttca gcccgaccgc tgcgccttat ccggtaacta tcgtcttgag    7140
```

```
tccaacccgg taagacacga cttatcgcca ctggcagcag ccactggtaa caggattagc    7200
agagcgaggt atgtaggcgg tgctacagag ttcttgaagt ggtggcctaa ctacggctac    7260
actagaagaa cagtatttgg tatctgcgct ctgctgaagc cagttacctt cggaaaaaga    7320
gttggtagct cttgatccgg caaacaaacc accgctggta gcggtggttt ttttgtttgc    7380
aagcagcaga ttacgcgcag aaaaaaagga tctcaagaag atcctttgat cttttctacg    7440
gggtctgacg ctcagtggaa cgaaaactca cgttaaggga ttttggtcat gagattatca    7500
aaaaggatct tcacctagat ccttttaaat taaaaatgaa gttttaaatc aatctaaagt    7560
atatatgagt aaacttggtc tgacagttac caatgcttaa tcagtgaggc acctatctca    7620
gcgatctgtc tatttcgttc atccatagtt gcatttaaat ttccgaactc tccaaggccc    7680
tcgtcggaaa atcttcaaac ctttcgtccg atccatcttg caggctacct ctcgaacgaa    7740
ctatcgcaag tctcttggcc ggccttgcgc cttggctatt gcttggcagc gcctatcgcc    7800
aggtattact ccaatcccga atatccgaga tcgggatcac ccgagagaag ttcaacctac    7860
atcctcaatc ccgatctatc cgagatccga ggaatatcga atcggggcg cgcctggtgt    7920
accgagaacg atcctctcag tgcgagtctc gacgatccat atcgttgctt ggcagtcagc    7980
cagtcggaat ccagcttggg acccaggaag tccaatcgtc agatattgta ctcaagcctg    8040
gtcacggcag cgtaccgatc tgtttaaacc tagatattga tagtctgatc ggtcaacgta    8100
taatcgagtc ctagcttttg caaacatcta tcaagagaca ggatcagcag gaggctttcg    8160
catgattgaa caagatggat tgcacgcagg ttctccggcg gcttgggtgg agaggctatt    8220
cggctatgac tgggcacaac agacaatcgg ctgctctgat gccgccgtgt tccggctgtc    8280
agcgcagggg cgtccggttc ttttttgtcaa gaccgacctg tccggtgccc tgaatgaact    8340
gcaagacgag gcagcgcggc tatcgtggct ggcgacgacg ggcgttcctt gcgcggctgt    8400
gctcgacgtt gtcactgaag cgggaaggga ctggctgcta ttgggcgaag tgccggggca    8460
ggatctcctg tcatctcacc ttgctcctgc cgagaaagta tccatcatgg ctgatgcaat    8520
gcggcggctg catacgcttg atccggctac ctgcccattc gaccaccaag cgaaacatcg    8580
catcgagcga gcacgtactc ggatggaagc cggtcttgtc gatcaggatg atctggacga    8640
agagcatcag gggctcgcgc cagccgaact gttcgccagg ctcaaggcgt ctatgcccga    8700
cggcgaggat ctcgtcgtga cccacggcga tgcctgcttg ccgaatatca tggtggaaaa    8760
tggccgcttt tctggattca tcgactgtgg ccgtctgggt gtggcggacc gctatcagga    8820
catagcgttg gctacccgtg atattgctga agagcttggc ggcgaatggg ctgaccgctt    8880
ccttgtgctt tacggtatcg ccgcgcccga ttcgcagcgc atcgccttct atcgccttct    8940
tgacgagttc ttctgaccga ttctaggtgc attggcgcag aaaaaaatgc ctgatgcgac    9000
gctgcgcgtc ttatactccc acatatgcca gattcagcaa cggatacggc ttccccaact    9060
tgcccacttc catacgtgtc ctccttacca gaaatttatc cttaaggtcg tttaaactcg    9120
actctggctc tatcgaatct ccgtcgtttc gagcttacgc gaacagccgt ggcgctcatt    9180
tgctcgtcgg gcatcgaatc tcgtcagcta tcgtcagctt acctttttgg ca            9232
```

<210> SEQ ID NO 90
<211> LENGTH: 3064
<212> TYPE: DNA
<213> ORGANISM: Artificial Sequence
<220> FEATURE:
<223> OTHER INFORMATION: GRNA EXPRESSION VECTOR FOR MAMMALIAN CELLS

<400> SEQUENCE: 90

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accaaatgcg gtgtgaaata ccgcacagat gcgtaaggag aaaataccgc atcaggcgcc     240
attcgccatt caggctgcgc aactgttggg aagggcgatc ggtgcgggcc tcatcgctat     300
tacgccagct ggcgaaaggg ggatgtgctg caaggcgatt aagttgggta acgccagggt     360
tttcccagtc acgacgttgt aaaacgacgg ccagtgcaac gcgatgacga tggatagcga     420
ttcatcgatg agctgacccg atcgccgccg cggagggtt gcgtttgaga cgggcgacag      480
atgagggcct atttcccatg attccttcat atttgcatat acgatacaag gctgttagag     540
agataattgg aattaatttg actgtaaaca caaagatatt agtacaaaat acgtgacgta     600
gaaagtaata atttcttggg tagtttgcag ttttaaaatt atgttttaaa atggactatc     660
atatgcttac cgtaacttga agtatttcg atttcttggc tttatatatc ttgtggaaag      720
gacgaaacac cgtcaaaaga cctttggaat ttctactctt gtagatccgt caccaaaatc     780
agattcattt ttttatcagt tctgaccag cgagctgtgc tgcgactcgt ggcgtaatca      840
tggtcatagc tgtttcctgt gtgaaattgt tatccgctca caattccaca caacatacga     900 gccgaagca taaagtgtaa agcctggggt gcctaatgag tgagctaact cacattaatt      960
gcgttgcgct cactgcccgc tttccagtcg ggaaacctgt cgtgccagct gcattaatga    1020
atcggccaac gcgcgggag aggcggtttg cgtattgggc gctcttccgc ttcctcgctc     1080
actgactcgc tgcgctcggt cgttcggctg cggcgagcgg tatcagctca ctcaaaggcg    1140
gtaatacggt tatccacaga atcaggggat aacgcaggaa agaacatgtg agcaaaaggc    1200
cagcaaaagg ccaggaaccg taaaaaggcc gcgttgctgg cgttttttcca taggctccgc    1260 cccccctgacg agcatcacaa aaatcgacgc tcaagtcaga ggtggcgaaa cccgacagga    1320
ctataaagat accaggcgtt tccccctgga agctccctcg tgcgctctcc tgttccgacc    1380
ctgtcgctta ccggatacct gtccgccttt ctcccttcgg gaagcgtggc gctttctcat    1440
agctcacgct gtaggtatct cagttcggtg taggtcgttc gctccaagct gggctgtgtg    1500
cacgaacccc ccgttcagcc cgaccgctgc gccttatccg gtaactatcg tcttgagtcc    1560
aacccggtaa gacacgactt atcgccactg gcagcagcca ctggtaacag gattagcaga    1620
gcgaggtatg taggcggtgc tacagagttc ttgaagtggt ggcctaacta cggctacact    1680
agaagaacag tatttggtat ctgcgctctg ctgaagccag ttaccttcgg aaaaagagtt    1740
ggtagctctt gatccggcaa acaaaccacc gctggtagcg gtggttttt tgtttgcaag    1800 cagcagatta cgcgcagaaa aaaggatct caagaagatc ctttgatctt ttctacgggg     1860
tctgacgctc agtggaacga aaactcacgt taagggattt tggtcatgag attatcaaaa    1920
aggatcttca cctagatcct tttaaattaa aaatgaagtt ttaaatcaat ctaaagtata    1980
tatgagtaaa cttggtctga cagttaccaa tgcttaatca gtgaggcacc tatctcagcg    2040
atctgtctat ttcgttcatc catagttgcc tgactccccg tcgtgtagat aactacgata    2100
cgggagggct taccatctgg ccccagtgct gcaatgatac cgcgagaccc acgctcaccg    2160
gctccagatt tatcagcaat aaaccagcca gccggaaggg ccgagcgcag aagtggtcct    2220
gcaactttat ccgcctccat ccagtctatt aattgttgcc gggaagctag agtaagtagt    2280
tcgccagtta atagtttgcg caacgttgtt gccattgcta caggcatcgt ggtgtcacgc    2340
```

```
                                                  -continued tcgtcgtttg gtatggcttc attcagctcc ggttcccaac gatcaaggcg agttacatga    2400
tcccccatgt tgtgcaaaaa agcggttagc tccttcggtc ctccgatcgt tgtcagaagt    2460
aagttggccg cagtgttatc actcatggtt atggcagcac tgcataattc tcttactgtc    2520
atgccatccg taagatgctt ttctgtgact ggtgagtact caaccaagtc attctgagaa    2580
tagtgtatgc ggcgaccgag ttgctcttgc ccggcgtcaa tacgggataa taccgcgcca    2640
catagcagaa ctttaaaagt gctcatcatt ggaaaacgtt cttcggggcg aaaactctca    2700
aggatcttac cgctgttgag atccagttcg atgtaaccca ctcgtgcacc caactgatct    2760
tcagcatctt ttactttcac cagcgtttct gggtgagcaa aaacaggaag gcaaaatgcc    2820
gcaaaaaagg gaataagggc gacacggaaa tgttgaatac tcatactcta cctttttcaa    2880
tattattgaa gcatttatca gggttattgt ctcatgagcg gatacatatt tgaatgtatt    2940
tagaaaaata aacaaatagg ggttccgcgc acatttcccc gaaaagtgcc acctgacgtc    3000
taagaaacca ttattatcat gacattaacc tataaaaata ggcgtatcac gaggccctttcgtc    3060 cgtc                                                                3064
```